(12) United States Patent
Battista et al.

(10) Patent No.: US 7,939,057 B2
(45) Date of Patent: May 10, 2011

(54) METHODS AND COMPOSITIONS FOR MODULATING THE MOBILIZATION OF STEM CELLS

(75) Inventors: Michela Battista, Bronx, NY (US); Paul S. Frenette, New York, NY (US); Wei-Ming Kao, New York, NY (US)

(73) Assignee: Mount Sinai School of Medicine, New York, NY (US)

( * ) Notice: Subject to any disclaimer, the term of this patent is extended or adjusted under 35 U.S.C. 154(b) by 370 days.

(21) Appl. No.: 11/698,291

(22) Filed: Jan. 25, 2007

(65) Prior Publication Data
US 2007/0190023 A1    Aug. 16, 2007

Related U.S. Application Data

(60) Provisional application No. 60/761,872, filed on Jan. 25, 2006.

(51) Int. Cl.
| | |
|---|---|
| A61K 38/17 | (2006.01) |
| A61K 38/18 | (2006.01) |
| A61K 38/19 | (2006.01) |
| A61K 48/00 | (2006.01) |
| C07K 14/435 | (2006.01) |
| C07K 14/475 | (2006.01) |
| C07K 14/52 | (2006.01) |

(52) U.S. Cl. ............... 424/85.1; 424/198.1; 514/7.6; 514/7.9; 514/13.5; 514/44 A; 530/350; 530/351; 530/399

(58) Field of Classification Search .................. None
See application file for complete search history.

(56) References Cited

OTHER PUBLICATIONS

Cottler-Fox et al. Stem cell mobiliation. Hematology Am Soc Hematol Educ Program. pp. 419-437, 2003.*
Lapidot et al. Current understanding of stem cell mobilization: the roles of chemokines, proteolytic enzymes, adhesion molecules, cytokines, and stromal cells. Exp Hematol 30: 973-981, 2002.*
Mohle et al. Hematopoietic growth factors for hematopoietic stem cell mobilization and expansion. Semin Hematol 44: 193-202, 2007.*
Schpall, E. The utilization of cytokines in stem cell mobilization strategies. Bone Marrow Transplant 23 (Suppl 2): S13-19, 1999.*
Katayama et al. Signals from the sympathetic nervous system regulate hematopoietic stem cell egress from bone marrow. Cell 124: 407-421, 2006.*
Przala et al. Influence of albuterol on erythropoietin production and erythroid progenitor cell activation. Am J Physiol Heart Circ Physiol 236: H422-H426, 1979 (abstract only).*
Scherr et al. RNA interference (RNAi) in hematology. Ann Hematol 83: 1-8, 2004.*
Levesque et al. Characterization of hematopoietic progenitor mobilization in protease-deficient mice. Blood 104: 65-72, 2004.*
Grzegorzewski et al. Mobilization of long-term reconstituting hematopoietic stem cells in mice by recombinant human interleukin-7, J Exp Med 181:369-374, 1995.*
Jackson et al. Interleukin-12 enhances peripheral hematopoiesis in vivo. Blood 85(9): 2371-2376, 1995.*
Eto et al. Effects of macrophage colony-stimulating factor (M-CSF) on the mobilization of peripheral blood stem cells. Bone Marrow Transplant 13(2): 125-129, 1994.*
Stiff et al. A randomized phase 2 study of PBPC mobilization by stem cell factor and filgrastim in heavily pretreated patients with Hodgkin's disease or non-Hodgkin's lymphoma. Bone Marrow Transplant 26: 471-481, 2000.*
Shpall et al. A randomized phase 3 study of peripheral blood progenitor cell mobilization with stem cell factor and filgrastim in high-risk breast cancer patients. Blood 93(3): 2491-2501, 1999.*
Rogausch et al. Norepinephrine stimulates lymphoid cell mobilization from the perfused rat spleen via beta-adrenergic receptors. Am J Physiol 276(45): R724-R730, 1999.*
Przala et al. Influence of albuterol on erythropoietin production and erythroid progenitor cell activation. Am J Physiol 236(3): H422-H426, 1979.*
Fruehauf et al. Innovative strategies for PBPC mobilization. Cytotherap 7(5): 438-446, 2005.*
Rayburn et al. Antisense, RNAi, and gene silencing strategies for therapy: Mission impossible or impossible? Drug Disc Today 13 (11/12): 513-521), 2008.*
Devi, GR. siRNA-based approaches in cancer therapy. Cancer Gene Therapy 13: 819-829, 2006.*
Racz et al. Can siRNA technology provide the tools for gene therapy of the future? Curr Medicinal Chem 13: 2299-2307, 2006.*
Cohen et al., Bone marrow norepinephrine mediates development of functionally different macrophages after thermal injury and sepsis, Annals of Surgery, 2004; 240(1): 132-141.
Grabarek et al., Human kit ligand (stem cell factor) modulates platelet activation in vitro, The Journal of Biological Chemistry, 1994; 269(34): 21718-21724.
Hakuno et al., Bone marrow-derived regenerated cardiomyocytes (CMG cells) express functional adrenergic and muscarinic receptors, Circulation, 2002; 105:380-386.
Marko et al., Isolation of preadipocyte cell line from rat bone marrow and differentiation to adipocytes, Endocrinology, 1995; 136(10): 4582-4588.
Rosendaal et al., Up-regulation of the connexin43+ gap junction network in haemopoietic tissues before the growth of stem cells, Journal of Cell Science, 1994; 107:29-37.

* cited by examiner

*Primary Examiner* — Bridget E Bunner
(74) *Attorney, Agent, or Firm* — Klauber & Jackson LLC

(57) ABSTRACT

Methods and compositions for modulating the mobilization of stem cells, particularly for promoting or increasing the mobilization of hematopoietic stem cells from the bone marrow to the peripheral blood are disclosed. In particular, the invention relates to the use of adrenergic agonists that act in concert with a mobilization compound or agent. The mobilization agent(s) may act to decrease the expression or function of the chemokine, CXCL12, or may act to block or antagonize CXCR4. The invention also relates to methods of using these compounds or agents for enhancing the mobilization of hematopoietic stem cells when harvesting of the stem cells is necessary for the treatment of diseases, disabilities or conditions whereby transplantation of such cells would be beneficial in ameliorating the symptoms associated with such diseases, disabilities or conditions. Methods of screening for novel agents and pharmaceutical compositions comprising these agents are also disclosed.

29 Claims, 18 Drawing Sheets

AMD-3100 Structure 1, 1'-[1,4-phenylenebis (methylene)]-bis 1,4,8,11-azatetradecane

METHODS AND COMPOSITIONS FOR MODULATING THE MOBILIZATION OF STEM CELLS

CROSS-REFERENCE TO RELATED APPLICATIONS

The present application is a non-provisional application claiming the priority of copending provisional application Ser. No. 60/761,872, filed Jan. 25, 2006, the disclosure of which is incorporated by reference herein in its entirety. Applicants claim the benefits of this application under 35 U.S.C. §119 (e).

GOVERNMENTAL SUPPORT

This invention was made with government support under RO1 DK056638, awarded by the National Institute of Health. The government has certain rights in the invention.

FIELD OF THE INVENTION

This invention relates generally to methods and compositions for modulating the mobilization of stem cells, particularly for promoting or increasing the mobilization of hematopoietic stem cells from the bone marrow to the peripheral blood, or alternatively, for preventing the movement of cancer stem cells from their niche in the microenvironment to distant organs and tissues. In particular, the invention relates to the use of adrenergic agonists that act in concert with a compound or agent that decreases the expression or function of the chemokine, CXCL12, to enhance the mobilization of hematopoietic stem cells from the bone marrow to the blood compartment. The invention also relates to methods of using these compounds or agents for enhancing the mobilization of hematopoietic stem cells when harvesting of the stem cells is necessary for the treatment of diseases, disabilities or conditions whereby transplantation of such cells would be beneficial in ameliorating the symptoms associated with such diseases, disabilities or conditions. The invention also relates to the use of these agents as adjunct therapy with chemotherapy or irradiation therapy for treating cancerous conditions or for the prevention of cancer metastasis. Methods of screening for novel agents and pharmaceutical compositions comprising these agents is also disclosed.

BACKGROUND OF THE INVENTION

Hematopoietic stem and progenitor cells (HSPCs) reside in specific niches that control survival, proliferation, self-renewal or differentiation in the bone marrow (BM). Stem cells closely associate with spindle-shaped N-cadherin- and Angiopoietin-1-expressing osteoblasts that line the endosteal bone (Calvi, L. M., Adams, G. B., Weibrecht, K. W., Weber, J. M., Olson, D. P., Knight, M. C., Martin, R. P., Schipani, E., Divieti, P., Bringhurst, F. R., et al. (2003). Osteoblastic cells regulate the haematopoietic stem cell niche. Nature 425, 841-846; Zhang, J., Niu, C., Ye, L., Huang, H., He, X., Tong, W. G., Ross, J., Haug, J., Johnson, T., Feng, J. Q., et al. (2003). Identification of the haematopoietic stem cell niche and control of the niche size. Nature 425, 836-841; Arai, F., Hirao, A., Ohmura, M., Sato, H., Matsuoka, S., Takubo, K., Ito, K., Koh, G. Y., and Suda, T. (2004). Tie2/angiopoietin-1 signaling regulates hematopoietic stem cell quiescence in the bone marrow niche. Cell 118, 149-161). In normal individuals, the continuous trafficking of HSPCs between the BM and blood compartments likely fills empty or damaged niches and contributes to the maintenance of normal hematopoiesis (Wright, D. E., Wagers, A. J., Gulati, A. P., Johnson, F. L., and Weissman, I. L. (2001). Physiological migration of hematopoietic stem and progenitor cells. Science 294, 1933-1936; Abkowitz, J. L., Robinson, A. E., Kale, S., Long, M. W., and Chen, J. (2003). Mobilization of hematopoietic stem cells during homeostasis and after cytokine exposure. Blood 102, 1249-1253). Although it has been known for many years that the egress of HSPCs can be enhanced by multiple agonists, the mechanisms that regulate this critical process are largely unknown.

The hematopoietic cytokine granulocyte-colony stimulating factor (G-CSF) is widely used clinically to elicit HSPC mobilization for life-saving BM transplantation and has thus served as the prototype to gain mechanistic insight about this phenomenon (Lapidot, T., and Petit, I. (2002). Current understanding of stem cell mobilization: the roles of chemokines, proteolytic enzymes, adhesion molecules, cytokines, and stromal cells. Exp Hematol 30, 973-981; Papayannopoulou, T. (2004). Current mechanistic scenarios in hematopoietic stem/progenitor cell mobilization. Blood 103, 1580-1585). While mice deficient in the G-CSF receptor (G-CSFR$^{-/-}$) are unresponsive to G-CSF stimulation, G-CSFR$^{-/-}$ HSPCs can be elicited by G-CSF in chimeric mice that harbored mixtures of G-CSFR$^{+/+}$ and G-CSFR$^{-/-}$ hematopoietic cells, suggesting the contribution of 'trans-acting' signals (Liu, F., Poursine-Laurent, J., and Link, D. C. (2000). Expression of the G-CSF receptor on hematopoietic progenitor cells is not required for their mobilization by G-CSF. Blood 95, 3025-3031). Subsequent studies have suggested that these transacting signals originated from the release of proteases including serine- and metallo-proteinases whose substrates include various molecules implicated in progenitor trafficking such as VCAM-1 (Levesque, J. P., Takamatsu, Y., Nilsson, S. K., Haylock, D. N., and Simmons, P. J. (2001). Vascular cell adhesion molecule-1 (CD106) is cleaved by neutrophil proteases in the bone marrow following hematopoietic progenitor cell mobilization by granulocyte colony-stimulating factor. Blood 98, 1289-1297), membrane-bound Kit ligand (Heissig, B., Hattori, K., Dias, S., Friedrich, M., Ferris, B., Hackett, N. R., Crystal, R. G., Besmer, P., Lyden, D., Moore, M. A., et al. (2002). Recruitment of stem and progenitor cells from the bone marrow niche requires MMP-9 mediated release of kit-ligand. Cell 109, 625-637), the c-Kit receptor, stromal-derived factor-1 (SDF-1 or CXCL12) (Petit, I., Szyper-Kravitz, M., Nagler, A., Lahav, M., Peled, A., Habler, L., Ponomaryov, T., Taichman, R. S., Arenzana-Seisdedos, F., Fujii, N., et al. (2002). G-CSF induces stem cell mobilization by decreasing bone marrow SDF-1 and up-regulating CXCR4. Nat Immunol 3, 687-694; Levesque, J. P., Hendy, J., Takamatsu, Y., Simmons, P. J., and Bendall, L. J. (2003). Disruption of the CXCR4/CXCL12 chemotactic interaction during hematopoietic stem cell mobilization induced by GCSF or cyclophosphamide. J Clin Invest 111, 187-196) and its cognate receptor CXCR4 (Levesque, J. P., Hendy, J., Takamatsu, Y., Simmons, P. J., and Bendall, L. J. (2003). Disruption of the CXCR4/CXCL12 chemotactic interaction during hematopoietic stem cell mobilization induced by GCSF or cyclophosphamide. J Clin Invest 111, 187-196). Among these, the CXCL12-CXCR4 axis has emerged as a likely effector because it is the sole chemokine-receptor pair capable of attracting HSPCs (Wright, D. E., Bowman, E. P., Wagers, A. J., Butcher, E. C., and Weissman, I. L. (2002). Hematopoietic stem cells are uniquely selective in their migratory response to chemokines. J Exp Med 195, 1145-1154) and its disruption is sufficient to induce mobilization (Broxmeyer, H. E., Orschell, C. M., Clapp, D. W., Hangoc, G., Cooper, S., Plett, P. A., Liles, W. C., Li, X., Graham-Evans, B., Campbell, T. B., et al. (2005). Rapid mobilization of murine and human hematopoietic stem and progenitor cells with AMD3100, a CXCR4 antagonist. J Exp Med 201, 1307-1318). However, the function of these proteases has been challenged by other data indicating that G-CSF-induced mobilization was normal in mice lacking virtually all neutrophil serine protease activity, even when combined with a broad metalloproteinase inhibitor (Levesque, J. P., Liu, F., Simmons, P. J., Betsuyaku, T., Senior, R. M., Pham, C., and Link, D. C. (2004). Characterization of hematopoietic progenitor mobilization in protease-deficient mice. Blood 104, 65-72). This suggests that other proteases and/or other mechanisms are involved.

The sulfated fucose polymer fucoidan can rapidly elicit HSPC mobilization (Frenette, P. S., and Weiss, L. (2000). Sulfated glycans induce rapid hematopoietic progenitor cell mobilization: evidence for selectin-dependent and independent mechanisms. Blood 96, 2460-2468; Sweeney, E. A., Priestley, G. V., Nakamoto, B., Collins, R. G., Beaudet, A. L., and Papayannopoulou, T. (2000). Mobilization of stem/progenitor cells by sulfated polysaccharides does not require selectin presence. Proc Natl Acad Sci USA 97, 6544-6549). Fucoidan is synthesized by certain seaweeds, and sulfatide, is a sulfated galactolipid synthesized by mammalian cells (Roberts, D. D., Rao, C. N., Liotta, L. A., Gralnick, H. R., and Ginsburg, V. (1986). Comparison of the specificities of laminin, thrombospondin, and von Willebrand factor for binding to sulfated glycolipids. J Biol Chem 261, 6872-6877; Skinner, M. P., Lucas, C. M., Burns, G. F., Chesterman, C. N., and Berndt, M. C. (1991). GMP-140 binding to neutrophils is inhibited by sulfated glycans. J Biol Chem 266, 5371-5374; Waddell, T. K., Fialkow, L., Chan, C. K., Kishimoto, T. K., and Downey, G. P. (1995). Signaling functions of L-selectin. Enhancement of tyrosine phosphorylation and activation of MAP kinase. J Biol Chem 270, 15403-15411; Waddell, T. K., Fialkow, L., Chan, C. K., Kishimoto, T. K., and Downey, G. P. (1995). Signaling functions of L-selectin. Enhancement of tyrosine phosphorylation and activation of MAP kinase. J Biol Chem 270, 15403-15411). The synthesis of sulfatide and its non-sulfated form galactosylceramide (GalCer) is initiated by the addition of UDP-galactose to ceramide in a reaction mediated by UDP-galactose:ceramide galactosyltransferase (Cgt), an enzyme highly expressed in oligodendrocytes and Schwann cells (Sprong, H., Kruithof, B., Leijendekker, R., Slot, J. W., van Meer, G., and van der Sluijs, P. (1998). UDP-galactose:ceramide galactosyltransferase is a class I integral membrane protein of the endoplasmic reticulum. J Biol Chem 273, 25880-25888). The products of Cgt, collectively referred to as galactocerebrosides (GCs), are a major component of the myelin sheaths that facilitate the transmission of saltatory conduction (Norton, W. T., and Cammer, W. (1984). Isolation and characterization of myelin. In Myelin, P. Morell, ed. (New York, Plenum Press), pp. 147-195). Predictably, $Cgt^{-/-}$ mice display defects in nerve conduction and die on postnatal days 18-30 from severe tremor and ataxia (Coetzee, T., Fujita, N., Dupree, J., Shi, R., Blight, A., Suzuki, K., and Popko, B. (1996). Myelination in the absence of galactocerebroside and sulfatide: normal structure with abnormal function and regional instability. Cell 86, 209-219; Bosio, A., Binczek, E., and Stoffel, W. (1996). Functional breakdown of the lipid bilayer of the myelin membrane in central and peripheral nervous system by disrupted galactocerebroside synthesis. Proc Natl Acad Sci USA 93, 13280-13285).

A variety of diseases, in particular cancers and hyperproliferative disorders, require treatment with agents that are preferentially cytotoxic to dividing cells. These therapies include high doses of irradiation or chemotherapeutic agents. While these doses are necessary to kill off the cancer cells, a significant side-effect of these approaches to cancer therapy is the pathological impact of such treatments on rapidly dividing normal cells, such as hair follicles, mucosal cells and the hematopoietic cells, such as primitive bone marrow progenitor cells and stem cells. The indiscriminate destruction of hematopoietic stem cells or progenitor/precursor cells can lead to a reduction in normal mature blood cell counts, such as lymphocytes, neutrophils and platelets. Such a decrease in white blood cell count also results in a loss of immune system function in these patients. As such, this may increase a patient's risk of acquiring opportunistic infections. Neutropenia resulting from chemotherapy or irradiation therapy may occur within a few days following cytotoxic treatments. The patient, however, is vulnerable to infection for up to one month until the neutrophil counts recover to within a normal range. If the reduced leukocyte count (leukopenia) and/or a platelet count (granulocytopenia) become sufficiently serious, therapy must be interrupted to allow for recovery of the white blood cell count. Such an interruption in the patient's therapeutic regimen may result in the survival of cancer cells, an increase drug resistance in the cancer cells, and may actually result in a relapse of the cancer.

Colony stimulating factors, like G-CSF and GM-CSF, are used in such a clinical setting as adjunct therapy with chemotherapy or irradiation therapy to allow for the recovery of bone marrow cells following such harsh treatment regimens. However, these therapies generally take one to two weeks before the peripheral blood counts reach an acceptable level such that the patient's risk of developing infections is diminished. In addition, bone marrow transplantation is sometimes used in the treatment of a variety of hematological, autoimmune and malignant diseases. In addition to bone marrow transplantation, ex vivo bone marrow cells may be cultured and used to expand the population of hematopoietic progenitor cells, prior to reintroduction of such cells into a patient. These hematopoietic stem cells or precursor cells may be used for ex vivo gene therapy, whereby the cells may be transformed in vitro prior to reintroduction of the transformed cells into the patient. In gene therapy, using conventional recombinant DNA techniques, a selected nucleic acid, such as a gene, may be isolated, placed into a vector, such as a viral vector, and the vector transfected into a hematopoietic cell, to transform the cell, and the cell may in turn express the product coded for by the gene. The cell then may then be introduced into a patient (see e.g., Wilson, J. M., et al., Proc. Natl. Acad. Sci. 85: 3014-3018 (1988)). However, there have been problems with efficient hematopoietic stem cell transfection (see Miller, A. D., Blood 76: 271-278 (1990)). The use of hematopoietic stem cell transplantation therapy is limited by several factors. For example, obtaining enough stem cells for clinical use requires either a bone marrow harvest under general anesthesia or peripheral blood leukapheresis. In addition, both procedures are expensive and may also carry a risk of morbidity. Furthermore, such grafts may contain a very limited number of useful hematopoietic progenitor cells. In addition, the cells that are engrafted may offer limited protection for the patient for the initial one to three weeks after engraftment, and therefore the recipients of the graft may remain severely myelosuppressed during this time period.

There is accordingly a need for agents and methods that facilitate the mobilization of hematopoietic stem or precursor/progenitor cells to the peripheral blood. Furthermore, the development of such agents may aid in the collection of such hematopoietic stem cells or hematopoietic progenitor cells for use in ex vivo cell cultures, whereby such cells can further be used in engraftment or transplantation procedures. Accordingly, the current invention addresses these needs.

All publications, patent applications, patents and other reference material mentioned are incorporated by reference in their entirety. In addition, the materials, methods and examples are only illustrative and are not intended to be limiting. The citation of references herein shall not be construed as an admission that such is prior art to the present invention.

SUMMARY OF THE INVENTION

In its broadest aspect, the invention provides for increasing the mobilization of stem cells, in particular, hematopoietic stem cells, from the bone marrow to the peripheral blood. The invention is further directed to compositions and methods of treating animal subjects, in particular, veterinary and human subjects, to enhance the mobilization of hematopoietic stem cells or progenitor cells from the bone marrow to the peripheral blood. The stem cells or progenitor cells may be harvested by apheresis and used in cell transplantation. The methods and compositions of the invention employ a combination of an adrenergic receptor agonist and a mobilizer of hematopoietic stem cells or progenitor cells. The adrenergic receptor agonist and the mobilizer of stem cells may also be used as adjunct therapy with chemotherapy or irradiation therapy for treating a cancerous condition. Alternatively, an adrenergic receptor antagonist may be used for preventing the egress of a cancer stem cell from its niche in a microenvironment to a distant organ or tissue.

Accordingly, a first aspect of the invention provides a method for increasing or promoting the mobilization of hematopoietic stem cells or progenitor cells from the bone marrow to the peripheral blood in a mammalian subject, the method comprising administering an adrenergic receptor agonist and a mobilizer of hematopoietic stem cells or progenitor cells.

A second aspect of the invention provides for a method for obtaining a population of hematopoietic stem cells or progenitor cells from a subject, the method comprising the steps of:
  a) administering an adrenergic receptor agonist and a mobilizer of hematopoietic stem cells or progenitor cells to the subject in an amount sufficient to mobilize the hematopoietic stem cells or progenitor cells from the bone marrow to the peripheral blood of the subject;
  b) collecting/harvesting the mobilized cells from the peripheral blood by apheresis.

In one embodiment, the mobilizer is characterized by its ability to decrease the expression or function of the chemokine, CXCL12.

In another embodiment, the mobilizer is characterized by its ability to block or antagonize CXCR4.

A third aspect of the invention provides for a pharmaceutical composition comprising an adrenergic receptor agonist and a mobilizer of hematopoietic stem cells or progenitor cells, and a pharmaceutically acceptable carrier.

A fourth aspect of the invention provides a method of treating a subject in need of therapy with an agent that stimulates mobilization of bone marrow cells from the bone marrow to the peripheral blood, comprising administering a pharmaceutical composition comprising an adrenergic receptor agonist and a mobilizer of hematopoietic stem cells or progenitor cells as described above. Accordingly, a pharmaceutical composition comprising an adrenergic receptor modulator, either an agonist or antagonist, and a stem cell mobilizer is envisioned for use in the methods of the invention. The composition may comprise a combination of the adrenergic receptor modulator and the stem cell mobilizer alone or in further combination with an anti-cancer drug.

A fifth aspect of the invention provides a method of screening in vitro for agents that promote mobilization of hematopoietic stem cells or progenitor cells, the method comprising the steps of:
  a) plating a population of bone marrow cells with stromal cells with or without additional growth factor supplementation;
  b) supplementing the cells of step a) with medium containing a candidate or test compound with or without an adrenergic receptor agonist; and
  c) quantitating the number of hematopoietic stem cells or progenitor cells in the culture supernatant,
  wherein a candidate or test compound is considered to be effective if the number of hematopoietic stem cells or progenitor cells is greater in the culture supernatant in the presence but not in the absence of the test compound.

In one embodiment, the mobilizer is characterized by its ability to decrease the expression or function of the chemokine, CXCL12. By function is meant the ability of the chemokine to bind to its receptor and initiate the signaling cascade. In another embodiment, the mobilizer is characterized by its ability to block or antagonize the expression or function of CXCR4. By function is meant the ability of the chemokine receptor to bind to its ligand or a mimic/mimetic thereof and initiate the signaling cascade.

In another particular embodiment, the adrenergic receptor agonist is an alpha or a beta adrenergic agonist or a combination thereof.

In another particular embodiment, the alpha adrenergic agonist is an alpha 1 or alpha 2 adrenergic agonist.

In another particular embodiment, the beta adrenergic agonist is a β2 adrenergic agonist.

In yet another more particular embodiment, the beta adrenergic agonist is selected from the group consisting of isoproterenol, clenbuterol, metaproterenol, albuterol, terbutaline, salmeterol, salbutamine, bitolterol, pirburerol acetate, formoterol, epinephrine, and norepinephrine.

In yet another more particular embodiment, the mobilizer of hematopoietic stem cells or progenitor cells is selected from the group consisting of a small organic molecule, a polypeptide, a nucleic acid and a carbohydrate.

In yet another more particular embodiment, the mobilizer of hematopoietic stem cells or progenitor cells is a polypeptide selected from the group consisting of a cytokine, a colony stimulating factor, a protease or a chemokine other than CXCL12.

In yet another more particular embodiment, the mobilizer of hematopoietic stem cells or progenitor cells is a cytokine selected from the group consisting of interleukin-1 (IL-1), interleukin-3 (IL-3), interleukin-6 (IL-6), interleukin-11 (IL-11), interleukin-7 (IL-7), and interleukin-12 (IL12).

In yet another more particular embodiment, the mobilizer of hematopoietic stem cells or progenitor cells is a protease selected from the group consisting of a metalloproteinase (like MMP2 or MMP9) a serine protease, (like cathepsin G, or elastase) a cysteine protease (like cathepsin K) and a dipeptidyl peptidase-1 (DDP-1 OR CD26).

In yet another more particular embodiment, the mobilizer of hematopoietic stem cells or progenitor cells is a colony stimulating factor selected from the group consisting of granulocyte colony stimulating factor (G-CSF), granulocyte-macrophage colony stimulating factor (GM-CSF), macrophage colony stimulating factor (M-CSF), stem cell factor, FLT-3 ligand or a combination thereof.

In yet another more particular embodiment, the mobilizer of hematopoietic stem cells or progenitor cells is a chemokine other than CXCL12 selected from the group consisting of IL-8, Mip-1α, Groβ.

In yet another more particular embodiment, the mobilizer of hematopoietic stem cells or progenitor cells is a nucleic acid is a DNA or an RNA molecule.

In yet another more particular embodiment, the nucleic acid that is a mobilizer of hematopoietic stem cells or progenitor cells is a small interfering RNA (siRNA) molecule or an antisense molecule specific for CXCL12 or CXCR4.

In yet another more particular embodiment, the mobilizer of hematopoietic stem cells or progenitor cells is a carbohydrate, and more particularly, a sulfated carbohydrate selected from the group consisting of Fucoidan and sulfated dextran.

In yet another more particular embodiment, the mobilizer of hematopoietic stem cells or progenitor cells is a small organic molecule, such as, but not limited to, the CXCR4 antagonist AMD-3100 or its analogs, derivatives or combinations thereof. The structure of AMD-3100 and its derivatives and analogs thereof may be found in U.S. Pat. No. 6,987,102, which is incorporated by reference in its entirety.

In another embodiment, the pharmaceutical composition further comprises a chemotherapeutic agent.

In yet another embodiment, the pharmaceutical composition is administered before, during or after chemotherapy or irradiation therapy in a patient suffering from a cancerous condition or a hyperproliferative disorder.

In another embodiment, the pharmaceutical composition is used as adjunct therapy for treating a cancerous condition or a hyperproliferative disorder.

A sixth aspect of the invention provides methods of treating of cell populations ex vivo with the adrenergic receptor agonists and the mobilizer of hematopoietic stem cells or progenitor cells and introducing the treated populations into a compatible subject. The compounds disclosed above may be used alone or in combination with other compounds and compositions to enhance the population of stem cells and/or progenitor cells in the peripheral blood.

In accordance with a seventh aspect of the invention, the adrenergic receptor agonists, when used in combination with the mobilizers described above, including the agents that decrease the expression or function of CXCL12, or the CXCR4 antagonists, may be used to treat hematopoietic cells in vitro or in vivo. In addition, while the agents in combination act to stimulate or enhance mobilization of stem or progenitor cells from the bone marrow to the blood compartment, the agents when used together may or may not act to increase the rate of hematopoietic stem or progenitor cellular multiplication, self-renewal, expansion, and proliferation. This may for example be useful in some embodiments for in vitro hematopoietic cell cultures used in bone marrow transplantation, peripheral blood mobilization, or ex vivo use, for example, in some embodiments involving the treatment of human diseases such as a cancer. The hematopoietic cells targeted by the methods of the invention may include hematopoietic progenitor or stem cells.

The agents and methods of the invention are also contemplated for use in mobilizing or enhancing egress of quiescent cancer stem cells from their niche in the microenvironment or in a tumor mass to the circulation or to distant organs or tissues such that the cancer stem cells are put into an activated or proliferative state in order to make them more susceptible to cytoreductive therapy, which generally targets actively dividing cells. Once they are in such an activated or proliferative state, one may administer a cytoreductive therapy in the form of a chemotherapeutic drug or radiotherapy.

In alternative embodiments, the use of the adrenergic receptor agonists plus a mobilizer such as those that decrease the expression or function of CXCL12 or that block or antagonize CXCR4 may be used to treat a variety of hematopoietic cells, and such cells may be isolated or may form only part of a treated cell population in vivo or in vitro. Cells amenable to treatment with the combination of these agents may for example include cells in the hematopoietic lineage, beginning with pluripotent stem cells, such as bone marrow stem or progenitor cells, lymphoid stem or progenitor cells, myeloid stem cells, cancer stem cells, CFU-GEMM cells (colony-forming-unit granulocyte, erythroid, macrophage, megakaryocye), pre-B cells, prothymocyte), BFU-E cells (burst-forming unit-erythroid), BFU-MK cells (burst-forming unit megakaryocytes), CFU-GM cells (colony-forming unit-granulocyte-macrophage-), CFU-bas cells (colony-forming unit-basophil), CFUMast cells (colony forming unit mast cell), CFU-G cells (colony forming unit granulocyte), CFU-M/DC cells (colony forming unit monocyte/dendritic cell), CFU-Eo cells (colony forming unit eosinophil), CFU-E cells (colony forming unit erythroid), CFU-MK cells (colony forming unit megakaryocyte), myeloblasts, monoblasts, B-lymphoblasts, T-lymphoblasts, proerythroblasts, neutrophillic myelocytes, promonocytes, or other hematopoietic cells that differentiate to give rise to mature cells such as macrophages, myeloid related dendritic cells, mast cells, plasma cells, erythrocytes, platelets, neutrophils, monocytes, eosinophils, basophils, B-cells, T-cells or lymphoid related dendritic cells.

In another embodiment, the invention provides methods of increasing the circulation of hematopoietic cells by mobilizing them from the marrow to the peripheral blood comprising administering an effective amount of an adrenergic receptor agonist plus either an agent that decreases expression or function of CXCL12 or a CXCR4 mimic or antagonist to hematopoietic cells of a patient undergoing autologous mobilization where hematopoietic stem/progenitor cells may be mobilized into the peripheral blood (1) during the rebound phase of the leukocytes and/or platelets after transient granulocytopenia and thrombocytopenia induced by myelosuppressive chemotherapy, (2) by hematopoietic growth factors, or (3) by a combination of both. Such treatment may for example be carried out so as to be effective to mobilize the hematopoietic cells from a marrow locus (i.e. a location in the bone marrow) to a peripheral blood locus (i.e. a location in the peripheral blood). Such treatments may for example be undertaken in the context of or for the clinical procedure of leukapheresis or apheresis.

In alternative embodiments, a combination of an adrenergic receptor agonist plus either an agent that decreases expression or function of CXCL12 or a CXCR4 mimic or antagonist may be used in ex vivo stem cell expansion to supplement stem cell grafts with more immature precursors to shorten or potentially prevent hematopoietic cell depletion, including conditions such as pancytopenia, granulocytopenia, thrombocytopenia, anemia or a combination thereof; to increase the number of primitive progenitors to help ensure hematopoietic support for multiple cycles of high-dose therapy; to obtain sufficient number of stem cells from a single apheresis procedure, thus reducing the need for large-scale harvesting of marrow OR multiple leukopheresis; to generate sufficient cells from a single cord-blood unit to allow reconstitution in an adult after high-dose chemotherapy; to purge stem cell products of contaminating tumour cells; to generate large volumes of immunologically active cells with antitumour activity to be used in immunotherapeutic regimens or to increase the pool of stem cells that could be targets for the delivery of gene therapy.

In alternative embodiments, the invention provides methods to enrich hematopoietic progenitor cells which are utilized in bone marrow (BM) and peripheral blood (PB) stem cell transplantation, wherein the hematopoietic stem cell transplantation (HSCT) protocols may for example be utilized for the purpose of treating the following diseases (from Ball, E. D., Lister, J., and Law, P. Hematopoietic Stem Cell Therapy, Chruchill Livingston (of Harcourt Inc.), New York (2000)): Aplastic Anemia; Acute Lymphoblastic Anemia.; Acute Myelogenous Leukemia; Myelodysplasia; Multiple Myeloma; Chronic Lymphocytic Leukemia; Congenital Immunodeficiencies (such as Autoimmune Lymphoproliferative disease, Wiscott-Aldrich Syndrome, X-linked Lymphoproliferative disease, Chronic Granulamatous disease, Kostmann Neutropenia, Leukocyte Adhesion Deficiency); Metabolic Diseases (for instance those which have been HSCT indicated such as Hurler Syndrome (MPS I/II), Sly NW Syndrome (MPS VII), Chilhood onset cerebral X-adrenoleukodystrophy, Globard_cell Leukodystrophy).

A seventh aspect of the invention provides methods of preventing the migration of a stem cell from its niche in a tissue, or for retaining the stem cell within its niche in the tissue, the method comprising treating a subject with an effective amount of an adrenergic receptor antagonist.

In one embodiment, the adrenergic receptor antagonist is an alpha or a beta receptor antagonist.

In another embodiment, the beta receptor antagonist is selected from the group consisting of may be selected from the group consisting of 8-p-sulfophenyltheophylline (8-SPT), Acebutolol, Atenolol, Betxolol, Bisoprolol, Esmolol, Metoprolol, Carteolol, Nadolol, Nipradolol, Penbutolol, Pindolol, Propranolol, Sotalol, Timolol, Carvedilol, Labetalol, Alprenolol, and ICI 118,551 ((+/−)-1-[2,3-dihydro-7-methyl-1H-inden-4-yl)oxy]-3-[(1-methylethyl)amino]-2-butanol hydrochloride).

In yet another embodiment, the alpha receptor antagonist is selected from the group consisting of a haloalkylamine, an imidazoline, a quinozoline, an indole derivative, a phenoxypropanolamine, an alcohol, an alkaloid, an amine, a piperizine and a piperidine.

In yet another embodiment, the haloalkylamine is selected from the group consisting of phenoxybenzamine and dibenamine.

In yet another embodiment, the imidazolines is selected from the group consisting of phentolamine, tolazoline, idazoxan, deriglidole, RX 821002 (See Langin et al., Mol. Pharmacol., (1990), 37(6):876-885); BRL 44408 (1-(2-pyrimidinyl)-piperazine) (See Myrs Neurol Urodyn (2004) 23: 709-715) and BRL 44409 (see, Young et al, Eur. J. Pharm., 168: 381-386 (1989), and U.S. Pat. No. 6,514,934, the disclosures of which are incorporated herein by reference in their entirety).

In yet another embodiment, the quinazoline is selected from the group consisting of prazosine, terazosin, doxazosin, alfuzosin, bunazosin, ketanserin, trimazosin and abanoquil.

In yet another embodiment, the indole and indole derivative is selected from the group consisting of carvedilol and BAM 1303 (See Blaxall, Pharmacol. & Exp. Ther. 259(1): 323-329).

In yet another embodiment, the alcohol is selected from the group consisting of labetelol and ifenprodil.

In yet another embodiment, the alkaloid is selected from the group consisting of ergotoxine (which is a mixture of three alkaloids: ergocornine, ergocristine and ergocryptine), yohimbine, rauwolscine, corynathine, raubascine, tetrahydroalstonine, apoyohimbine, akuammigine, beta-yohimbine, yohimbol, pseudoyohimbine and epi-3 alpha-yohimbine.

In yet another embodiment, the amine is selected from the group consisting of tamsulosin, benoxathian, atipamezole, BE 2254 (See Hicks, J. Auton. Pharmacol. (1981), 1(5):391-397), WB 4101 (See Armenia et al., Br. J. Pharmacol. (2004), 142:719-726) and HU-723 (See U.S. Pat. No. 6,514,934).

In yet another embodiment, the piperizine is selected from the group consisting of naftopil and saterinone.

In yet another embodiment, the piperidine is haloperidol.

An eighth aspect of the invention provides a method of inhibiting the growth, proliferation, and/or metastasis of a tumor cell, comprising administering to a mammal an effective amount of an adrenergic receptor agonist, a mobilizer of stem cells and a therapeutically effective amount of either an anti-cancer agent/drug, or an amount of radiotherapy effective to inhibit growth, proliferation and/or metastasis of the tumor cell.

A ninth aspect of the invention provides a method of enhancing the migration of a cancer stem cell from its niche or microenvironment within a tissue of a subject to the circulatory or lymphatic system, or to another tissue or organ, the method comprising administering an effective amount of an adrenergic receptor agonist and a stem cell mobilizer to the subject, wherein the method results in progression of the cancer stem cell from a quiescent state within the microenvironment to a proliferative state; and wherein the method further comprises treating the subject with cytoreductive therapy, wherein the cytoreductive therapy comprises either an effective amount of an anti-cancer drug or an effective amount of radiation therapy.

In one embodiment, the mobilizer is characterized by its ability to decrease or block the expression, synthesis or function of CXCL12 or is characterized by its ability to block or antagonize CXCR4.

In another embodiment, the adrenergic receptor agonist is an alpha or a beta adrenergic agonist or a combination thereof.

In yet another embodiment, the alpha adrenergic agonist is an alpha 1 or alpha 2 adrenergic agonist.

In yet another embodiment, the beta adrenergic agonist is a β2 adrenergic agonist.

In yet another embodiment, the beta adrenergic agonist is selected from the group consisting of isoproterenol, clenbuterol, metaproterenol, albuterol, terbutaline, salmeterol, salbutamine, bitolterol, pirbuterol acetate, formoterol, epinephrine, and norepinephrine.

In yet another embodiment, the mobilizer of stem cells or progenitor cells is selected from the group consisting of a small organic molecule, a polypeptide, a nucleic acid and a carbohydrate.

In yet another embodiment, the small organic molecule is AMD3100 or an analog, derivative or a combination thereof.

In yet another embodiment, the polypeptide is selected from the group consisting of a cytokine, a colony stimulating factor, a protease or a chemokine.

In yet another embodiment, the cytokine is selected from the group consisting of interleukin-1 (IL-1), interleukin-3 (IL-3), interleukin-6 (IL-6), interleukin-11 (IL-11), interleukin-7 (IL-7), and interleukin-12 (IL12).

In yet another embodiment, the colony stimulating factor is selected from the group consisting of granulocyte colony stimulating factor (G-CSF), granulocyte-macrophage colony stimulating factor (GM-CSF), macrophage colony stimulating factor (M-CSF), stem cell factor, FLT-3 ligand or a combination thereof.

In yet another embodiment, the protease is selected from the group consisting of a metalloproteinase (like MMP2 or MMP9) a serine protease, (like cathepsin G, or elastase) a cysteine protease (like cathepsin K) and a dipeptidyl peptidase-1 (DDP-1 OR CD26).

In yet another embodiment, the chemokine is CXCL12, or a chemokine other than CXCL12 selected from the group consisting of IL-8, Mip-1α, and Groβ.

In yet another embodiment, the nucleic acid is a DNA or an RNA molecule.

In yet another embodiment, the nucleic acid is a small interfering RNA (siRNA) molecule or an antisense molecule specific for CXCL12.

In yet another embodiment, the carbohydrate is a sulfated carbohydrate selected from the group consisting of Fucoidan and sulfated dextran.

Other objects and advantages will become apparent to those skilled in the art from a review of the following description which proceeds with reference to the following illustrative drawings.

(H) G-CSF-induced mobilization in C57BL6 mice that received a β-adrenergic antagonist (propranolol). * p<0.05.

(I) Rescue of G-CSF-induced mobilization in Dbh$^{-/-}$ mice treated by administration of a β$_2$-adrenergic agonist (clenbuterol).

Figure 7:
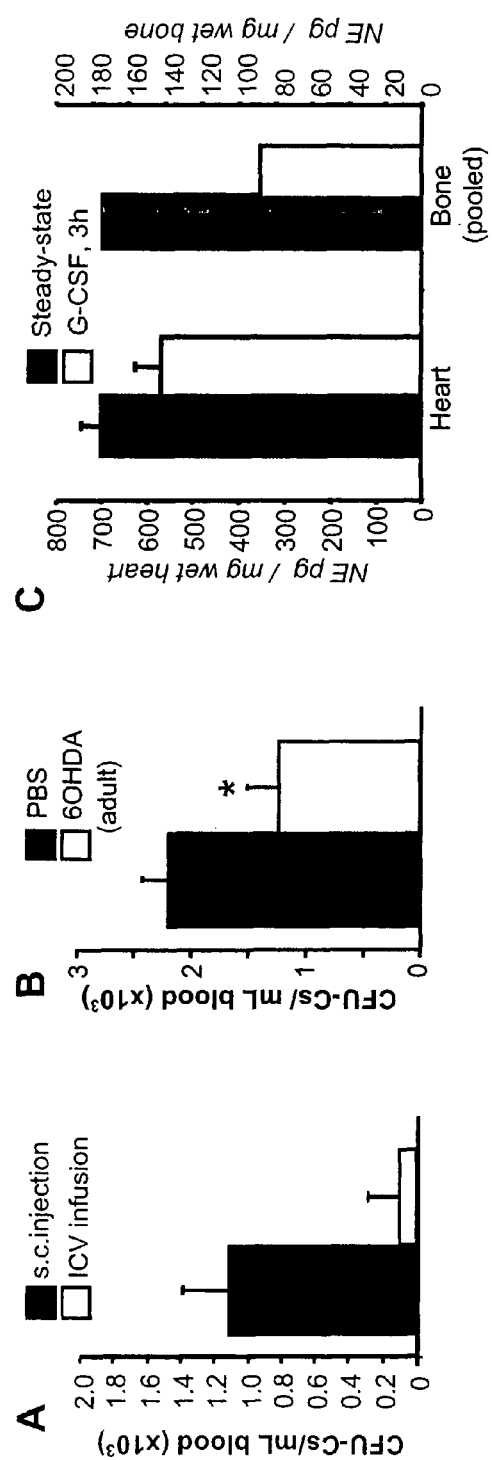
Figure 7:
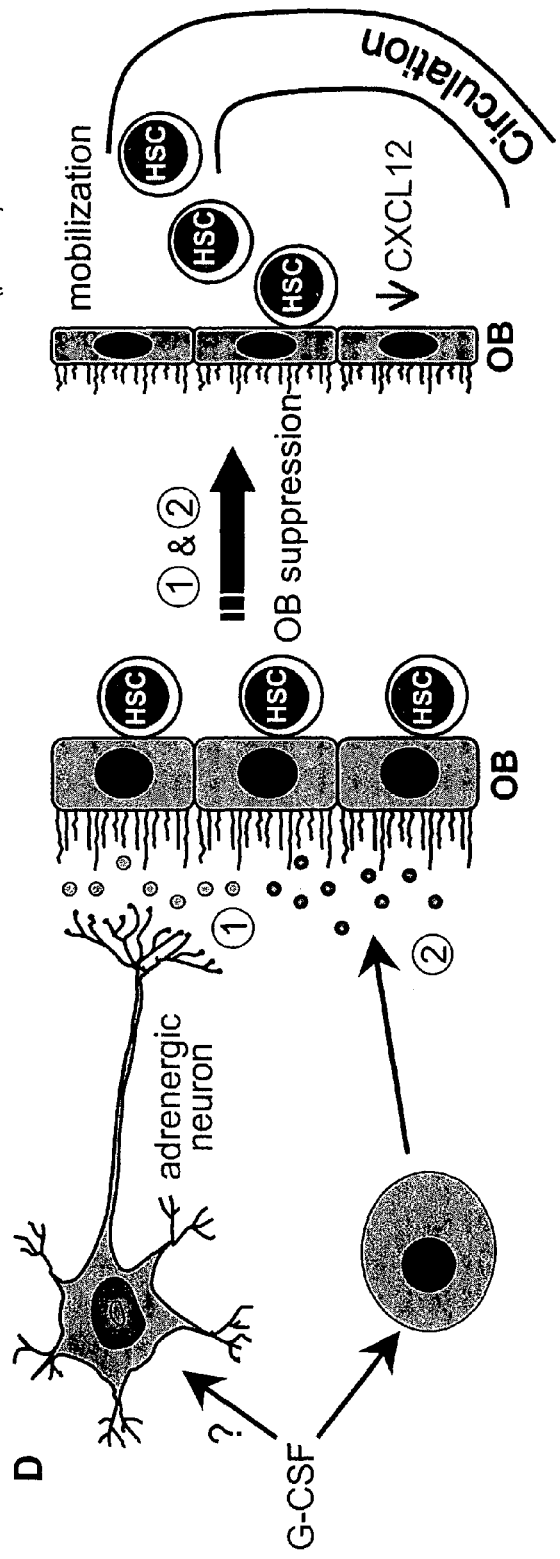

FIG. 7. G-CSF-induced mobilization requires peripheral adrenergic signals and reduces NE content in bone.

(A) Mobilization efficiency when G-CSF is administered directly in the central nervous system though ICV infusion. n=3-4 mice.

(B) G-CSF-induced mobilization in 6OHDA-lesioned adult C57BL/6 mice.

(C) NE content in control or G-CSF-treated (250 μg/kg s.c.) tissues. NE content was determined by HPLC from cardiac and bone (containing BM) tissues. Heart, n=4; bones were pooled from the same 4 mice.

(D) Model for G-CSF-induced HSPC mobilization. G-CSF may activate the outflow of the sympathetic nervous system by influencing directly or indirectly autonomic neurons in sympathetic ganglions in the periphery. Released NE (①) and a yet unidentified signal (②) mediate osteoblast (OB) suppression, thereby reducing the synthesis of CXCL12. Posttranslational mechanisms (degradation/inactivation) may also contribute to lowering CXCL12 levels to those permissive for HSPC egress from their niche. We propose that OB suppression and CXCL12 reduction lead to HSPC mobilization. In addition, it is possible that adrenergic neurotransmission also regulates HSPC mobilization through other mechanisms given the newly identified non-OB stem cell niches (Kiel et al., 2005).

Figure 8:
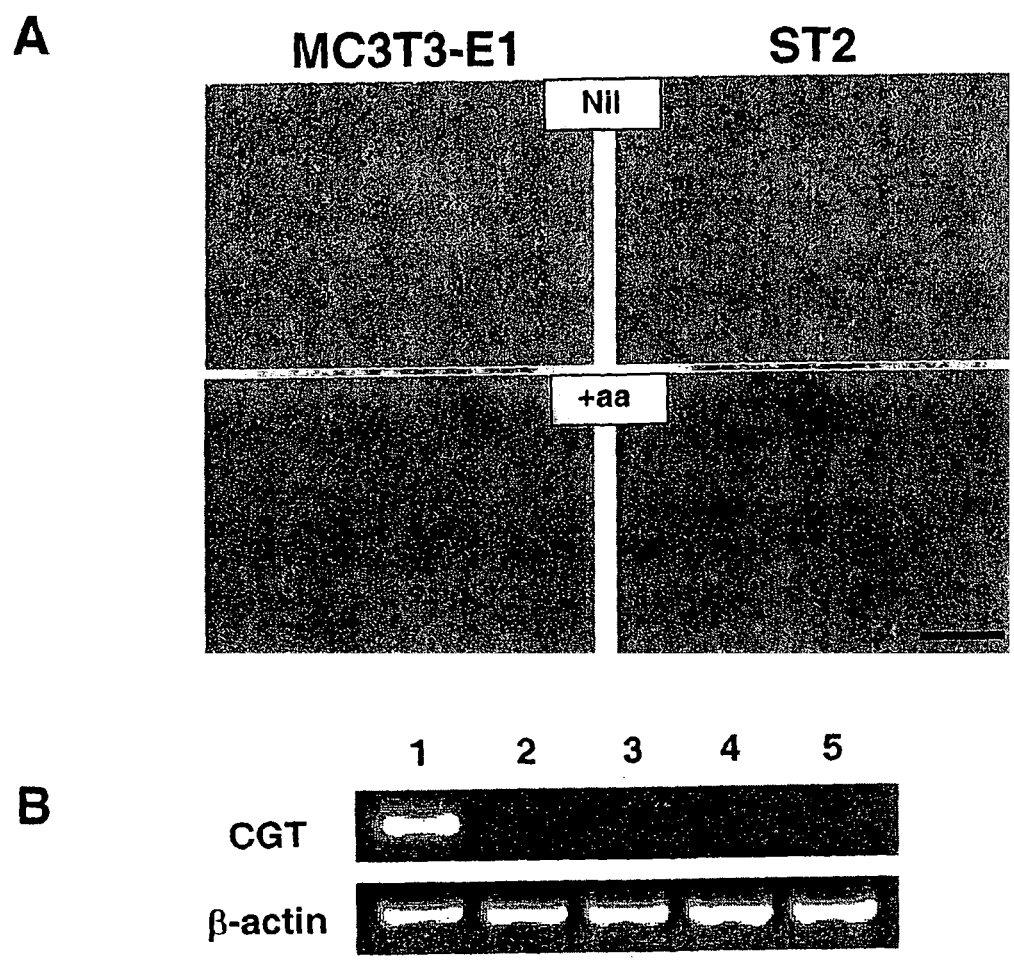

FIG. 8. CGT mRNA expression in differentiated osteoblastic cell lines.

Murine pre-osteoblast (MC3T3-E1) and osteoblast precursor (ST2) cell lines (RIKEN Cell Bank, Tsukuba, Ibaraki, Japan) were cultured in αMEM+10% FBS and RPMI1640+10% FBS, respectively, with or without 50 μg/ml ascorbic acid (+aa, Sigma, St Louis, Mo.) to induce osteoblastic maturation. Half of culture medium was replaced with fresh medium containing ascorbic acid twice a week, and cultures were maintained for 18 days. Alkaline phosphatase (ALP) staining was performed on cultures established on cover slips as described elsewhere with minor modifications (Kato, Y., Windle, J. J., Koop, B. A., Mundy, G. R., and Bonewald, L. F. (1997). Establishment of an osteocyte-like cell line, MLO-Y4. J Bone Miner Res 12, 2014-2023; Tanaka-Kamioka, K., Kamioka, H., R is, H., and Lim, S. S. (1998). Osteocyte shape is dependent on actin filaments and osteocyte processes are unique actin-rich projections. J Bone Miner Res 13, 1555-1568). Briefly, samples were fixed with formalin at room temperature for 10 min followed by the incubation with prewarmed ALP staining solution (0.1 M Tris-HCl (pH 8.9) containing 50 μg/nm Naphthol ASMX phosphate sodium (Sigma), 0.5% N,N-dimethylformamide (Sigma), and 0.6 mg/ml fast red violet LB salt (Sigma)) for 20 min at 37° C.

(A) Note the ALP staining (red) in both cell lines was induced by ascorbic acid, suggesting osteoblastic maturation of these cell lines. Bar: 50 μm. (B) CGT mRNA expression assessed by RT-PCR in these cells. Lane 1: control from mouse brain, 2: MC3T3-E1 (Nil), 3: MC3T3-E1 (+aa), 4: ST2 (Nil), 5: ST2 (+aa). CGT gene expression was not induced by osteoblastic maturation in these cell lines.

Figure 9:
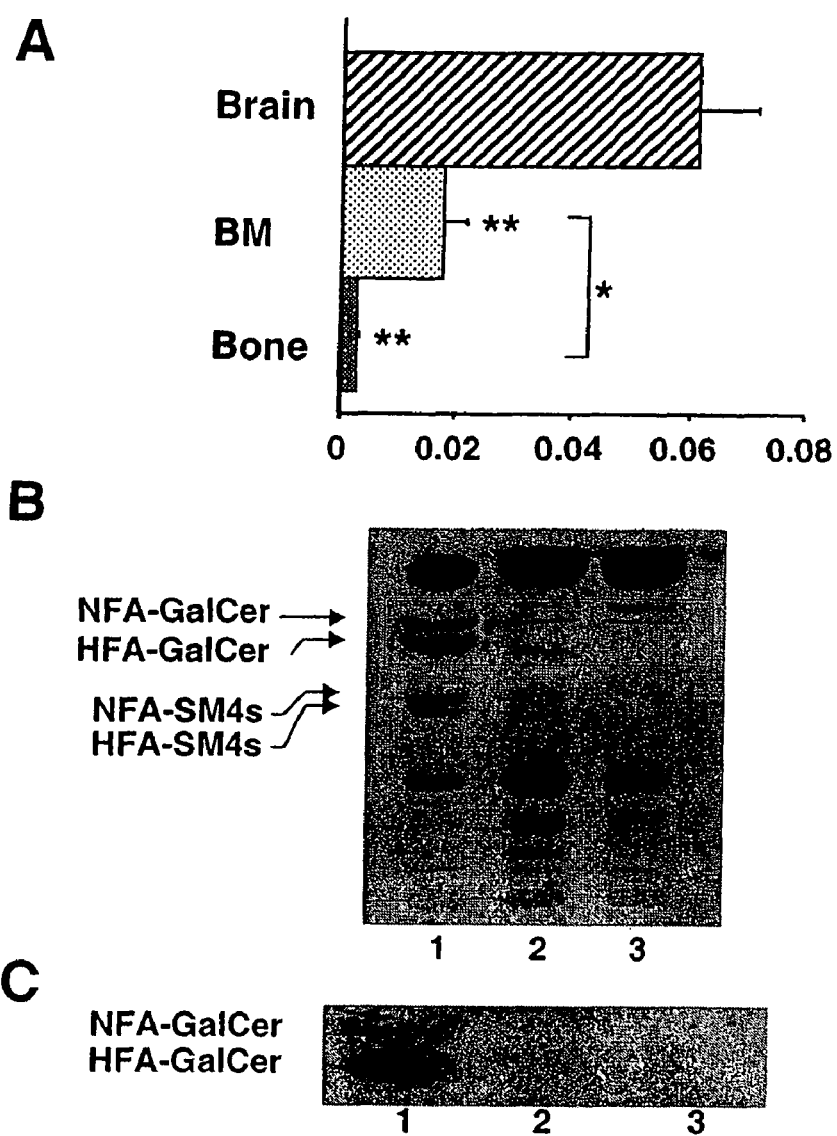

FIG. 9. CGT expression in bone and bone marrow.

(A) Quantification of CGT mRNA expression levels in brain, BM, and bone by real-time RT-PCR. RNA extraction, RT reaction and real-time PCR were performed as described in the Experimental Procedures. All data were normalized to GAPDH. Data were analyzed by one-way ANOVA with Fisher's PLSD post-hoc test. n=3-5, *p<0.05, **p<0.01.

(B) Total lipids were extracted as previously described (Katayama, Y., and Frenette, P. S. (2003). Galactocerebrosides are required postnatally for stromal-dependent bone marrow lymphopoiesis. Immunity 18, 789-800) from lyophilized samples of C57BL/6 mouse brain, bone marrow (BM) cellular contents, or bone powder prepared by pulverizing bone carcass after freezing in liquid nitrogen. Alkali stable lipids from 5 mg brain wet tissue (lane 1), BM cells from 2.5 femurs (lane 2), and 2.5 femoral bones (lane 3) were separated on high performance thin layer chromatography (HPTLC, Silica gel 60, Merck, Darmstadt, Germany) and visualized by orcinol ferric chloride (Sigma) as described (Katayama, Y., and Frenette, P. S. (2003). Galactocerebrosides are required postnatally for stromal-dependent bone marrow lymphopoiesis. Immunity 18, 789-800). NFA, non-hydroxy-fatty acid; HFA, α-hydroxy-fatty acid; GalCer, galactosylceramide; SM4s, sulfatide. (C) To ascertain whether the bands observed in the boxed region were genuine GalCer, Far-eastern blotting was performed as described elsewhere (Ishikawa, D., and Taki, T. (2000). Thin-layer chromatography blotting using polyvinylidene difluoride membrane (far-eastern blotting) and its applications. Methods Enzymol 312, 145-157). Briefly, HPTLC plate was dipped in blotting solution (iso-propanol:methanol:0.2% CaCl$_2$=40:7:20) for 20 s at RT and the bands were transferred to polyvinylidene difluoride (PVDF) membrane (Millipore, Bedford, Mass.) by heating with an iron at 180° C. for 30 s. Membrane was stained with mouse anti-GalCer antibody (Bansal, R., Warrington, A. E., Gard, A. L., Ranscht, B., and Pfeiffer, S. E. (1989). Multiple and novel specificities of monoclonal antibodies O1, O4, and R-mAb used in the analysis of oligodendrocyte development. J Neurosci Res 24, 548-557) (clone O1, R&D systems, Minneapolis, Minn.) followed by HRP-conjugated Donkey anti-mouse IgM (Jackson ImmunoResearch, West Grove, Pa.), and the signal was detected using West Dura Extended Duration Substrate (Pierce, Rockford, Ill.). Control brain revealed strong signals consistent with α-hydroxy-fatty acid and non-hydroxy-fatty acid forms of GalCer, whereas no signal was detected in alkali-stable lipid extracts from BM and bone tissues from 2.5 femurs.

Figure 10:
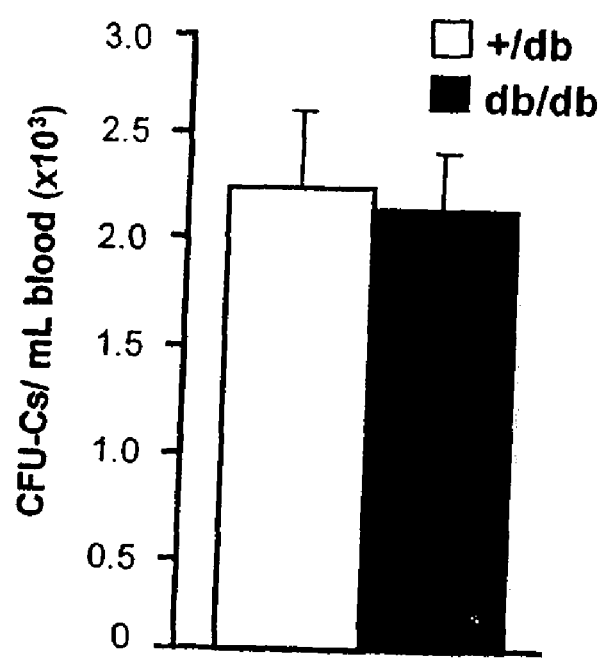

FIG. 10. G-CSF does not require the leptin receptor and initiates mobilization through a cellular target in the periphery.

(A) Leptin receptor deficient and control mice, Lepr(db/db) and Lepr(+/db) (B6.Cg-m+/+Leprdb/J), were purchased from the Jackson laboratory (Bar Harbor, Me. Stock number: 000697). Four week-old Lepr(db/db) and their littermate heterozygotes were treated with PBS/BSA vehicle buffer (open bars) and human G-CSF (250 μg/kg/day) (closed bars). Circulating CFU-Cs were assayed as described in *Experimental Procedures*. There was no difference in the numbers of circulating progenitors between the two groups. n=5 mice per group.

Figure 11:
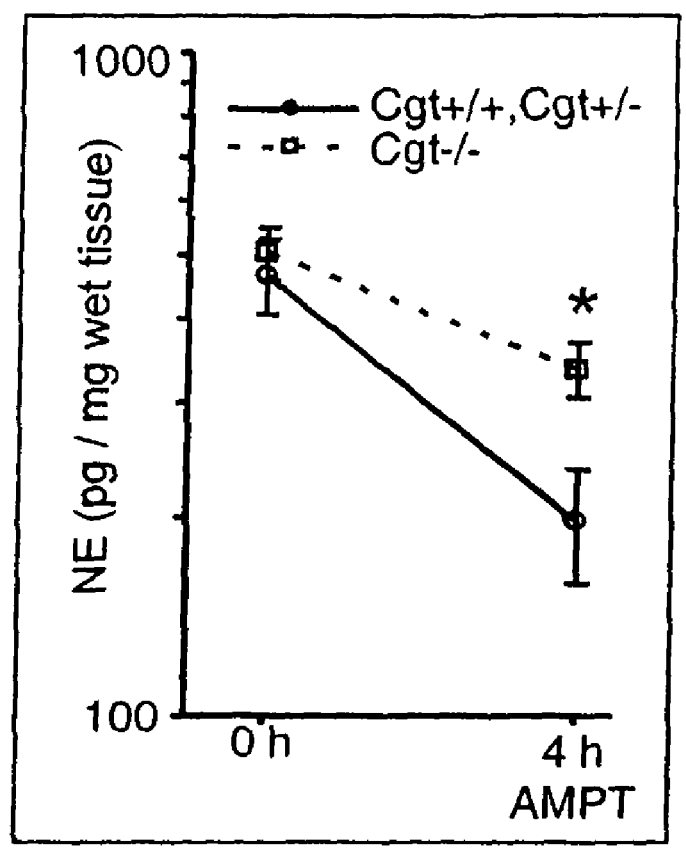

FIG. 11. Norepinephine turnover in tissues following G-CSF administration in Cgt littermates.

To assess turnover rate, Cgt were administered the catecholamine synthesis inhibitor α-methyl-p-tyrosine (AMPT, 300 mg/kg, Sigma) or were left untreated. Animals were sacrificed 4 h after AMPT injection. Hearts were rapidly removed, weighed, frozen in liquid nitrogen and stored at −80° C. for norepinephrine measurements. NE levels were determined by HPLC at the Neurochemistry Core Lab, Vanderbilt University's Center for Molecular Neuroscience Research (Nashville, Tenn.). Under steady-state conditions, the decline of norepinephrine (NE) reflects the synthesis rate and the sympathetic tone. n=4-5 mice per group; * p<0.05. Cgt-/- animals exhibit significantly longer NE turnover (see Table S2 below).

Figure 12:
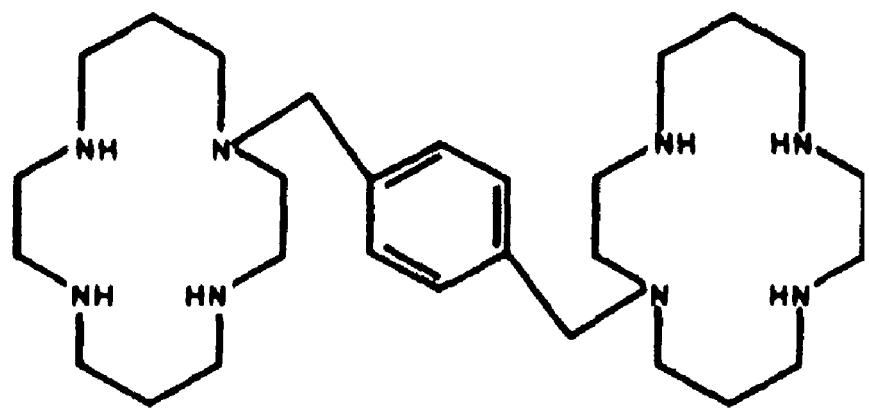

FIG. 12. Structure of AMD-3100

FIG. 12 shows the structure of AMD-3100, also known as 1,1'-[1,4-phenylene-bis(methylene)]-bis(1,4,8,11-tetra-azacyclotetradecane) octahydrochloride dehydrate, which is under development by Anormed, Inc. Other analogs or derivatives of this polyamine molecule may be found in U.S. Pat. Nos. 6,987,102; 5,021,409; 6,001,826; 5,583,131; 5,698,546; 5,817,807, all of which are incorporated herein by reference in their entireties. Also included are PCT publications WO 00/02870; WO 01/44229. Other non-cyclic amines have been disclosed in WO 00/56729; WO 02/22600; WO 02/22599 and WO 02/34745, all of which are incorporated by reference in their entireties.

Figure 13:
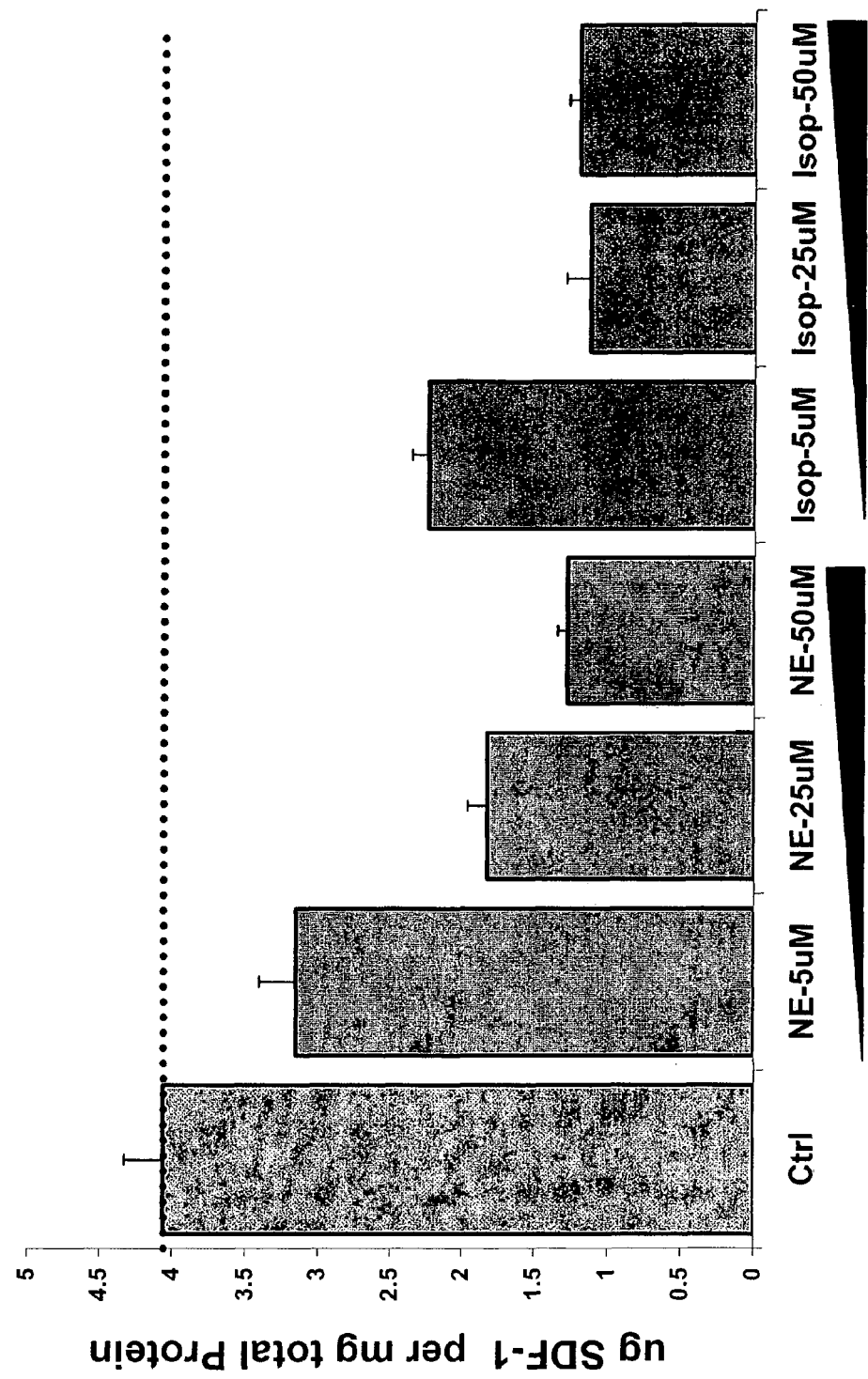

FIG. 13. Norepinephrine decreases SDF-1 secretion by a stromal cell line.

FIG. 13 shows that SDF-1 secretion, as measured by ELISA, decreased in a dose-dependent manner after 72 h exposure of the stromal cell line MS-5 to norepinephrine or to the beta-receptor agonist Isoproterenol. This corresponds with an increase in the stem cell egress.

Figure 14:
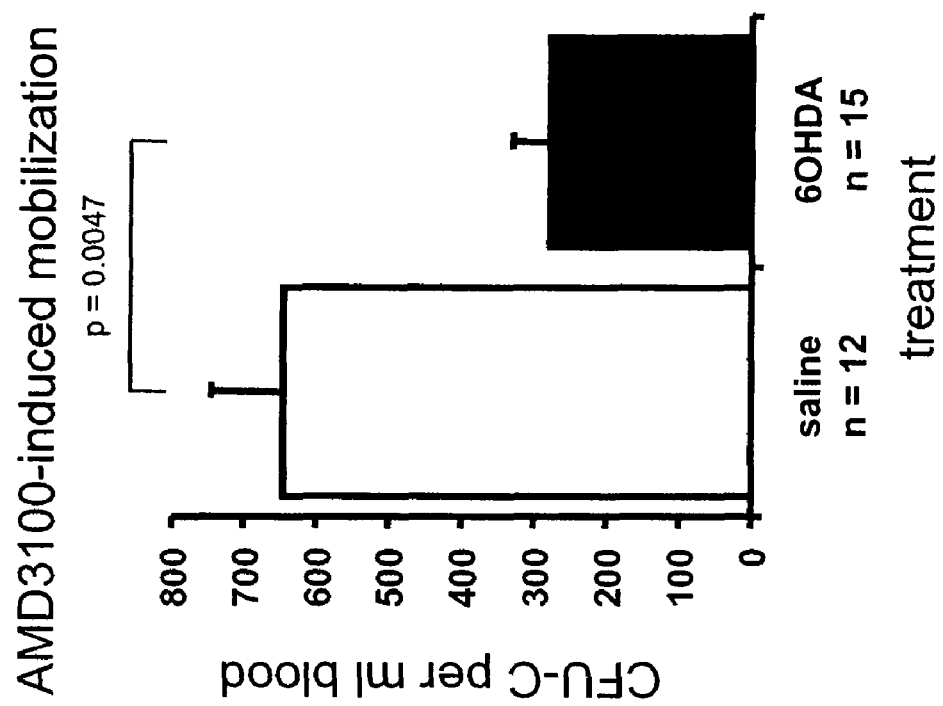

FIG. 14. Stem Cell Egress is Decreased or Reduced in a Dose Dependent Manner

Following Destruction of Dopaminergic and Noradrenergic Neurons

Newborn C57BL6 mice were injected subcutaneously with 6OHDA (100 mg/kg, Sigma) or vehicle (normal saline) on postnatal days 2, 4, 6, 8, and 9. Hematopoietic progenitor mobilization was induced at 34 weeks of age, by subcutaneous injection of AMD3100 (5 mg/kg) in normal saline. Peripheral blood was harvested retroorbitally one hour post injection. P-value was calculated using two-tailed Student's t-test assuming unequal variances.

Figure 15:
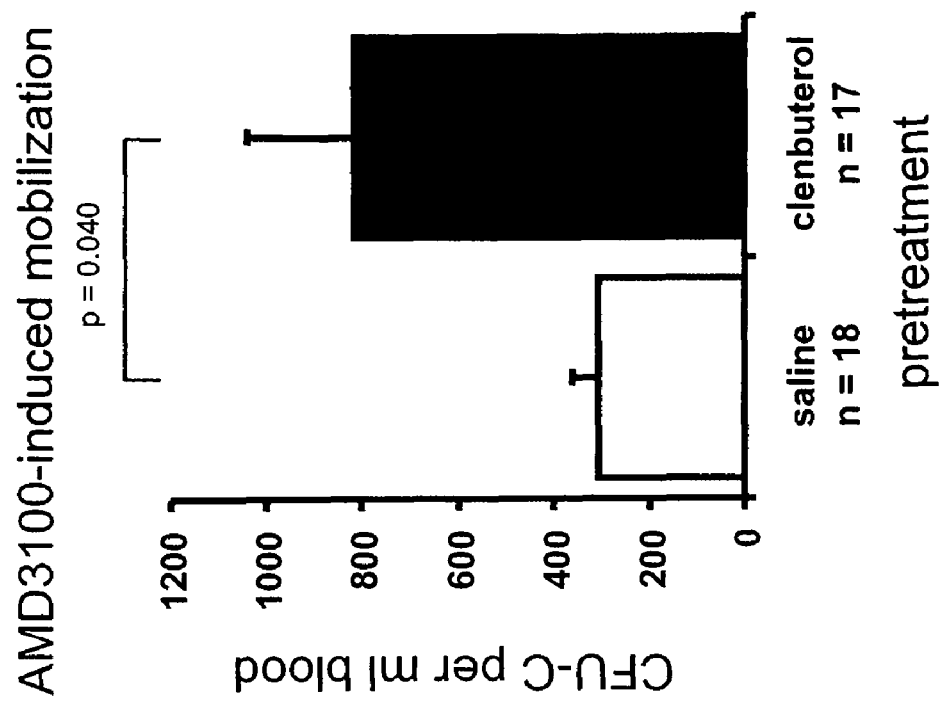

FIG. 15. Enhancement of AMD3100-induced Stem Cell Egress in the Presence of the Beta Agonist Clenbuterol All drugs were dissolved in normal saline (0.9% w/v NaCl), with a delivery volume of 10 µl/g body mass. 10 µl/g saline i.p. or 2 mg/kg clenbuterol i.p. were given to adult (8-10 week old) C57BL6 mice 1 hour prior to hematopoietic progenitor mobilization induced by 5 mg/kg AMD3100 s.c. Peripheral blood was harvested retroorbitally one hour post AMD3100 injection. P-value was calculated using two-tailed Student's t-test assuming unequal variances. The results demonstrate that by using the beta agonist clenbuterol, one can boost stem cell egress in a dose dependent manner.

Figure 16:
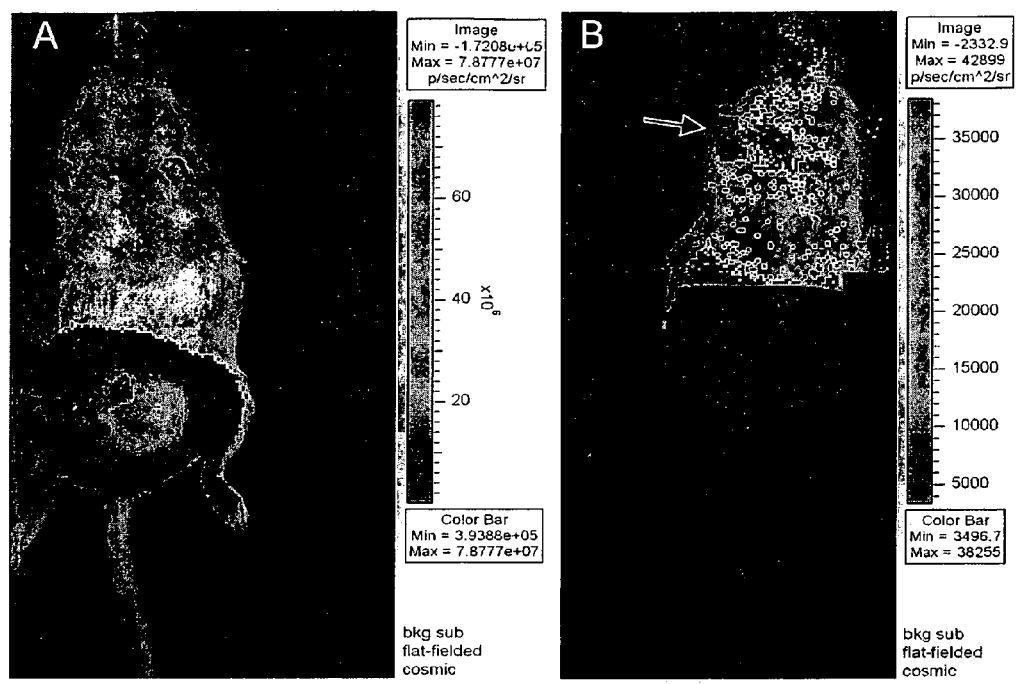

FIG. 16. Bioluminescence detection of human prostate tumors in NOD/SCID mice.

Mice were anesthetized, the prostate was exposed surgically and injected with $1 \times 10^6$ PC3M cells. Bioluminescence imaging was obtained with a Xenogen IVIS 200 following injection of luciferin 150 mg/kg i.p. A) whole body imaging. B) The pelvis was shielded for longer exposure, revealing probable metastases in the right paw (arrow) and mandible.

Figure 17:
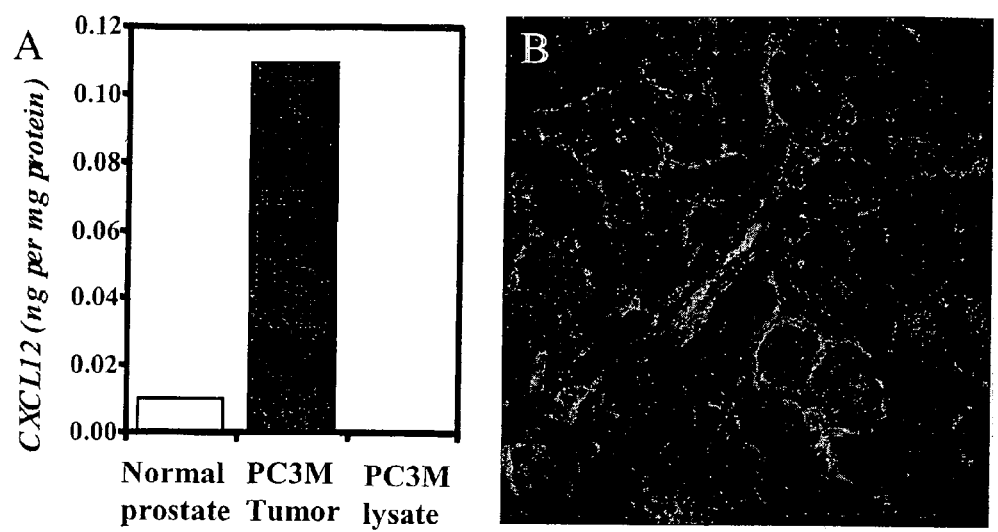

FIG. 17. CXCL12 synthesis and sympathetic innervation in PC3M orthotopic tumors.

A) The prostate tumor from a NOD/SCID mouse shown in FIG. 17A was harvested. Normal prostate tissue was also obtained from an age-matched NOD/SCID mouse. Tissues were homogenized in buffer containing 1% Triton X-100 detergent and protease inhibitors, debris were removed by centrifugation and tissue extracts stored at −80° C. until use. PC3M cells were cultured for 3 days and then lysed in the same buffer as that of tissues. Samples were stored at −80° C. until use. CXCL12 levels were measured by ELISA. n=2 mice for tissues; n=1 for cell culture. B) Frozen section of orthotopic PC3M tumor tissue were stained for CD44 (red) to visualize tumor cells and tyrosine hydroxylase (green, TH) to stain for sympathetic fibers. A TH positive fiber is shown in green. No staining was observed with control antibodies. DAPI (blue) stains DNA.

Figure 18:
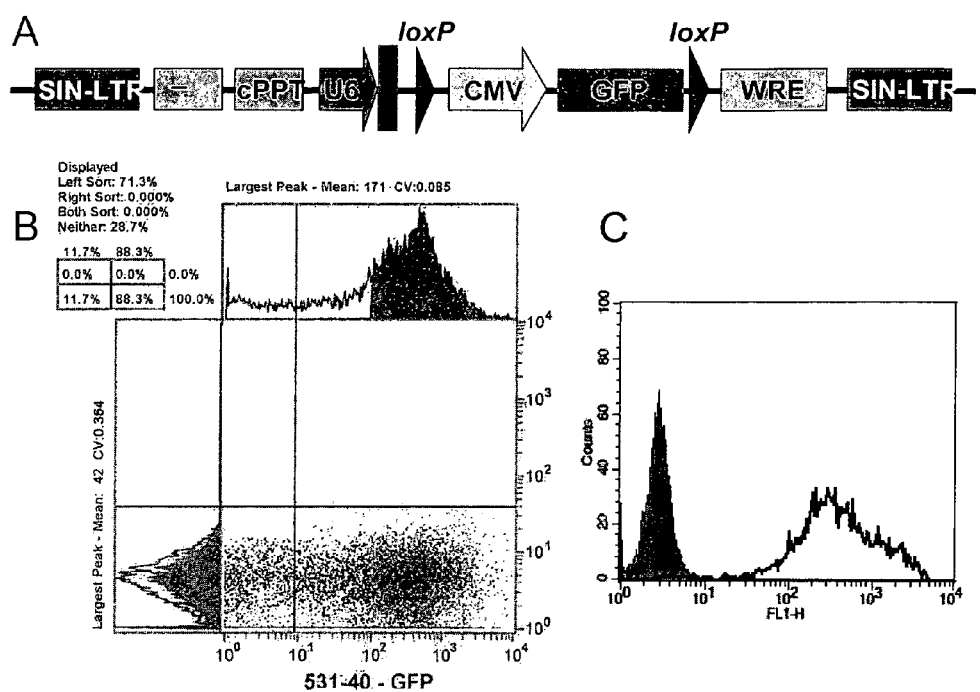

FIG. 18 Generation of PC3 and PC3M cells expressing both the luciferase and the GFP genes.

A) Lentiviral construct containing a GFP cassette under the control of the CMV promoter. The vector also contains a U6 promoter for short hairpin RNA interference experiments proposed in Specific Aim 2. B) PC3luc and PC3Mluc cells ($5 \times 10^5$) were spin-infected (2500 rpm for 90 min at room temperature) with $7.5 \times 10^6$ viral particles in the presence of polybrene (8 ug/ml). The multiplicity of infection (MOI) of this experiment was 15. Cells were then cultured for 3 days before sorting GFP+ cells (green). Sorted cells were expanded in culture and frozen C) GFP is stably expressed. An aliquot of frozen cells was thawed, expanded and analysed by FACS for GFP expression. All PC3MlucGFP cells express strongly GFP. Similar results have been obtained with PC3lucGFP.

DETAILED DESCRIPTION OF THE INVENTION

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth in their entirety.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference I their entireties.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Definitions

The terms used herein have the meanings recognized and known to those of skill in the art, however, for convenience and completeness, particular terms and their meanings are set forth below.

"Agent" refers to all materials that may be used to prepare pharmaceutical and diagnostic compositions, or that may be compounds such as small synthetic or naturally derived organic compounds, nucleic acids, polypeptides, antibodies, fragments, isoforms, variants, or other materials that may be used independently for such purposes, all in accordance with the present invention.

"Agonist" refers to an agent that mimics or up-regulates (e.g., potentiates or supplements) the bioactivity of a protein. An agonist may be a wild-type protein or derivative thereof having at least one bioactivity of the wild-type protein. An agonist may also be a compound that up-regulates expression of a gene or which increases at least one bioactivity of a protein. An agonist may also be a compound which increases the interaction of a polypeptide with another molecule, e.g., a target peptide or nucleic acid.

"Antagonist" refers to an agent that down-regulates (e.g., suppresses or inhibits) at least one bioactivity of a protein. An antagonist may be a compound which inhibits or decreases the interaction between a protein and another molecule, e.g., a target peptide or enzyme substrate. An antagonist may also be a compound that down-regulates expression of a gene or which reduces the amount of expressed protein present.

A "small molecule" refers to a composition that has a molecular weight of less than 3 kilodaltons (kDa), and preferably less than 1.5 kilodaltons, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, and preferably less than 1.5 kilodaltons, and more preferably less than about 1 kDa.

"β-adrenergic receptor antagonists" are a class of drugs that compete with beta-adrenergic agonists for available receptor sites. These compounds are used in the treatment of a variety of cardiovascular diseases where beta-adrenergic blockade is desirable. Antagonists have an intrinsic activity of zero. These agents are also called beta-adrenergic receptor blocking agents, or beta-adrenoreceptor antagonists. They are also known as beta-blockers. Examples of these agents include Acebutolol (N-[3-Acetyl-4-[2-hydroxy-3-[(1-methylethyl)amino]phenyl]butamamide), Atenolol(4-[2-Hydroxy-3-[(1-methylethyl)amino]-propoxy]benzeneacetamide), Betaxolol(1-[4-[2-(cyclopropylmethoxy)ethyl]-phenoxy]-3-[(1-methylethyl)amino]-2-propanolol), Bisoprolol(1-[4-[(2-(1-methylethoxy)ethoxy)methyl]phenoxy]-3-[(1-methylethyl)amino]-2-propanolol), Esmolol (Methyl-4-[2-hydroxy-3-[1-methylethyl)amino]-propoxy]benzenepropanoate), Metoprolol(1-[4-(2-Methoxyethyl)phenoxy]-3-[1-methylethyl)amino]-2-propanol, Carteolol (5-[3-[(1,1-Dimethylethyl)amino]-2-hydroxypropoxy]-3,4-dihydro-2(1H)quinolinone), Nadolol(5-[3-[(1,1-Dimethylethyl)amino]-2-hydroxypropoxy]-1,2,3,4-tetrahydro-2,3-naphthalenediol, Penbutolol(1-(2-Cyclopentylphenoxy)-3-[1,1-dimethylethyl)amino]-2-propanol), Pindolol(1-(1H-Indol-4-yloxy)-3-[1-methylethyl)amino]-2-propanol), Propranolol(1-[(1-Methylethyl)amino]-3-(1-naphthalenyloxy)-2-propanol), Sotalol(N-[4-[1-Hydroxy-2-[(1-methylethyl)amino]ethyl]phenyl]methanesulfonamide), Timolol(1-[(1,1-Dimethylethyl)amino]-3-[[4-morpholinyl-1,2,5-thiadizaol-3-yl]oxy]-2-propanol), Carvedilol(1-(Carbazol-4-yloxy)-3-[[2-(O-methoxyphenoxy)ethyl]amino]2-propanol), Labetalol (2-Hydroxy-5-[1-hydroxy-2-1{(1-methyl-3-phenylpropyl)amino]ethyl]benzamide), Alprenolol(1-[(Methylethyl)amino]-3-[2-(2-propenyl)phenoxy]-2-propanol, and ICI 118,551 ((+/−)-1-[2,3-d]hydro-7-methyl-1H-inden-4-yl)oxy]-3-[(1-methylethyl)amino]-2-butanol hydrochloride) (see U.S. Pat. Nos. 6,410,560 and 4,908,387, incorporated by reference in their entireties.).

The α-adrenergic receptor antagonists that are nitrosated or nitrosylated in accordance with the invention and/or are included in the compositions of the invention can be any of those known in the art, including those exemplified below. Structurally, the .alpha.-antagonists can generally be categorized as haloalkylamines, imidazolines, quinozolines, indole derivatives, phenoxypropanolamines, alcohols, alkaloids, amines, piperizines and piperidines.

The first group of α-antagonists are the haloalkylamines that irreversibly block $\alpha_1$- and $\alpha_2$-adrenergic receptors. Included in this group are, for example, phenoxybenzamine and dibenamine. Phenoxybenzamine is used in the treatment of pheochromocytomas, tumors of the adrenal medulla and sympathetic neurons that secrete catecholamines into the circulation. It controls episodes of severe hypertension and minimizes other adverse effects of catecholamines such as contraction of plasma volume and injury of the myocardium.

Another group of α-antagonists are the imidazolines. These include phentolamine and tolazoline. Phentolamine has similar affinity for $\alpha_1$ and $\alpha_2$ receptors. Phentolamine is used in short-term control of hypertension in patients with pheochromocytoma and direct, intracavernous injection of phentolamine (usually in combination with papaverine) has been proposed as a treatment for male sexual dysfunction. Tolazoline is used in the treatment of persistent pulmonary hypertension in neonates. Other imidazolines include, for example, idazoxan, deriglidole, RX 821002, BRL 44408 and BRL 44409 (see, Young et al, Eur. J. Pharm., 168:381-386 (1989), the disclosure of which is incorporated herein by reference).

Another group of α-antagonist compounds that are contemplated are the quinazolines. These include, for example, prazosine, a very potent and selective $\alpha_1$-adrenergic antagonist, terazosin, doxazosin, alfuzosin, bunazosin, ketanserin, trimazosin and abanoquil. This group of compounds is principally used in the treatment of primary systemic hypertension and also in the treatment of congestive heart failure.

Another class of α-adrenergic blocking agents are indoles and indole derivatives. These include, for example, carvedilol and BAM 1303.

Another class of α-adrenergic blocking agents are alcohols. These include, for example, labetelol and ifenprodil.

Another class of α-adrenergic blocking agents are alkaloids. These include, for example, "ergotoxine" which is a mixture of three alkaloids: ergocornine, ergocristine and ergocryptine. Both natural and dihydrogenated peptide alkaloids produce alpha-adrenergic blockade. The principal uses are to stimulate contraction of the uterus postpartum and to relieve the pain of migraine headaches. Another indole alkaloid is yohimbine. This compound is a competitive antagonist that is selective for $\alpha_2$-adrenergic receptors. In humans, it has been observed to increase blood pressure and heart rate and has been used in the treatment of male sexual dysfunction. Other alkaloid α-blockers include rauwolscine, corynathine, raubascine, tetrahydroalstonine, apoyohimbine, akuammigine, beta-yohimbine, yohimbol, pseudoyohimbine and epi-3 α-yohimbine.

Another class of α-adrenergic blocking agents are amines. These include, for example, tamsulosin, benoxathian, atipamezole, BE 2254, WB 4101 and HU-723.

Another class of α-adrenergic blocking agents are piperizines, which include, for example, naftopil and saterinone.

Another class of α-adrenergic blocking agents are piperidines. These include, for example, haloperidol.

Each of the above contemplated α and β-antagonists is described more fully in the literature, such as in Goodman and Gilman, The Pharmacological Basis of Therapeutics (8th Edition), McGraw-Hill (1990), the disclosure of which is incorporated by reference herein in its entirety.

The concept of "combination therapy" is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g. concurrently, or wherein one of the compounds is administered first, followed by the second agent, e.g. sequentially. The desired result can be either a subjective relief of one or more symptoms or an objectively identifiable improvement in the recipient of the dosage.

"Modulation" or "modulates" or "modulating" refers to up regulation (i.e., activation or stimulation), down regulation (i.e., inhibition or suppression) of a response, or the two in combination or apart.

"Treatment" or "treating" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted. In the present invention, the treatments using the agents described may be provided to treat patients suffering from a cancerous condition or hyperproliferative disease, whereby the treatment of the disease with chemotherapy or irradiation therapy results in a decrease in bone marrow cellularity, thus making the patient more prone to acquiring infectious agents or diseases. Thus, the administration of any of the agents of the invention allows for the mobilization of hematopoietic stem cells or progenitor cells from the bone marrow to the peripheral blood. Most preferably, the treating is for the purpose of reducing or diminishing the symptoms or progression of a cancerous disease or disorder by allowing for the use of accelerated doses of chemotherapy or irradiation therapy.

"Subject" or "patient" refers to a mammal, preferably a human, in need of treatment for a condition, disorder or disease.

"Prophylactic" or "therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "mobilizer of hematopoietic stem cells or progenitor cells" or "mobilizer", (used interchangeably) as described herein refers to any compound, whether it is a small organic molecule, synthetic or naturally derived, or a polypeptide, such as a growth factor or colony stimulating factor or an active fragment or mimic thereof, a nucleic acid, a carbohydrate, an antibody, or any other agent that acts to enhance the migration of stem cells from the bone marrow into the peripheral blood. Such a "mobilizer" may increase the number of hematopoietic stem cells or hematopoietic progenitor/precursor cells in the peripheral blood, thus allowing for a more accessible source of stem cells for use in transplantation.

"Stem Cells" are cells, which are not terminally differentiated and are therefore able to produce cells of other types. Stem cells are divided into three types, including totipotent, pluripotent, and multipotent. "Totipotent stem cells" can grow and differentiate into any cell in the body, and thus can grow into an entire organism. These cells are not capable of self-renewal. In mammals, only the zygote and early embryonic cells are totipotent. "Pluripotent stem cells" are true stem cells, with the potential to make any differentiated cell in the body, but cannot contribute to making the extraembryonic membranes (which are derived from the trophoblast). "Multipotent stem cells" are clonal cells that self-renew as well as differentiate to regenerate adult tissues. "Multipotent stem cells" are also referred to as "unipotent" and can only become particular types of cells, such as blood cells or bone cells. The term "stem cells", as used herein, refers to pluripotent stem cells capable of self-renewal.

"Cancer stem cells" refers to a small population of cells that are quiescent, which are capable of self-renewal, and which appear to be the source of cells comprising a malignant and/or metastatic tumor.

A "niche" refers to a small zone within the microenvironment of a stem cell that maintains and controls stem cell activity in several organs.

"Adult stem cells" can be found in adult beings. Adult stem cells reproduce daily to provide certain specialized cells, for example 200 billion red blood cells are created each day in the body. Until recently it was thought that each of these cells could produce just one particular type of cell. This is called differentiation. However, in the past few years, evidence has been gathered of stem cells that can transform into several different forms. Bone marrow stem cells are known to be able to transform into liver, nerve, muscle and kidney cells. Stem cells isolated from the bone marrow have been found to be pluripotent. Useful sources of adult stem cells are found in organs throughout the body. In the same way that organs can be transplanted from cadavers, researchers have found that these could be used as a source of stem cells as well. Taking stem cells from the brains of corpses they were able to coax them into dividing into valuable neurons.

"Hematopoiesis" refers to the highly orchestrated process of blood cell development and homeostasis. Prenatally, hematopoiesis occurs in the yolk sack, then liver, and eventually the bone marrow. In normal adults it occurs in bone marrow and lymphatic tissues. All blood cells develop from pluripotent stem cells. Pluripotent cells differentiate into stem cells that are committed to three, two or one hematopoietic differentiation pathway. None of these stem cells are morphologically distinguishable, however.

The term "hematopoietic stem cells" as used in the present invention means multipotent stem cells that are capable of differentiating into all blood cells including erythrocytes, leukocytes and platelets. For instance, the "hematopoietic stem cells" as used in the invention are contained not only in bone marrow but also in umbilical cord blood derived cells.

The term "hematopoietic progenitors", which is used interchangeably with the term "hematopoietic precursors", refers to those progenitor or precursor cells which are differentiated further than hematopoietic stem cells but have yet to differentiate into progenitors or precursors of respective blood cell lineages (unipotent precursor cells). Thus, "progenitor cell(s)" or "precursor cell(s)" are defined as cells that are lineage-committed, i.e., an individual cell can give rise to progeny limited to a single lineage such as the myeloid or lymphoid lineage. They do not have self-renewal properties. They can also be stimulated by lineage-specific growth factors to proliferate. If activated to proliferate, progenitor cells have life-spans limited to 50-70 cell doublings before programmed cell senescence and death occurs. For example, the "hematopoietic progenitors" as used in the present invention include granulocyte/macrophage associated progenitors (colony-forming unit granulocyte, macrophage, CFU-GM), erythroid associated progenitors (burst-forming unit erythroid, BFU-E), megakaryocyte associated progenitors (colony-forming unit megakaryocyte, CFU-Mk), and myeloid associated stem cells (colony-forming unit mixed, CFU-Mix). Hematopoietic progenitor cells possess the ability to differentiate into a final cell type directly or indirectly through a particular developmental lineage. Undifferentiated, pluripotent progenitor cells that are not committed to any lineage are referred to herein as "stem cells." All hematopoietic cells can in theory be derived from a single stem cell, which is also able to perpetuate the stem cell lineage, as daughter cells become differentiated. The isolation of populations of mammalian bone marrow cell populations which are enriched to a greater or lesser extent in pluripotent stem cells has been reported (see for example, C. Verfaillie et al., J. Exp. Med., 172, 509 (1990), incorporated herein by reference).

The term "differentiation" of hematopoietic stem cells and/or hematopoietic progenitors as used in the invention means both the change of hematopoietic stem cells into hematopoietic progenitors and the change of hematopoietic progenitors into unipotent hematopoietic progenitors and/or cells having characteristic functions, namely mature cells including erythrocytes, leukocytes and megakaryocytes. Differentiation of hematopoietic stem cells into a variety of blood cell types involves sequential activation or silencing of several sets of genes. Hematopoietic stem cells choose either a lymphoid or myeloid lineage pathway at an early stage of differentiation.

"Clonal progenitors or CFU-c" refers to a colony forming unit culture, in which granulocyte-macrophage progenitor cells are identified by their ability to give rise to monoclonal colonies in the presence of appropriate stimulators in vitro.

"Chemokines" (chemoattractant cytokines) are a family of homologous serum proteins of between 7 and 16 kDa, which were originally characterized by their ability to induce migration of leukocytes. Most chemokines have four characteristic cysteines (Cys), and depending on the motif displayed by the first two cysteines, they have been classified into CXC or alpha, CC or beta, C or gamma, and CX3C or delta chemokine classes. Two disulfide bonds are formed between the first and third cysteines and between the second and fourth cysteines. Clark-Lewis and co-workers reported that, at least for IL-8, the disulfide bridges are critical for chemokine activity (Clark-Lewis et al., J. Biol. Chem. 269:16075-16081, 1994).

The only exception to the four cysteine motif is lymphotactin, which has only two cysteine residues. Thus, lymphotactin retains a functional structure with only one disulfide bond.

In addition, the CXC, or alpha, subfamily has been divided into two groups depending on the presence of the ELR motif (Glu-Leu-Arg) preceding the first cysteine: the ELR-CXC chemokines and the non-ELR-CXC chemokines (see, e.g., Clark-Lewis, supra, and Belperio et al., "CXC Chemokines in Angiogenesis," J. Leukoc. Biol. 68:1-8, 2000). ELR-CXC chemokines, such as IL-8, are generally strong neutrophil chemoattractants while non-ELR chemokines, such as IP-10, and SDF-1, predominantly recruit lymphocytes. CC chemokines, such as RANTES, MIP-1-alpha, MCP-1, generally function as chemoattractants for monocytes, basophils, eosinophils, and T-cells but not neutrophils. In general, chemokines are chemotactic agents that recruit leukocytes to the sites of injuries.

"CXCL12", also known as stromal cell-derived factor-1 or "SDF-1" refers to a CXC chemokine that demonstrates in vitro activity with respect to lymphocytes and monocytes but not neutrophils. It is highly potent in vivo as a chemoattractant for mononuclear cells. SDF-1 has been shown to induce intracellular actin polymerization in lymphocytes, and to induce a transient elevation of cytoplasmic calcium in some cells. By "function of a chemokine, CXCL12" is meant the binding of the chemokine to its receptor and the subsequent effects on signaling. The nucleic acid sequence of the human CXCL12 is shown as SEQ ID NO: 23. It may also be found in the following GenBank Accession numbers: NM_000609; NM_001033886; NM_199168; BC039893; AY644456; AY802782 and CR450283. The protein sequence of the human CXC chemokine, CXCL12 or SDF-1, is shown below as SEQ ID NO:1: Lys-Pro-Val-Ser-Leu-Ser-Tyr-Arg-Cys-Pro-Cys-Arg-Phe-Phe-Glu-Ser-His-Val-Ala-Arg-Ala-Asn-Val-Lys-His-Leu-Lys-Ile-Leu-Asn-Thr-Pro-Asn-Cys-Ala-Leu-Gln-I-le-Val-Ala-Arg-Leu-Lys-Asn-Asn-Asn-Arg-Gln-Val-Cys-Ile-As-p-Pro-Lys-Leu-Lys-Trp-Ile-Gln-Glu-Tyr-Leu-Glu-Lys-Ala-Leu-Asn "Chemokine Receptors" are G-protein coupled seven-transmembrane receptors. Based on the chemokine class they bind, the receptors have been named CXCR1, CXCR2, CXCR3, CXCR4, and CXCR5 (all of which bind CXC chemokines); CCR1 through CCR9 (all of which bind CC chemokines); XCR1 (which binds the C chemokine, Lptn); and CX3CR1 (which binds the CX3C chemokine, fractalkine or neurotactin). Certain "antagonists of CXCR4" have been described in International Publication No. WO 01/85196 A2 entitled "CXCR4 Antagonist Treatment of Hematopoietic Cells" (PCT/CA01/00659. Both PCT publications are hereby incorporated by reference herein, including any drawings, figures and tables. The CXCR4 receptor binds CXCL12. The nucleic acid sequence of human CXCR4 can be found in SEQ ID NO: 24 and also in the following GenBank accession numbers: NM_001008540; Y14739; BC020968; AF052572; and AF025375. The protein sequence of human CXCR4 is shown below as SEQ ID NO: 2: Met Glu Gly Be Ser Ser Ile Pro Leu Pro Leu Leu Gln Ile Tyr Thr Ser Asp Asn Tyr Thr Glu Glu Met Gly Ser Gly Asp Tyr Asp Ser Met Lys Glu Pro Cys Phe Arg Glu Glu Asn Ala Asn Phe Asn Lys Ile Phe Leu Pro Thr Ile Tyr Ser Ile Ile Phe Leu Thr Gly Ile Val Gly-Asn Gly Leu Val Ile Leu Val Met Gly Tyr Gln Lys Lys Leu Arg Ser Met Thr Asp Lys Tyr Arg Leu His Leu Ser Val Ala Asp Leu Leu Phe Val Ile Thr Leu Pro Phe Trp Ala Val Asp Ala Val Ala Asn Trp Tyr Phe Gly Asn Phe Leu Cys Lys Ala Val His Val Ile Tyr Thr Val Asn Leu Tyr Ser Ser Val Leu Ile Leu Ala Phe Ile Ser Leu Asp Arg Tyr Leu Ala Ile Val His Ala Thr Asn Ser Gln Arg Pro Arg Lys Leu Leu Ala Glu Lys Val Val Tyr Val Gly Val Trp Ile Pro Ala Leu Leu Leu Thr Ile Pro Asp Phe Ile
Phe Ala Asn Val Ser Glu Ala Asp Asp Arg Tyr Ile Cys Asp Arg
Phe Tyr Pro Asn Asp Leu Trp Val Val Val Phe Gln Phe Gln His
Ile Met Val Gly Leu Ile Leu Pro Gly Ile Val Ile Leu Ser Cys Tyr Cys Ile Ile Ile Ser Lys Leu Ser His Ser Lys Gly His Gln Lys Arg Lys Ala Leu Lys Thr Thr Val Ile Leu Ile Leu Ala Phe Phe Ala Cys Trp Leu Pro Tyr Tyr Ile Gly Ile Ser Ile Asp Ser Phe Ile Leu Leu Glu Ile Ile Lys Gln Gly Cys Glu Phe Glu Asn Thr Val His Lys Trp Ile Ser Ile Thr Glu Ala Leu Ala Phe Phe His Cys Cys Leu Asn Pro Ile Leu Tyr Ala Phe Leu Gly Ala Lys Phe Lys Thr Ser Ala Gln His Ala Leu Thr Ser Val Ser Arg Gly Ser Ser Leu Lys Ile Leu Ser Lys Gly Lys Arg Gly Gly His Ser Ser Val Ser Thr Glu Ser Glu Ser Ser Ser Phe His Ser Ser

"Analog" as used herein, refers to a chemical compound, a nucleotide, a protein, or a polypeptide that possesses similar or identical activity or function(s) as the chemical compounds, nucleotides, proteins or polypeptides having the desired activity and therapeutic effect of the present invention, but need not necessarily comprise a compound that is similar or identical to those compounds of the preferred embodiment, or possess a structure that is similar or identical to the agents of the present invention.

"Derivative" refers to the chemical modification of molecules, either synthetic organic molecules or proteins, nucleic acids, or any class of small molecules such as fatty acids, or other small molecules that are prepared either synthetically or isolated from a natural source, such as a plant, that retain at least one function of the active parent molecule, but may be structurally different. Chemical modifications may include, for example, replacement of hydrogen by an alkyl, acyl, or amino group. It may also refer to chemically similar compounds which have been chemically altered to increase bioavailability, absorption, or to decrease toxicity. A derivative polypeptide is one modified by glycosylation, pegylation, or any similar process that retains at least one biological or immunological function of the polypeptide from which it was derived.

As used herein, the term "candidate compound" or "test compound" or "test agent" refers to any compound or molecule that is to be tested. As used herein, the terms, which are used interchangeably, refer to biological or chemical compounds such as simple or complex organic or inorganic molecules, peptides, proteins, oligonucleotides, polynucleotides, carbohydrates, or lipoproteins. A vast array of compounds can be synthesized, for example oligomers, such as oligopeptides and oligonucleotides, and synthetic organic compounds based on various core structures, and these are also included in the terms noted above. In addition, various natural sources can provide compounds for screening, such as plant or animal extracts, and the like. Compounds can be tested singly or in combination with one another. Agents or candidate compounds can be randomly selected or rationally selected or designed. As used herein, an agent or candidate compound is said to be "randomly selected" when the agent is chosen randomly without considering the specific interaction between the agent and the target compound or site. As used herein, an agent is said to be "rationally selected or designed", when the agent is chosen on a nonrandom basis which takes into account the specific interaction between the agent and the target site and/or the conformation in connection with the agent's action.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Fucoidan" is a carbohydrate consisting of L-fucose, sulfate and acetate in a molar proportion of 1:1.23:0.36 and can be isolated from the Pacific brown seaweed Fucus evanescens. Fucoidan has been shown to contain a linear backbone of alternating 3- and 4-linked alpha-L-fucopyranose 2-sulfate residues: -->3)-alpha-L-Fucp(2SO(3)(−))-(1-->4)-alpha-L-Fucp(2SO(3)(−))-(1-->. Additional sulfate occupies position 4 in a part of 3-linked fucose residues, whereas a part of the remaining hydroxyl groups is randomly acetylated. (See Bilan, M I, et al., Carbohydrate Research (2002) Apr. 17; 337(8): 719-30).

"Sulfated dextrans" refer to a series of polysaccharides that have variable sulfated patterns. Examples may be found in the following references: Farias et al., J. Biol. Chem. Vol. 275. Issue 38: 29299-29307 (2000); Pomin, V H et al. Glycobiology, 15(12): 1376-1385 (2005); Melo, F R, et al. J. Biol. Chem. 279(2): 20824-20835 (2004)).

RNA interference (RNAi) is an evolutionarily conserved mechanism in plant and animal cells that directs the degradation of messenger RNAs homologous to short double-stranded RNAs termed "small interfering RNA (siRNA)". The ability of siRNA to direct gene silencing in mammalian cells has raised the possibility that siRNA might be used to investigate gene function in a high throughput fashion or to modulate gene expression in human diseases. Methods of preparing siRNAs are known to those skilled in the art. The following references are incorporated herein by reference in their entirety: Reich et al., *Mol. Vis.* 9:210-6 (2003); Gonzalez-Alegre P et al., *Ann Neurol.* 53:781-7 (2003); Miller et al., *Proc Natl Acad Sci USA*. (2003); Bidere et al., *J Biol. Chem.*, published as manuscript M301911200 (Jun. 2, 2003); Van De Wetering et al., EMBO Rep. 4:609-15 (2003); Miller and Grollman, *DNA Repair* (*Amst*) 2:759-63 (2003); Kawakami et al., *Nat Cell Biol.* 5:513-9 (2003); Abdelrahim et al., *Mol. Pharmacol.* 63:1373-81 (2003); Williams et al., *J Immunol.* 170:5354-8 (2003); Daude et al., *J Cell Sci.* 116:2775-9 (2003); Jackson et al., *Nat. Biotechnol.* 21:635-7 (2003); Dillin, *Proc Natl Acad Sci USA*. 100:6289-91 (2003); Matta et al., *Cancer Biol Ther.* 2:206-10 (2003); Wohlbold et al., Blood. (2003); Julien and Herr, *EMBO J.* 22:2360-9 (2003); Scherr et al., *Cell Cycle.* 2:251-7 (2003); Giri et al., *J Immunol.* 170:5281-94 (2003); Liu and Erikson, *Proc Natl Acad Sci USA*. 100:5789-94 (2003); Chi et al., *Proc Natl Acad Sci USA*. 100:6343-6 (2003); Hall and Alexander, *J Virol.* 77:6066-9 (2003).

General Description

The invention relates to the unexpected finding that the use of an adrenergic receptor agonist in combination with an agent that mobilizes hematopoietic stem cells or progenitor cells results in enhanced mobilization of the hematopoietic stem cells or progenitor cells from the bone marrow to the peripheral blood. In one embodiment, the agents that mobilize the hematopoietic stem cells or progenitors may act to decrease the expression or function of a chemokine (the function being the binding of the chemokine to its receptor and further signaling), particularly CXCL12. Alternatively, in another embodiment, the agents that mobilize the hematopoietic stem cells or progenitors may act to block or antagonize the chemokine receptor, CXCR4. In yet another embodiment, the agents that mobilize the hematopoietic stem cells or progenitor cells may act via an as yet unidentified mechanism. As such, the combination of these agents with an adrenergic receptor agonist may be used to treat a subject having cancer and who has undergone or is planning to undergo chemotherapy or irradiation therapy for a cancerous condition, whereby the subject will have reduced bone marrow cellularity due to the treatment regimen. As such, the combination of the adrenergic receptor agonists of the invention, when combined with, for example, a mobilizing therapy such as a colony stimulating factor like G-CSF, would be of significant value if it would allow for the use of lower levels of the colony stimulating factor, thus resulting in significant cost reduction to the patient, as well as perhaps, shortened hospital stays. Additionally, the methods of the present invention would allow for mobilization of the hematopoietic stem cells from the bone marrow to the circulation, thus allowing for collection of these cells from the patient prior to the onset of, for example, chemotherapy, to be administered back to the patient for autologous transplant.

It is known in the art that several other factors act to increase white blood cells and/or hematopoietic stem cells or progenitor cells in both human and animal subjects. These include granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein (MIP), stem cell factor, thrombopoietin and growth related oncogene, as single agents or in combination (Dale, D., et al., *Am. J. of Hematol.* (1998) 57:7-15; Rosenfeld, C., et al., *Bone Marrow Transplantation* (1997) 17:179-183; Pruijt, J., et al., *Cur. Op. in Hematol.* (1999) 6:152-158; Broxmeyer, H., et al., *Exp. Hematol.* (1995) 23:335-340; Broxmeyer, et al., *Blood Cells, Molecules and Diseases* (1998) 24:14-30; Glaspy, J., et al., *Cancer Chemother. Pharmacol.* (1996) 38 (suppl): S53-S57; Vadhan-Raj, S., et al., *Ann. Intern. Med.* (1997) 126:673-81; King, A., et al., *Blood* (2001) 97:1534-1542; Glaspy, J., et al., *Blood* (1997) 90:2939-2951). However, while these agents are effective, there are known disadvantages to their use. For example, since many of these agents/growth factors are proteins, the effort put into the cloning, purification/isolation, in addition to the cost to the patient, sets the stage for searching for small molecule mimics that would be easier to manufacture and less costly for the patient in need of such therapy.

Accordingly, a treatment modality that enhances the stem and/or progenitor cells in blood is helpful in treatments to ameliorate the effects of standard protocols that adversely affect the bone marrow, such as chemotherapy or irradiation therapy that results in leukopenia. The combination of compounds proposed by the present invention may also enhance the success of bone marrow transplantation, and may also combat infections in the patient undergoing such therapies. The combination of compounds proposed are used to mobilize and harvest hematopoietic stem cells or progenitor cells via apheresis and the harvested cells are used in treatments requiring stem cell transplantations. Furthermore, the combination of one or more adrenergic receptor agonists with one or more mobilizing agents can be used both in vivo to promote mobilization of hematopoietic stem cells or progenitor cells from the bone marrow to the peripheral blood or can be used for ex vivo studies, whereby a patient's own stem cells are removed and expanded in culture for autologous transplants. Also contemplated by the present invention are in vitro screens, whereby candidate or test compounds can be measured for their effects on mobilization before being administered in vivo.

The present invention initially hypothesized that sulfatide contributed to the signals mediating HSPC mobilization. During the course of these studies, it was determined that that $Cgt^{-/-}$ mice exhibit defects in postnatal lymphopoiesis owing to specific deficits in stromal elements that support the growth and differentiation of lymphoid precursors (Katayama, Y., and Frenette, P. S. (2003). Galactocerebrosides are required postnatally for stromal-dependent bone marrow lymphopoiesis. Immunity 18, 789-800). Included in the studies presented herein are results showing that $Cgt^{-/-}$ mice fail to mobilize bone marrow (BM) hematopoietic stem cells/progenitor cells (HSPCs) following G-CSF stimulation. Unexpectedly, the deficit is not due to the absence of BM sulfatide, but likely originates from altered neural influence on osteoblasts. The studies presented herein demonstrate that signals emanating from the sympathetic nervous system suppress osteoblast function, and control the attraction of stem cells to their niche.

While the present invention relates primarily to promoting egress or mobilization of hematopoietic stem cells from their niche in the bone marrow to the peripheral circulation, it is proposed that the same mechanisms may be involved in the egress of cancer stem cells from their niche into the circulation, lymphatic system or to distant organs and tissues, thus exacerbating the metastatic process. Thus, the use of a small organic molecule or an antibody to CXCL12 or CXCR4, or an antisense molecule or a small interfering nucleic acid molecule, such as a siRNA (small interfering RNA) or shRNA (short hairpin RNA) that inhibits the expression or function of CXCL12 or CXCR4 may be useful only when combined with treatment with an anti-cancer drug or with irradiation therapy for the reasons discussed below.

The current view of others is that the inhibition of the CXCL12 receptor, CXCR4, can prevent metastasis and clinical trials are underway to address this issue. However, based on the studies presented herein, it is proposed that if the egress of cancer stem cells is under the same or similar regulatory control as other (non-cancer) stem cells, such as hematopoietic stem cells, CXCR4 inhibition may actually mobilize cancer stem cells from their niche in the microenvironment, or in the tumor cell itself, and may paradoxically lead to increased metastasis. Thus, it may be that while this strategy may be useful in the treatment of cancer, it may be essential to combine this therapy with administration of a chemotherapeutic drug or irradiation therapy, as proposed herein. Inhibition or blocking of the expression or function of CXCL12 or CXCR4 may elevate the cancer stem cell from a state of quiescence to an activated or actively proliferating mode, thus also increasing their sensitivity to therapeutic drugs or treatments that target actively dividing cells. Thus, the need for combined therapy using a stem cell mobilizer with anti-cancer drugs or radiation therapy is proposed. Moreover, as demonstrated herein, the mobilization of stem cells appears to be optimized when an alpha or beta adrenergic agonist is combined with a stem cell mobilizer. Thus, in another embodiment, it is envisioned that the alpha or beta adrenergic agonist may be used together with a stem cell mobilizer to optimize the egress of cancer stem cells from their niche in the microenvironment, which may bring them from a quiescent state to an actively dividing state, thus making them more sensitive to chemotherapy or irradiation therapy, which may target actively dividing cells.

Furthermore, the studies presented herein suggest that adrenergic signaling contributes to reducing the synthesis of CXCL12 by stromal cells, and as such, may promote the release of tumor cells, in particular, prostate tumor cells into the circulation. Thus, it is suggested by the studies presented herein that the use of an alpha or beta adrenergic antagonist, when used alone or when combined with chemotherapy or irradiation therapy, may be useful for treating patients suffering from a cancerous condition.

Methods for Treating Cancer

It is proposed that the methods of the invention may be applicable not only for use in enhancing mobilization of hematopoietic stem cells, but may also be applicable for treating cancers, for example, carcinomas, including but not limited to, breast or prostate cancer. Prostate cancer is the most common malignancy of males, affecting one male in nine over 65 years of age (Penson, D. F., and Albertsen, P. C. (2002). Lessons learnt about early prostate cancer from large scale databases: population-based pearls of wisdom. Surg Oncol 11, 3-11). Despite enormous advances in our understanding of the biology and the therapy of the disease, the high incidence of distant metastases remains the leading cause of death. Therefore new avenues to prevent the occurrence of metastasis may have a profound clinical impact in the management of prostate cancer.

Cancer cells exhibit traits common with healthy mammalian cells in that they have a molecular machinery regulating their growth, differentiation and death similar to their normal counterparts (Hanahan, D., and Weinberg, R. A. (2000). The hallmarks of cancer. Cell 100, 57-70). Recent studies using xenograft assays have suggested that tumor tissues contain a rare sub-population of cells reminiscent of normal stem cells that can self-renew and initiate the formation of identical tumors in immunodeficient recipients. Several observations suggest remarkable parallels between normal stem cells and tumorigenic "stem" cells. Examples include their extensive proliferative potential, their ability to give rise to new tissues, and the heterogeneous cellular composition (different phenotypic characteristics and proliferative potentials) of normal and tumor tissues (Reya, T., Morrison, S. J., Clarke, M. F., and Weissman, I. L. (2001). Stem cells, cancer, and cancer stem cells. Nature 414, 105-111). Since this phenomenon is used clinically to harvest stem cells for transplantation, a better understanding of the mechanisms involved in stem cell trafficking is clinically important. Our recent studies suggest that signals from the sympathetic nervous system are critical to alter the function of stromal cells forming the hematopoietic stem cell niche and that this leads to reduced attraction and egress of HSCs from the bone marrow. The studies presented herein propose that prostate tumor-initiating cells (PTICs) share common mechanisms with normal stem cells to egress from the primary tumor and metastasize to distant sites. We propose to test the possibility that analogous signals from the nervous system play similar roles in the development of metastasis of PTICs.

Cancer Stem Cells

Although metastasis is by far the most common cause of death in cancer patients, it is relatively rare, considering the tumor cell burden. Multiple studies have shown that metastatic clones are rare cellular variants of the primary tumor, suggesting that metastasis may arise from two possible non-mutually exclusive scenarios: one possibility is that all cancer cells have an equal, but very low, probability of proliferating and giving rise to distant metastasis (stochastic model), and the other possibility is that only a small definable subset of cells—a cancer stem cell—within the tumor is responsible for the growth and propagation of the cancer. It has been known for many years that only a minority of cancer cells has the capacity to form new tumors and proliferate extensively. For example, only a small cell fraction of cancers cells can form colonies in vitro (Hamburger, A. W., and salmon, S. E. (1977). Primary bioassay of human tumor stem cells. Science 197, 461-463). To prove the presence of cancer stem cells, one had to isolate prospectively the fraction containing the ability to reconstitute tumors. This feat was first accomplished by Dick and colleagues who showed that a small subset of acute myeloid leukemia cells, expressing the same phenotype as normal HSCs (CD34+CD38−), possessed clonogenic activity and the ability to transmit leukemia to immunodeficient animals (Bonnet, D., and Dick, J. E. (1997). Human acute myeloid leukemia is organized as a hierarchy that originates from a primitive hematopoietic cell. Nat Med 3, 730-737). Since then, tumor-initiating stem cells have also been identified in solid tumors such as mammary (Al-Hajj, M., Wicha, M. S., Benito-Hernandez, A., Morrison, S. J., and Clarke, M. F. (2003). Prospective identification of tumorigenic breast cancer cells. Proc Natl Acad Sci USA 100, 3983-3988), brain (Singh, S. K., Hawkins, C., Clarke, I. D., Squire, J. A., Bayani, J., Hide, T., Henkelman, R. M., Cusimano, M. D., and Dirks, P. B. (2004). Identification of human brain tumour initiating cells. Nature 432, 396-401), lung (Kim, C. F., Jackson, E. L., Woolfenden, A. E., Lawrence, S., Babar, I., Vogel, S., Crowley, D., Bronson, R. T., and Jacks, T. (2005). Identification of bronchioalveolar stem cells in normal lung and lung cancer. Cell 121, 823-835) and prostate (Collins, A. T., Berry, P. A., Hyde, C., Stower, M. J., and Maitland, N. J. (2005). Prospective identification of tumorigenic prostate cancer stem cells. Cancer Res 65, 10946-10951).

The presence of stem cells in the prostate has been suggested many years ago from castration studies which led to the rapid involution of the gland, followed by complete regeneration when androgen levels were restored. The fact that such cycle of involution and regeneration could be repeated several times strongly suggested the presence of prostate stem cells (Isaacs, J. T., Schulze, H., and Coffey, D. S. (1987). Development of androgen resistance in prostatic cancer. Prog Clin Biol Res 243A, 21-31). A candidate human prostate cancer stem cell has recently been identified by the expression of CD133 (prominin) and $\alpha 2 \beta 1$ integrin (Richardson, G. D., Robson, C. N., Lang, S. H., Neal, D. E., Maitland, N. J., and Collins, A. T. (2004). CD133, a novel marker for human prostatic epithelial stem cells. J Cell Sci 117, 3539-3545). Interestingly, CD 133 has previously been shown to be a marker for HSCs and neural stem cells, suggesting a conserved genetic program of stem cells amongst tissues and between healthy and cancerous stem cells. Consistent with this possibility, Sca-1, a well-established marker for murine HSCs, was recently shown to identify stem cells in the mouse prostate (Burger, P. E., Xiong, X., Coetzee, S., Salm, S. N., Moscatelli, D., Goto, K., and Wilson, E. L. (2005). Sca-1 expression identifies stem cells in the proximal region of prostatic ducts with high capacity to reconstitute prostatic tissue. Proc Natl Acad Sci USA 102, 7180-7185; Xin, L., Lawson, D. A., and Witte, O. N. (2005). The Sca-1 cell surface marker enriches for a prostate-regenerating cell subpopulation that can initiate prostate tumorigenesis. Proc Natl Acad Sci USA 102, 6942-6947).

Another similarity between cancer cells and hematopoietic stem cells (HSCs) is the expression of the chemokine receptor CXCR4, the cognate receptor of CXCL12. While the role of CXCL12 for HSC homing to and migration out from the bone marrow has been clearly demonstrated, the CXCR4-CXCL12 axis may also play an important role in carcinoma metastasis (Burger, J. A., and Kipps, T. J. (2006). CXCR4: A key receptor in the cross talk between tumor cells and their microenvironment. Blood 107, 1768-1775). For example, prostate cancer cells also express CXCR4 and inhibition of its ligand CXCL12 has been shown to reduce the occurrence of bone metastasis (Razrnkhah, M., Talei, A. R., Doroudchi, M., Khalili-Azad, T., and Ghaderi, A. (2005). Stromal cell-derived factor-1 (SDF-1) alleles and susceptibility to breast carcinoma. Cancer Lett 225, 261-266.; Sun, Y. X., Wang, J., Shelburne, C. E., Lopatin, D. E., Chinnaiyan, A. M., Rubin, M. A., Pienta, K. J., and Taichman, R. S. (2003). Expression of CXCR4 and CXCL12 (SDF-1) in human prostate cancers (PCa) in vivo. J Cell Biochem 89, 462-473; Taichman, R. S., Cooper, C., Keller, E. T., Pienta, K. J., Taichman, N. S., and McCauley, L. K. (2002). Use of the stromal cell-derived factor-1/CXCR4 pathway in prostate cancer metastasis to bone. Cancer Res 62, 1832-1837). However, the effect of CXCR4-CXCL12 inhibition on metastasis has largely been demonstrated using in vitro migration studies or in vivo models in which tumor cells are injected either intravenously or through the left ventricle of the heart. These results have shown clearly that the inhibition of CXCR4 reduced cancer cell migration but these model systems have bypassed the critical early steps in which tumor cells egress from the primary tumor. It is proposed herein that the downregulation of the CXCL12 chemokine, in part through signals from the sympathetic nervous system, represents a critical first step contributing to the egress of PTICs. Careful evaluation of this hypothesis is critical; although the inhibition of CXCR4 or CXCL12 may block seeding of intravenously injected tumors cells, it could also mobilize tumor cells from the primary tumor. Thus, there is the possibility that the mechanisms regulating the retention of PTICs in the tumor microenvironment are similar to those regulating the retention of HSCs in the bone marrow microenvironment.

Mechanisms Regulating the Retention and Egress of HSCs:

HSCs reside in specific niches that regulate their survival, proliferation, self-renewal or differentiation in the BM. The concept of microenvironments supporting the self-renewal of stem cells and differentiation toward specific lineages was introduced more than 35 years ago (Trentin, J. J., Curry, J. L., Wolf, N., and Cheng, V. (1968). Factors controlling stem cell differentiation and proliferation: the hemopoietic inductive microenvironment., In The Proliferation and Spread of Neoplastic Cells. (Baltimore: Williams & Wilkins Co), pp. 713-731). Schofield first coined the term "niche" to describe specific areas where stem cells can self-renew (Schofield, R. (1978). The relationship between the spleen colony-forming cell and the haemopoietic stem cell. Blood Cells 4, 7-25). Using confocal microscopy imaging with lineage staining and BrdU retention, studies have shown that quiescent stem cells closely associate with spindle-shaped N-cadherin-expressing osteoblasts that line the endosteal bone (Arai, F., Hirao, A., Ohmura, M., Sato, H., Matsuoka, S., Takubo, K., Ito, K., Koh, G. Y., and Suda, T. (2004). Tie2/angiopoietin-1 signaling regulates hematopoietic stem cell quiescence in the bone marrow niche. Cell 118, 149-161; Calvi, L. M., Adams, G. B., Weibrecht, K. W., Weber, J. M., Olson, D. P., Knight, M. C., Martin, R. P., Schipani, E., Divieti, P., Bringhurst, F. R., et al. (2003). Osteoblastic cells regulate the haematopoietic stem cell niche. Nature 425, 841-846; Zhang, J., Niu, C., Ye, L., Huang, H., He, X., Tong, W. G., Ross, J., Haug, J., Johnson, T., Feng, J. Q., et al. (2003). Identification of the haematopoietic stem cell niche and control of the niche size. Nature 425, 836-841). Consistent with a role for the osteoblast in the maintenance of hematopoiesis, their ablation using a thymidine kinase suicide approach produced a dramatic loss in BM cellularity upon ganciclovir administration (Visnjic, D., Kalajzic, Z., Rowe, D., Katavic, V., Lorenzo, J., and Aguila, H. L. (2004). Hematopoiesis is severely altered in mice with an induced osteoblast deficiency. Blood). However, a recent study using novel stem cell markers (CD150+ CD48−) has also localized stem cells in association with sinusoidal endothelium, indicating the presence of more than one stem cell niche in the bone marrow (Kiel, M. J., Yilmaz, O. H., Iwashita, T., Terhorst, C., and Morrison, S. J. (2005). SLAM family receptors distinguish hematopoietic stem and progenitor cells and reveal endothelial niches for stem cells. Cell 121, 1109-1121).

In normal individuals, the continuous trafficking of HSCs between the BM and blood compartments likely fills empty or damaged niches and contributes to the maintenance of normal hematopoiesis (Abkowitz, J. L., Robinson, A. E., Kale, S., Long, M. W., and Chen, J. (2003). Mobilization of hematopoietic stem cells during homeostasis and after cytokine exposure. Blood 102, 1249-1253; Wright, D. E., Wagers, A. J., Gulati, A. P., Johnson, F. L., and Weissman, I. L. (2001). Physiological migration of hematopoietic stem and progenitor cells. Science 294, 1933-1936). The phenomenon can be enhanced using several agonists, of which the hematopoietic cytokine granulocyte colony-stimulating factor (G-CSF) is the most commonly used in the clinic to harvest "mobilized" stem cells for transplantation. It has been postulated that G-CSF triggers the release of specific proteases in the BM, leading to the degradation of adhesion molecules and chemokines. In particular, the chemokine CXCL12, also named stromal-derived factor-1 (SDF-1), and its cognate receptor CXCR4 have been implicated as key ligand-receptor pair responsible for the retention of HSCs in the BM (Papayannopoulou, T. (2004). Current mechanistic scenarios in hematopoietic stem/progenitor cell mobilization. Blood 103, 1580-1585). However, mice deficient in several of these proteases exhibit normal egress of HSCs, suggesting that other mechanisms must be involved.

We have shown that the sulfated fucose polymer fucoidan can rapidly elicit HSC mobilization (Frenette, P. S., and Weiss, L. (2000). Sulfated glycans induce rapid hematopoietic progenitor cell mobilization: evidence for selectin-dependent and independent mechanisms. Blood 96, 2460-2468.). We were intrigued by the similar biological characteristics of fucoidan, which is synthesized by certain seaweeds, and sulfatide, a sulfated galactolipid synthesized by mammalian cells. The synthesis of sulfatide and its non-sulfated form galactosylceramide (GalCer) is initiated by the addition of UDP-galactose to ceramide in a reaction mediated by UDP-galactose:ceramide galactosyltransferase (Cgt), an enzyme highly expressed in oligodendrocytes and Schwann cells. The products of Cgt are a major component of the myelin sheaths that facilitate the transmission of saltatory conduction (Norton, W. T., and Cammer, W. (1984). Isolation and characterization of myelin, In Myelin, P. Morell, ed. (New York: Plenum Press), pp. 147-195). $Cgt^{-/-}$ mice display defects in nerve conduction and die on postnatal days 18-30 from severe tremor and ataxia (Coetzee, T., Fujita, N., Dupree, J., Shi, R., Blight, A., Suzuki, K., and Popko, B. (1996). Myelination in the absence of galactocerebroside and sulfatide: normal structure with abnormal function and regional instability. Cell 86, 209-219). We initially hypothesized that sulfatide contributed to the signals mediating HSC mobilization. Indeed, we found that HSC mobilization induced by G-CSF was virtually absent in $Cgt^{-/-}$ mice. Unexpectedly, the deficit was not due to the absence of BM sulfatide, but rather to an impaired neural influence on osteoblasts. Osteoblasts synthesize the chemokine CXCL12 which attracts HSCs, retaining them in the bone marrow. We have found using mice deficient in dopamine α-hydroxylase (Dbh$^{-/-}$) that noradrenergic signals play a critical role in reducing CXCL12 synthesis by osteoblasts, thereby allowing HSC egress into the bloodstream. Thus, these results suggest that the nervous system influences bone marrow stromal function, which in turn, controls the attraction of stem cells to their niche. Due to certain similarities between the behavior of HSCs and PTICs, it is proposed herein that a similar paradigm might operate in prostate cancer metastasis.

Compounds and Agents Useful for Enhancing Mobilization

It has been shown that hematopoietic stem cells are present in peripheral blood of healthy persons. Unfortunately, they are present in numbers that are insufficient to permit collection of an adequate graft by standard leukapheresis (Kessionger, A. et al., Bone Marrow Transplant 6, 643-646 (1989)). Several methods have been shown to increase the circulation of progenitor and stem cells by "mobilizing" them from the marrow into the peripheral blood. For example, in autologous transplantation, hematopoietic stem/progenitor cells may be mobilized into the peripheral blood (Lane T. A. Transfusion 36, 585-589 (1996)) during the rebound phase of the leukocytes after transient leukopenia induced by myelosuppressive chemotherapy, (Giralt S. et al., Blood, 89, 4531-4536 (1997) by hematopoietic growth factors, or (Lasky L. C. et al., Transfusion 21, 247-260 (1981)) by a combination of both.

One particular aspect of the present invention provides for the combined use of an adrenergic receptor agonist with a mobilizer of hematopoietic stem cells or progenitor/precursor cells. In one embodiment, one or more adrenergic receptor agonists are combined with one or more mobilization agents. In another embodiment, the adrenergic receptor agonist may be an alpha or beta adrenergic receptor agonist. In yet another embodiment, the adrenergic receptor agonist may be an alpha 1 or 2 receptor agonist, or a beta 2 receptor agonist.

In a more particular embodiment, the beta adrenergic receptor agonist may be selected from the group consisting of isoproterenol, metaproterenol, albuterol, terbutaline, salmeterol, salbutamine, bitolterol, pirbuterol acetate, formoterol, epinephrine, and norepinephrine, all of which are known to those skilled in the art. Other beta adrenergic agonists may be found in U.S. Pat. Nos. 6,683,115; 6,670,376; 6,653,323; 6,541,669; 6,306,830; and 6,284,765.

Myelosuppressive Therapy

Hematopoietic stem cell mobilization into peripheral blood has been used as a procedure following myelosuppressive chemotherapy regimens to mobilize hematopoietic stem and progenitor cells into the peripheral blood. Suggested treatment regimens for mobilization may include cyclophosphamide alone, in single doses of 4-7 g/m2, or other agents such as Adriamycin (doxorubicin), carboplatin, Taxol (paclitaxel), etoposide, ifosfamide, daunorubicin, cytosine arabinosides 6-thioguanine, either alone or in combination (Richman, C. M. et al., Blood 47, 1031-1039 (1976); Stiff P. J. et al., Transfusion 23, 500-503 (1983); To L. B. et al. Bone Marrow Transplant 9, 277-284 (1992)). Such a regiment may induce a transient but profound myelosuppression in patients, at about 7-14 days after chemotherapy. This maybe followed on day 10-21 by rapid reappearance of leukocytes in the peripheral blood and frequently a "rebound" increase of the circulating leukocytes above baseline levels. As the leukocyte count rises, hematopoietic progenitor cells also begin to appear in the peripheral blood and rapidly increase.

Hematopoietic stem cells (HSC) collected from mobilized peripheral blood progenitor cells (PBPC) are increasingly used for both autologous and allogeneic transplantation after myeloablative or nonmyeloablative therapies (Lane T. A. Transfusion 36, 585-589 (1996)). Purported advantages of PBPC transplantation include rapid and durable trilineage hematologic engraftment, improved tolerance of the harvesting procedure (without general anesthesia), and possibly diminished tumor contamination in the autologous setting (Lasky L. C. et al., Transfusion 21, 247-260 (1981); Moss T. J. et al, Blood 76, 1879-1883)). Techniques for autologous mobilized PBPC grafting may also be successful for allogeneic transplantation. Early reports in animals and syngeneic transplants in humans supported this hypothesis (Kessionger, A. et al., Bone Marrow Transplant 6, 643-646 (1989)).

Many investigators have reported that PBPC mobilization employing a combination of chemotherapy and followed by growth factor (GM-CSF or G-CSF) administration is more effective than either chemotherapy or growth factor alone (Siena S. et al., Blood 74, 1905-1914 (1989); Pettengel R. et al., Blood, 2239-2248 (1993); Haas R. et al., Bone Marrow Transplant 9, 459-465 (1992); Ho A. D. et al., Leukemia 7, 1738-1746 (1993)). The combination reportedly results in a 50- to 75-fold increase in circulating CFU-GM and 10- to 50-fold increase in CD34+ cells (Pettengel R. et al., Blood, 2239-2248 (1993); Haas R. et al., Bone Marrow Transplant 9, 459-465 (1992); Ho A. D. et al., Leukemia 7, 1738-1746 (1993)). Direct comparisons show that chemotherapy and growth factors resulted in a mean 3,5-fold greater peak number of circulating CFU-GM (range, 0 to 6.8 times greater verses chemotherapy or growth factor alone (Siena S. et al., Blood 74, 1905-1914 (1989); Pettengel R. et al., Blood, 2239-2248 (1993); Haas R. et al., Bone Marrow Transplant 9, 459-465 (1992); Moskowitz C. H. et al. Clin. Cancer Res. 4, 311-316 (1998)).

It is reportedly possible to expand hematopoietic progenitor cells in stroma-containing or nonstromal systems. Expansion systems have reportedly shown increases in CFU_GM of more than 100-fold. Enrichment of CD34+ cells may be required before expansion in nonstromal culture but may not be necessary in stroma-containing systems. Early results of clinical trails are encouraging and have been taken to demonstrate that the engraftment potential of the expanded hematopoietic cells is not compromised by culture. Expansion of cord blood-derived hematopoietic cells may be especially important because of the limited number of cells that can be collected. Successful expansion of primitive and committed hematopoietic cells from cord blood may allow more extensive use in clinical transplantation, particularly in adult patients. Other possible applications of stem cell expansion include purging of tumor cells; production of immune-competent cells, such as dendritic cells and NK cells, and gene therapy.

Permanent marrow recovery after cytotoxic drug and radiation therapy generally depends on the survival of hematopoietic stem cells having long term reconstituting (LTR) potential. The major dose limiting sequelae consequent to chemotherapy and/or radiation therapy are typically neutropenia and thrombocytopenia. Protocols involving dose intensification (i.e., to increase the log-kill of the respective tumour therapy) or schedule compression may exacerbate the degree and duration of myelosuppression associated with the chemotherapy and/or radiation therapy. For instance, in the adjuvant setting, repeated cycles of doxorubicin-based treatment have been shown to produce cumulative and long-lasting damage in the bone marrow progenitor cell populations (Lorhrman et al., (1978) Br. J. Haematol. 40:369). The effects of short-term hematopoietic cell damage resulting from chemotherapy has been overcome to some extent by the concurrent use of G-CSF (Neupogen®.), used to accelerate the regeneration of neutrophils (Le Chevalier (1994) Eur. J. Cancer 30A:410). This approach has been met with limitations also, as it may be accompanied by progressive thrombocytopenia and cumulative bone marrow damage as reflected by a reduction in the quality of mobilized progenitor cells over successive cycles of treatment. Because of the current interest in chemotherapy dose intensification as a means of improving tumor response rates and perhaps patient survival, the necessity for alternative therapies to either improve or replace current treatments to rescue the myeloablative effects of chemotherapy and/or radiation therapy has escalated, and is currently one of the major rate limiting factors for tumor therapy dose escalations.

Transplanted peripheral blood stem cells (PBSC, or autologous PBSC) may provide a rapid and sustained hematopoietic recovery after the administration of high-dose chemotherapy or radiation therapy in patients with hematological malignancies and solid tumours. PBSC transplantation has become the preferred source of stem cells for autologous transplantation because of the shorter time to engraftment and the lack of a need for surgical procedures such as are necessary for bone marrow harvesting (Demirer et al. (1996) Stem Cells 14:106-116; Pettengel et al., (1992) Blood 82:2239-2248). Although the mechanism of stem cell release into the peripheral blood from the bone marrow is not well understood, agents that augment the mobilization of CD34+ cells may prove to be effective in enhancing autologous PBSC transplantation. G-CSF and GM-CSF are currently the most commonly used hematopoietic growth factors for PBSC mobilization, although the mobilized cellular profiles can differ significantly from patient to patient. Therefore, other agents, such as those proposed and described herein are required for this clinical application.

Growth Factors and Colony Stimulating Factors

A number of proteins have been identified and may be utilized clinically for hematopoietic progenitor cell development and hematopoietic cell proliferation or multiplication. These include recombinant-methionyl human G-CSF (Neupogen®., Filgastim; Amgen), GM-CSF (Leukine®, Sargramostim; Immunex), erythropoietin (rhEPO, Epogene; Amgen), thrombopoietin (rhTPO; Genentech), interleukin-11 (rhIL-11, Neumega®; American Home Products), Flt3 ligand (Mobista; Immunex), multilineage hematopoietic factor (MARstem™; Maret Pharm.), myelopoietin (Leridistem; Searle), IL-3, myeloid progenitor inhibitory factor-1 (Mirostipen; Human Genome Sciences), stem cell factor (rhSCF, Stemgen®; Amgen).

Agents that Decrease the Expression or Function of CXCL12 (SDF-1) or that Block or Antagonize CXCR4

In another embodiment, the mobilization agent may be an agent that decreases the expression or function of a chemokine, more particularly, CXCL12, also known as SDF-1. The human amino acid sequence (SEQ ID NO: 1) has Gen Bank accession number CAG29279. The alpha isoform has GenBank accession number NP_954637. The beta isoform has GenBank accession number NP_000600. The gamma isoform has GenBank accession number NP_001029058. Alternatively, another aspect of the invention provides for a mobilization agent that blocks or antagonizes a chemokine receptor, in particular, CXCR4. The human amino acid sequence (SEQ ID NO: 2) has GenBank accession number CAA12166.

Chemokines are a superfamily of chemoattractant proteins. Chemokines regulate a variety of biological responses and they promote the recruitment of multiple lineages of leukocytes and lymphocytes to a body organ tissue. Chemokines may be classified into two families according to the relative position of the first two cysteine residues in the protein. In one family, the first two cysteines are separated by one amino acid residue, the CXC chemokines, and in the other family the first two cysteines are adjacent, the CC chemokines. Two minor subgroups contain only one of the two cysteines (C) or have three amino acids between the cysteines (CX3C). In humans, the genes of the CXC chemokines are clustered on chromosome 4 (with the exception of SDF-1 gene, which has been localized to chromosome 10) and those of the CC chemokines on chromosome 17.

The molecular targets for chemokines are cell surface receptors. One such receptor is CXC chemokine receptor 4 (CXCR4), which is a 7 transmembrane protein, coupled to G1 and was previously called LESTR (Loetscher, M., Geiser, T., O'Reilly, T., Zwahlen, R., Baggionlini, M., and Moser, B., (1994) J. Biol. Chem, 269, 232-237), HUMSTR (Federspiel, B., Duncan, A. M. V., Delaney, A., Schappert, K., Clark-Lewis, I., and Jirik, F. R. (1993) Genomics 16, 707-712) and Fusin (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877). CXCR4 is widely expressed on cells of hemopoietic origin, and is a major co-receptor with CD4 for human immunodeficiency virus 1 (HIV-1) (Feng, Y., Broeder, C. C., Kennedy, P. E., and Berger, E. A. (1996) HIV-1 entry cofactor: Functional cDNA cloning of a seven-transmembrane G protein-coupled receptor, Science 272, 872-877).

Chemokines are thought to mediate their effect by binding to seven transmembrane G protein-coupled receptors, and to attract leukocyte subsets to sites of inflammation (Baglionini et al. (1998) Nature 392: 565-568). Many of the chemokines have been shown to be constitutively expressed in lymphoid tissues, indicating that they may have a homeostatic function in regulating lymphocyte trafficking between and within lymphoid organs (Kim and Broxmeyer (1999) J. Leuk. Biol. 56: 6-15).

Stromal cell derived factor one (SDF-1), also known as CXCL12, is a member of the CXC family of chemokines that has been found to be constitutively secreted from the bone marrow stroma (Tashiro, (1993) Science 261, 600-602). The human and mouse SDF-1 predicted protein sequences are approximately 92% identical. Stromal cell derived factor-1α (SDF-1α) and stromal cell derived factor-1β. (SDF-1 β) are closely related (together referred to herein as SDF-1). The native amino acid sequences of SDF-1 α and SDF-1 βare known, as are the genomic sequences encoding these proteins (see U.S. Pat. No. 5,563,048 issued 8 Oct. 1996, and U.S. Pat. No. 5,756,084 issued 26 May 1998). Identification of genomic clones has shown that the alpha and beta isoforms are a consequence of alternative splicing of a single gene. The alpha form is derived from exons 1-3 while the beta form contains an additional sequence from exon 4. The entire human gene is approximately 10 Kb. SDF-1 was initially characterized as a pre-B cell-stimulating factor and as a highly efficient chemotactic factor for T cells and monocytes (Bieul et al. (1996) J. Exp. Med. 184:1101-1110).

Biological effects of SDF-1 may be mediated by the chemokine receptor CXCR4 (also known as fusin or LESTR), which is expressed on mononuclear leukocytes including hematopoietic stem cells. SDF-1 is thought to be the natural ligand for CXCR4, and CXCR4 is thought to be the natural receptor for SDF-1 (Nagasawza et al. (1997) Proc. Natl. Acad. Sci. USA 93:726-732). Genetic elimination of SDF-1 is associated with parinatal lethality, including abnormalities in cardiac development, B-cell lymphopoiesis, and bone marrow myelopoiesis (Nagasawa et al. (1996) Nature 382:635-637).

SDF-1 is functionally distinct from other chemokines in that it is reported to have a fundamental role in the trafficking, export and homing of bone marrow progenitor cells (Aiuti, A., Webb, I. J., Bleul, C., Springer, T:, and Guierrez-Ramos, J. C., (1996) J. Exp. Med. 185, 111-120 and Nagasawa, T., Hirota, S., Tachibana, K., Takakura N., Nishikawa, S.-I., Kitamura, Y., Yoshida, N., Kikutani, H., and Kishimoto, T., (1996) Nature 382, 635-638). SDF-1 is also structurally distinct in that it has only about 22% amino acid sequence identity with other CXC chemokines (Bleul, C. C., Fuhlbrigge, R. C., Casasnovas, J. M., Aiuti, A., and Springer, T. A., (1996) J. Exp. Med. 184, 1101-1109; Katayama, Y., Hidalgo, A., Furie, B. C., Vestweber, D., Furie, B., and Frenette, P. S. (2003). PSGL-1 participates in E-selectin-mediated progenitor homing to bone marrow: evidence for cooperation between E-selectin ligands and alpha4 integrin. Blood 102, 2060-2067). SDF-1 appears to be produced constitutively by several cell types, and particularly high levels are found in bone-marrow stromal cells (Shirozu, M., Nakano, T., Inazawa, J., Tashiro, K., Tada, H. Shinohara, T., and Honjo, T., (1995) Genomics, 28, 495-500 and Bleul, C. C., Fuhlbrigge, R. C., Casasnovas, J. M., Aiuti, A., and Springer, T. A., (1996) J. Exp. Med. 184, 1101-1109). A basic physiological role for SDF-1 is implied by the high level of conservation of the SDF-1 sequence between species. In vitro, SDF-1 stimulates chemotaxis of a wide range of cells including monocytes and bone marrow derived progenitor cells (Aiuti, A., Webb, U., Bleul, C., Springer, T., and Guierrez-Ramos, J. C., (1996) J. Exp. Med. 185, 111-120 and Bleul, C. C., Fuhlbrigge, R. C., Casasnovas, J. M., Aiuti, A., and Springer, T. A., (1996) J. Exp. Med. 184, 1101-1109). SDF-1 also stimulates a high percentage of resting and activated T-lymphocytes (Bleul, C. C., Fuhlbrigge, R. C., Casasnovas, J. M., Aiuti, A., and Springer, T. A., (1996) J. Exp. Med. 184, 1101-1109 and Campbell, J. J., Hendrick, J., Zlotnik, A., Siani, M. A., Thompson, D. A., and Butcher, E. C., (1998) Science, 279 381-383).

Native SDF-1 has been demonstrated to induce the maturation and activation of platelets (Hamada T. et al., J. Exp. Med. 188, 638-548 (1998); Hodohara K. et al., Blood 95, 769-775 (2000); Kowalska M. A. et al., Blood 96, 50-57 (2000)), and CXCR4 is expressed on the megakaryocytic lineage cells (CFUOMeg) (Wang J-F. et al., Blood 92, 756-764 (1998)).

In one embodiment of the invention, agents that decrease the expression of CXCL12 or that block or antagonize CXCR4 may be used in combination with an adrenergic agonist to enhance the mobilization of stem cells. These agents that decrease the expression of CXCL12 or that block or antagonize CXCR4 may be selected from the group consisting of small organic molecules, polypeptides, nucleic acids and carbohydrates. In more particular embodiments, the polypeptides that decrease the expression of CXCL12 may be selected from the group consisting of a cytokine, a colony stimulating factor, a protease or a chemokine other than CXCL12. The cytokine may be selected from the group consisting of interleukin-1 (IL-1), interleukin-3 (IL-3), interleukin-6 (IL-6), interleukin-11 (IL-11), interleukin-7 (IL-7) and interleukin-12 (IL12). The protease may be selected from the group consisting of a metalloproteinase (like MMP2 or MMP9) a serine protease, (like cathepsin G, or elastase) a cysteine protease (like cathepsin K) and a dipeptidyl peptidase-1 (DDP-1 OR CD26). The chemokine other than CXCL12 may be selected from the group consisting of IL-8, MIP-1α and Groβ. The colony stimulating factor may be selected from the group consisting of granulocyte colony stimulating factor (G-CSF), granulocyte-macrophage colony stimulating factor (GM-CSF), macrophage colony stimulating factor (M-CSF), stem cell factor, FLT-3 ligand or a combination thereof. The nucleic acid may be a DNA or an RNA molecule. The nucleic acid may be a small interfering RNA (siRNA) molecule or an antisense molecule specific for CXCL12 or CXCR4. The carbohydrate may be a sulfated carbohydrate selected from the group consisting of Fucoidan and sulfated dextran.

Selecting Compounds or Agents that Act as Agonists or Antagonists of the Adrenergic Receptors Various adrenergic receptor agonists and antagonists, including those specific for the alpha or beta receptors, have been identified and are known in the art.

Examples of agonists in the art include but are not limited to isoproterenol, metaproterenol, albuterol, clenbuterol, terbutaline, salmeterol, salbutamine, bitolterol, pirbuterol acetate, formoterol, epinephrine, and norepinephrine. Additional agonists may be found in U.S. Pat. Nos. 6,683,115; 6,670,376; 6,653,323; 6,541,669; 6,306,830 and 6284765. Particularly preferred are compounds or agents which are selective for the beta 2 adrenergic receptor. The invention provided herein includes the use of these beta 2 adrenergic receptor agonists for the modulation, in particular, the enhancement of hematopoietic stem cell or progenitor cell mobilization when used in conjunction with other mobilizers, as described herein.

β-adrenergic receptor antagonists are a class of drugs that compete with beta-adrenergic agonists for available receptor sites; some compete for both β1- and β 2-adrenergic receptors (e.g., propranolol) while others bind primarily to either β 1-(e.g., metoprolol) or β 2-adrenergic receptors; these compounds are used in the treatment of a variety of cardiovascular diseases where beta-adrenergic blockade is desirable. Antagonists have an intrinsic activity of zero. These agents are also called beta-adrenergic receptor blocking agents, or beta-adrenoreceptor antagonists. They are also known as beta-blockers. Examples of these agents include Acebutolol (N-[3-Acetyl-4-[2-hydroxy-3-[(1-methylethyl)amino]phenyl]butamamide), Atenolol(4-[2-Hydroxy-3-[(1-methylethyl)amino]-propoxy]benzeneacetamide), Betaxolol(1-[4-[2-(cyclopropylmethoxy)ethyl]-phenoxy]-3-[(1-methylethyl)amino]-2-propanol), Bisoprolol(1-[4-[(2-(1-methylethoxy)ethoxy)methyl]phenoxy]-3-[(1-methylethyl)amino]-2-propanol), Esmolol(Methyl-4-[2-hydroxy-3-[1-methylethyl)amino]-propoxy]benzenepropanoate), Metoprolol(1-[4-(2-Methoxyethyl)phenoxy]-3-[1-methylethyl)amino]-2-propanol, Carteolol(5-[3-[(1,1-Dimethylethyl)amino]-2-hydroxypropoxy]-3,4-dihydro-2(1H)-quinolinone), Nadolol(5-[3-[(1,1-Dimethylethyl)amino]-2-hydroxypropoxy]-1,2,3,4-tetrahydro-2,3-naphthalenediol, Penbutolol(1-(2-Cyclopentylphenoxy)-3-[1,1-dimethylethyl)amino]-2-propanol), Pindolol(1-(1H-Indol-4-yloxy)-3-[1-methylethyl)amino]-2-propanol), Propranolol(1-[(1-Methylethyl)amino]-3-(1-naphthalenyloxy)-2-propanol), Sotalol(N-[4-[1-Hydroxy-2-[(1-methylethyl)amino]ethyl]phenyl}methanesulfonamide), Timolol(1-[(1,1-Dimethylethyl)amino]-3-[[4-morpholinyl-1,2,5-thiadizaol-3-yl]oxy]-2-propanol), Carvedilol(1-(Carbazol-4-yloxy)-3-[[2-(O-methoxyphenoxy)ethyl]amino]2-propanol), Labetalol(2-Hydroxy-5-[1-hydroxy-2-{(1-methyl-3-phenylpropyl) amino]ethyl]benzamide), Alprenolol(1-[(Methylethyl) amino]-3-[2-(2-propenyl)phenoxy]-2-propanol, and ICI 118, 551.

Based on this discovery, the present invention further provides for a method of discovery of agents or compounds which modulate mobilization of stem cells or progenitor cells from the bone marrow to the blood compartment. Thus, in one embodiment, methods are provided for screening agents or compounds which act as agonists of the adrenergic receptors, thereby identifying compounds that modulate the mobilization of stem cells or progenitor from the bone marrow when combined with known or candidate compounds that act as mobilizers.

In one embodiment, agents that interact with (e.g., bind to) and act as an agonist or an antagonist of an adrenergic receptor, are identified in a cell-based assay system. In accordance with this embodiment, cells expressing an adrenergic receptor, a fragment of an adrenergic receptor, or a binding fragment thereof, are contacted with a candidate compound or a control compound and the ability of the candidate compound to interact with the receptor or fragment thereof is determined. Alternatively, the ability of a candidate compound to compete for binding with a known ligand or compound known to bind the receptor is measured. If desired, this assay may be used to screen a plurality (e.g. a library) of candidate compounds. The cell, for example, can be of prokaryotic origin (e.g., E. coli) or eukaryotic origin (e.g., yeast, insect or mammalian). Further, the cells can express the receptor endogenously or be genetically engineered to express the receptor, a binding fragment or a receptor fusion protein. In some embodiments, the receptor or fragment thereof, or the candidate compound is labeled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between the receptor and a candidate compound. The ability of the candidate compound to interact directly or indirectly with a receptor or binding fragment thereof or a fusion protein or to modulate the activity of the receptor can be determined by methods known to those of skill in the art. For example, the interaction or modulation by a candidate compound can be determined by flow cytometry, a scintillation assay, immunoprecipitation or western blot analysis, based on the present description, or by a competitive radioreceptor assay.

Selecting the compounds that interact with or bind to an adrenergic receptor may be performed in multiple ways. The compounds may first be chosen based on their structural and functional characteristics, using one of a number of approaches known in the art. For instance, homology modeling can be used to screen small molecule libraries in order to determine which molecules would be candidates to interact with the receptor thereby selecting plausible targets. See neogenesis.com for a commercially available screening of compounds using multiple different approaches such as an automated ligand identification system and quantized surface complementarity. The compounds to be screened can include both natural and synthetic ligands. Furthermore, any desired compound may be examined for its ability to interact with or bind to a receptor including as described below.

Binding to or interaction with an adrenergic receptor may be determined by performing an assay such as, e.g., a binding assay between a desired compound and an adrenergic receptor. In one aspect, this is done by contacting said compound to an adrenergic receptor and determining its dissociation rate. Numerous possibilities for performing binding assays are well known in the art. The indication of a compound's ability to bind to the receptor is determined, e.g., by a dissociation rate, and the correlation of binding activity and dissociation rates is well established in the art. For example, the assay may be performed by radio-labeling a reference compound, or other suitable radioactive marker, and incubating it with the cell bearing an adrenergic receptor, in particular, beta 2. Test compounds are then added to these reactions in increasing concentrations. After optimal incubation, the reference compound and receptor complexes are separated, e.g., with chromatography columns, and evaluated for bound $^{125}I$-labeled peptide with a gamma (γ) counter. The amount of the test compound necessary to inhibit 50% of the reference compound's binding is determined. These values are then normalized to the concentration of unlabeled reference compound's binding (relative inhibitory concentration $(RIC)^{-1}$=concentration$_{test}$/concentration$_{reference}$). A small $RIC^{-1}$ value indicates strong relative binding, whereas a large $RIC^{-1}$ value indicates weak relative binding. See, for example, Latek et al., Proc. Natl. Acad. Sci. USA, Vol. 97, No. 21, pp. 11460-11465, 2000. A receptor agonist or antagonist mimic may be computationally evaluated and designed by means of a series of steps in which chemical groups or fragments are screened and selected for their ability to associate with the individual binding pockets or interface surfaces of the protein (e.g. the receptor). One skilled in the art may employ one of several methods to screen chemical groups or fragments for their ability to associate with the receptor. This process may begin by visual inspection of, for example, the protein/protein interfaces or the binding site on a computer screen based on the available crystal complex coordinates of the receptor, including a protein known to interact with the receptor. Selected fragments or chemical groups may then be positioned in a variety of orientations, or docked, at an individual surface of the receptor that participates in a protein/protein interface or in the binding pocket. Docking may be accomplished using software such as QUANTA and SYBYL, followed by energy minimization and molecular dynamics with standard molecular mechanics forcefields, such as CHARMM and AMBER (AMBER, version 4.0 (Kollman, University of California at San Francisco © 1994); QUANTA/CHARMM (Molecular Simulations, Inc., Burlington, Mass., ©1994)). Specialized computer programs may also assist in the process of selecting fragments or chemical groups. These include: GRID (Goodford, 1985, J. Med. Chem. 28:849-857), available from Oxford University, Oxford, UK; MCSS (Miranker & Karplus, 1991, Proteins: Structure, Function and Genetics 11:29-34), available from Molecular Simulations, Burlington, Mass.; AUTODOCK (Goodsell & Olsen, 1990, Proteins: Structure, Function, and Genetics 8:195-202), available from Scripps Research Institute, La Jolla, Calif.; and DOCK (Kuntz et al., 1982, J. Mol. Biol. 161:269-288), available from University of California, San Francisco, Calif. Once suitable chemical groups or fragments that bind to the receptor have been selected, they can be assembled into a single compound. Assembly may proceed by visual inspection of the relationship of the fragments to each other in the three-dimensional image displayed on a computer screen in relation to the structure coordinates thereof. This would be followed by manual model building using software such as QUANTA or SYBYL. Useful programs to aid one of skill in the art in connecting the individual chemical groups or fragments include: CAVEAT (Bartlett et al., 1989, 'CAVEAT: A Program to Facilitate the Structure-Derived Design of Biologically Active Molecules'. In Molecular Recognition in Chemical and Biological Problems', Special Pub., Royal Chem. Soc. 78:182-196), available from the University of California, Berkeley, Calif.; 3D Database systems such as MACCS-3D (MDL Information Systems, San Leandro, Calif.). This area is reviewed in Martin, 1992, J. Med. Chem. 35:2145-2154); and HOOK (available from Molecular Simulations, Burlington, Mass.). Instead of proceeding to build a receptor agonist or antagonist mimic, in a step-wise fashion one fragment or chemical group at a time, as described above, such compounds may be designed as a whole or 'de novo' using either an empty binding site or the surface of a protein that participates in protein/protein interactions or optionally including some portion(s) of a known activator(s). These methods include: LUDI (Bohm, 1992, J. Comp. Aid. Molec. Design 6:61-78), available from Molecular Simulations, Inc., San Diego, Calif.; LEGEND (Nishibata & Itai, 1991, Tetrahedron 47:8985), available from Molecular Simulations, Burlington, Mass.; and LeapFrog (available from Tripos, Inc., St. Louis, Mo.). Other molecular modeling techniques may also be employed in accordance with this invention. See, e.g., Cohen et al., 1990, J. Med. Chem. 33:883-894. See also, Navia & Murcko, 1992, Current Opinions in Structural Biology 2:202-210.

Once a compound has been designed by the above methods, the efficiency with which that compound may bind to or interact with the receptor protein may be tested and optimized by computational evaluation. Agonists or antagonists may interact with the receptor in more than one conformation that is similar in overall binding energy. In those cases, the deformation energy of binding is taken to be the difference between the energy of the free compound and the average energy of the conformations observed when the inhibitor binds to the receptor protein.

A compound selected for binding to the receptors may be further computationally optimized so that in its bound state it would preferably lack repulsive electrostatic interaction with the target protein. Such non-complementary electrostatic interactions include repulsive charge-charge, dipole-dipole and charge-dipole interactions. Specifically, the sum of all electrostatic interactions between the inhibitor and the receptor protein when the mimic is bound to it preferably make a neutral or favorable contribution to the enthalpy of binding. Specific computer software is available in the art to evaluate compound deformation energy and electrostatic interaction. Examples of programs designed for such uses include: Gaussian 92, revision C (Frisch, Gaussian, Inc., Pittsburgh, Pa. ©1992); AMBER, version 4.0 (Kollman, University of California at San Francisco © 1994); QUANTA/CHARMM (Molecular Simulations, Inc., Burlington, Mass., ©1994); and Insight II/Discover (Biosym Technologies Inc., San Diego, Calif., © 1994). These programs may be implemented, for instance, using a computer workstation, as are well-known in the art. Other hardware systems and software packages will be known to those skilled in the art.

Once a receptor modulating compound (preferably an agonist) has been optimally designed, for example as described above, substitutions may then be made in some of its atoms or chemical groups in order to improve or modify its binding properties, or its pharmaceutical properties such as stability or toxicity. Generally, initial substitutions are conservative, i.e., the replacement group will have approximately the same size, shape, hydrophobicity and charge as the original group. One of skill in the art will understand that substitutions known in the art to alter conformation should be avoided. Such altered chemical compounds may then be analyzed for efficiency of binding to the adrenergic receptor by the same computer methods described in detail above.

Screening Methods for Identifying Agents that Decrease the Expression or Function of CXCL12 or that Antagonize CXCR4

Methods that may be utilized to determine whether a molecule functions to decrease the expression of CXCL12 or to act as a CXCR4 antagonists include, but are not limited to, the following: Inhibition of the induction of CXCL12 (SDF-1) receptor mediated rise in free cytosolic Ca2+ concentration ([Ca2+]) in response to native CXCL12 (or agonist analogs of CXCL12) (Loetscher P. et al., (1998) J. Biol. Chem. 273, 24966-24970), inhibition of SDF-1-induction of phosphoinositide-3 kinase or Protein Kinase C activity (Wang, J-F et al., (2000) Blood 95, 2505-2513), inhibition of SDF-1-induced migration of CD34+ hematopoietic stem cells in a two-chamber migration (transwell) assay (Durig J. et al., (2000) Leukemia 14, 1652-1660; Peled A. et al., (2000) Blood 95, 3289-2396), inhibition of SDF-1 associated transmigration of CD34+/CXCR4+ cells through vascular endothelial cells in a cell chemotaxis assay, cell adhesion assay, or real-time tracking of CD34+ cell migration in 3-D extracellular matrix-like gel assays (Peled A. et al., (2000) Blood 95, 3289-2396), inhibition of SDF-1 associated chemotaxis of marrow-derived B cell precursors (Nuzzo M. et al., Eur. J. Immunol. (1997) 27, 1788-1793), preventing CXCR4 signal transduction and coreceptor function in mediating the entry of T- and dual-tropic HIV isolates (Zhou N. et al., (2000) 39, 3782-3787), inhibition of SDF-1 associated increases of CFU-GM, CGU-M or BFU-E colony formation by peripheral blood Inc+ CD34+ progenitor cells (Lataillade J-J. et al/. (2000) Blood 95, 756-768), or inhibition of integrin-mediated adhesion of T cells to fibronectin and ICAM-1 (Buckley C. D et al., (2000) J. Immunology 165, 3423-3429). Where it is necessary to assess the inhibition of CXCL12 associated mechanisms in the aforementioned assays, various concentrations of CXCR4 antagonist may be incubated under the appropriate experimental conditions in the presence of CXCL12, in assays to determine if the CXCR4 antagonist associated repression of the respective mechanism results directly from inhibition of the CXCR4 receptor. ([Ca2+]) mobilization, chemotaxis assays or other assays that measure the induction of CXCR4 are not limited to the cell types indicated in the associated references, but may include other cell types that demonstrate CXCR4 associated, and specific, activation.

In alternative aspects, the invention provides uses for CXCR4 antagonists that are identified as molecules that bind to CXCR4 (whether reversible or irreversible) and are associated with the repression of CXCR4 associated activity. Binding affinity of a CXCR4 antagonists may for example be associated with ligand binding assay dissociation constants ($K_D$) in the range of a minimum of 1 pM, 10 pM, 100 pM, 1 uM, 10 uM or 100 uM up to a maximum of 1 mM, or any value in any such range. CXCR4 antagonist associated $K_D$ values may be determined through alternative approaches, such as standard methods of radioligand binding assays, including High Throughput Fluorescence Polarization, scintillation proximity assays (SPA), and Flashplates® (Allen et al., (2000) J. Biomolecular Screening 5, 63-69), where the competing ligand is native SDF-1. Alternatively, the affinity of a CXCR4 antagonist for the SDF-1 receptor (CXCR4) may be ascertained through inhibition of native SDF-1 binding to the CXCR4, where various concentrations of the CXCR4 antagonist are added in the presence of SDF-1 and a recombinant CXCR4 or a cell type that expresses an adequate receptor titer.

In one embodiment, a method of screening is proposed for identifying novel compounds that act as mobilization agents. The method calls for the following steps:

a) plating a population of bone marrow cells with stromal cells with or without additional growth factor supplementation;

b) supplementing the cells of step a) with medium containing a candidate or test compound with or without an adrenergic receptor agonist; and c) quantitating the number of hematopoietic stem cells or progenitor cells in the culture supernatant.

A candidate or test compound is considered to be effective if the number of hematopoietic stem cells or progenitor cells is greater in the culture supernatant in the presence but not in the absence of the test compound.

The number of hematopoietic stem cells or progenitor cells may be quantitated using a variety of methods, including fluorescent activated cell sorting, whereby the cells are labeled with particular markers specific for hematopoietic stem cells or progenitor cells. For example, cells having the following phenotype are indicative of the presence of hematopoietic stem cells: $lin^- sca-1^+c-kit^+$. Alternatively, undifferentiated hematopoietic stem cells or progenitor cells from the bone marrow, when cultured in methyl cellulose with stromal cells, will migrate under the stromal layer and demonstrate a very characteristic cobblestone appearance. Upon addition of an adrenergic agonist or a test agent that acts to mobilize the hematopoietic stem cells or progenitor cells, the undifferentiated stem cells will migrate from under the stromal cells into the supernatant. The number of these cells in the supernatant can then be counted and surface markers identified using standard procedures known to those skilled in the art, for example, by flow cytometric procedures.

Candidate Compounds and Agents

Examples of agents, candidate compounds or test compounds include, but are not limited to, nucleic acids (e.g., DNA and RNA), carbohydrates, lipids, proteins, peptides, peptidomimetics, small molecules and other drugs. In one preferred aspect, agents can be obtained using any of the numerous suitable approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. No. 5,738,996; and U.S. Pat. No. 5,807,683).

Phage display libraries may be used to screen potential ligands or adrenergic receptor modulators. Their usefulness lies in the ability to screen, for example, a library displaying a billion different compounds with only a modest investment of time, money, and resources. For use of phage display libraries in a screening process, see, for instance, Kay et al., Methods, 240-246, 2001. An exemplary scheme for using phage display libraries to identify compounds that are agonists of the adrenergic receptor or that act as mobilizers of stem cells may be described as follows: initially, an aliquot of the library is introduced into microtiter plate wells that have previously been coated with target protein, e.g. an adrenergic receptor. After incubation (e.g. 2 hrs), the nonbinding phage are washed away, and the bound phage are recovered by denaturing or destroying the target with exposure to harsh conditions such as, for instance pH 2, but leaving the phage intact. After transferring the phage to another tube, the conditions are neutralized, followed by infection of bacteria with the phage and production of more phage particles. The amplified phage are then rescreened to complete one cycle of affinity selection. After three or more rounds of screening, the phage are plated out such that there are individual plaques that can be further analyzed. For example, the conformation of binding activity of affinity-purified phage for an adrenergic receptor may be obtained by performing ELISAs. One skilled in the art can easily perform these experiments. In one aspect, a receptor molecule used for any of the assays may be selected from a recombinant adrenergic receptor protein, or a fusion protein, an analog, derivative, or mimic thereof.

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented, e.g., presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

The methods of screening compounds may also include the specific identification or characterization of such compounds, whose stem cell mobilization potential was determined by the methods described herein. If the identity of the compound is known from the start of the experiment, no additional assays are needed to determine its identity. However, if the screening for compounds that modulate the receptor is done with a library of compounds, it may be necessary to perform additional tests to positively identify a compound that satisfies all required conditions of the screening process. There are multiple ways to determine the identity of the compound. One process involves mass spectrometry, for which various methods are available and known to the skilled artisan (see for instance neogenesis.com). Neogenesis' ALIS (automated ligand identification system) spectral search engine and data analysis software allow for a highly specific identification of a ligand structure based on the exact mass of the ligand. One skilled in the art can also readily perform mass spectrometry experiments to determine the identity of the compound.

Antibodies, including polyclonal and monoclonal antibodies, particularly anti-CXCL12 or anti-CXCR4 antibodies may be useful as compounds to modulate stem cell mobilization when used in conjunction with an adrenergic receptor agonist. The adrenergic receptor or its subunits or CXCL12 or CXCR4 may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of CXCL12 or CXCR4 may be discovered or synthesized, and may be used in diagnostic and/or therapeutic protocols.

Antisense Therapy

The relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state. In the present invention, the targets are nucleic acids encoding CXCL12 or CXCR4; in other words, a gene encoding either CXCL12 or CXCR4, or mRNA expressed from the CXCL12 or CXCR4 gene. mRNA which encodes CXCL12 or CXCR4 is presently the preferred target. The targeting process also includes determination of a site or sites within the nucleic acid sequence for the antisense interaction to occur such that modulation of gene expression will result.

While the present invention relates primarily to promoting egress or mobilization of hematopoietic stem cells from their niche in the bone marrow to the peripheral circulation, it is proposed that the same mechanisms may be involved in the egress of cancer stem cells from their niche into the circulation, lymphatic system or to distant organs and tissues, thus exacerbating the metastatic process. Thus, the use of an antisense molecule or a small interfering nucleic acid molecule, such as a siRNA (small interfering RNA) or shRNA (short hairpin RNA) that inhibits the expression or function of CXCL12 or CXCR4 may be useful only when combined with treatment with an anti-cancer drug or with irradiation therapy for the reasons discussed below.

The current view of others is that the inhibition of the CXCL12 receptor, CXCR4, can prevent metastasis and clinical trials are underway to address this issue. However, based on the studies presented herein, it is proposed that if the egress of cancer stem cells is under the same or similar regulatory control as other (non-cancer) stem cells, such as hematopoietic stem cells, CXCR4 inhibition may actually mobilize cancer stem cells from their niche in the microenvironment, or in the tumor cell itself, and may paradoxically lead to increased metastasis. Thus, it may be that while this strategy may be useful in the treatment of cancer, it may be essential to combine this therapy with administration of a chemotherapeutic drug or irradiation therapy, as proposed herein. Inhibition or blocking of the expression or function of CXCL12 or CXCR4 may elevate the cancer stem cell from a state of quiescence to an activated or actively proliferating mode, thus also increasing their sensitivity to therapeutic drugs or treatments that target actively dividing cells. Thus, the need for combined therapy using a stem cell mobilizer with anti-cancer drugs or radiation therapy is proposed. Moreover, as demonstrated herein, the mobilization of stem cells appears to be optimized when an alpha or beta adrenergic agonist is combined with a stem cell mobilizer. Thus, in another embodiment, it is envisioned that the alpha or beta adrenergic agonist may be used together with a stem cell mobilizer to optimize the egress of cancer stem cells from their niche in the microenvironment, which may bring them from a quiescent state to an actively dividing state, thus making them more sensitive to chemotherapy or irradiation therapy, which may target actively dividing cells.

Furthermore, the studies presented herein suggest that adrenergic signaling contributes to reducing the synthesis of CXCL12 by stromal cells, and as such, may promote the release of tumor cells, in particular, prostate tumor cells into the circulation. Thus, it is suggested by the studies presented herein that the use of an alpha or beta adrenergic antagonist, when used alone or when combined with chemotherapy or irradiation therapy, may be useful for treating patients suffering from a cancerous condition.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention, which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'-or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding CXCL12 or CXCR4, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a particular target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a particular target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of CXCL12 or CXCR4. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, or by Western blot or ELISA assay of protein expression, or by an immunoprecipitation assay of protein expression. Effects on cell proliferation or tumor cell growth or metastasis can also be measured. Inhibition is presently preferred.

The antisense oligonucleotides of this invention can be used in diagnostics, therapeutics, prophylaxis, and as research reagents and in kits. Since the oligonucleotides of this invention hybridize to nucleic acids encoding CXCL12 or CXCR4, sandwich, calorimetric and other assays can easily be constructed to exploit this fact. Provision of means for detecting hybridization of oligonucleotide with the CXCL12 or CXCR4 gene or mRNA can routinely be accomplished. Such provision may include enzyme conjugation, radiolabelling or any other suitable detection systems. Kits for detecting the presence or absence of these molecules may also be prepared.

The present invention is also suitable for diagnosing certain cancers in tissue or other samples from patients suspected of having hyperproliferative condition or cancer such as, but not limited to brain cancer, skin cancer, lung cancer, bladder cancer and prostate cancer. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 10 to about 50 nucleobases. Particularly preferred are antisense oligonucleotides comprising from about 10 to about 30 nucleobases (i.e. from about 10 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2=, 3= or 5=hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3= to 5=phosphodiester linkage.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering 1990, pages 858-859, Kroschwitz, J. I., ed. John Wiley & Sons, those disclosed by Englisch et al. (Angewandte Chemie, International Edition 1991, 30, 613-722), and those disclosed by Sanghvi, Y. S., Chapter 15, Antisense Research and Applications 1993, pages 289-302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications 1993, CRC Press, Boca Raton, pages 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA 1989, 86, 6553-6556), cholic acid (Manoharan et al., Bioorg. Med. Chem. Lett. 1994, 4, 1053-1059), a thioether, e.g., hexyl-5-tritylthiol (Manoharan et al., Ann. N.Y. Acad. Sci. 1992, 660, 306-309; Manoharan et al., Bioorg. Med. Chem. Let. 1993, 3, 2765-2770), a thiocholesterol (Oberhauser et al., Nucl. Acids Res. 1992, 20, 533-538), an aliphatic chain, e.g., dodecandiol or undecyl residues (Saison-Behmoaras et al., EMBO J. 1991, 10, 1111-1118; Kabanov et al., FEBS Lett. 1990, 259, 327-330; Svinarchuk et al., Biochimie 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett. 1995, 36, 3651-3654; Shea et al., Nucl. Acids Res. 1990, 18, 3777-3783), a polyamine or a polyethylene glycol chain (Manoharan et al., Nucleosides & Nucleotides 1995, 14, 969-973), or adamantane acetic acid (Manoharan et al., Tetrahedron Lett. 1995, 36, 3651-3654), a palmityl moiety (Mishra et al., Biochim. Biophys. Acta 1995, 1264, 229-237), or an octadecylamine or hexylamino-carbonyl-oxycholesterol moiety (Crooke et al., J. Pharmacol. Exp. Ther. 1996, 277, 923-937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—CH.sub.2 CH.sub.2 OCH.sub.3) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—CH2 CH2 OCH3) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also contemplated.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the skilled artisan. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., Helv. Chim. Acta 1995, 78, 486-504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. Pharmaceutically acceptable salts are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," J. of Pharma Sci. 1977, 66, 1-19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention may be prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention (any antisense oligonucleotides or siRNA molecules) may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems 1991, 8, 91-192; Muranishi, Critical Reviews in Therapeutic Drug Carrier Systems 1990, 7, 1-33). One or more penetration enhancers from one or more of these broad categories may be included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., Critical Reviews in Therapeutic Drug Carrier Systems 1991, page 92; Muranishi, Critical Reviews in Therapeutic Drug Carrier Systems 1990, 7, 1; El-Hariri et al., J. Pharm. Pharmacol. 1992 44, 651-654).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems 1991, page 92; Muranishi, Critical Reviews in Therapeutic Drug Carrier Systems 1990, 7, 1-33; Buur et al., J. Control Rel. 1990, 14, 43-51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems 1991, page 92); and perfluorochemical emulsions, such as FC43 (Takahashi et al., J. Pharm. Phamacol. 1988, 40, 252-257).

Non-surfactants include, for example, unsaturated cyclic ureas, 1-alkyl- and 1-alkenylazacyclo-alkanone derivatives (Lee et al., Critical Reviews in Therapeutic Drug Carrier Systems 1991, page 92); and non-steroidal anti-inflammatory agents such as diclofenac sodium, indomethacin and phenylbutazone (Yamashita et al., J. Pharm. Pharmacol. 1987, 39, 621-626).

As used herein, "carrier compound" as used in the context of the oligonucleotides of the present invention, refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 1995, 6, 698-708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved.

Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ found to be effective in vitro and in in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to weekly, or monthly, or yearly.

siRNA Therapy

In general terms, RNA interference (RNAi) is the process whereby the introduction of double stranded RNA into a cell inhibits the expression of a gene corresponding to its own sequence. RNAi is usually described as a post-transcriptional gene-silencing (PTGS) mechanism in which dsRNA triggers degradation of homologous messenger RNA in the cytoplasm. The mediators of RNA interference are 21- and 23-nucleotide small interfering RNAs (siRNA) (Elbashir, S. M. et al., (2001), Genes Dev. 15, 188-200; Elbashir, S. M. et al. (2001), Nature 411: 494-498; Hutvagner, G. et al., (2001), Science 293:834-838). In a second step, siRNAs bind to a ribonuclease complex called RNA-induced silencing complex (RISC) that guides the small dsRNAs to its homologous mRNA target. Consequently, RISC cuts the mRNA approximately in the middle of the region paired with the antisense siRNA, after which the mRNA is further degraded. A ribonuclease III enzyme, dicer, is required for processing of long dsRNA into siRNA duplexes (Bernstein, E. et al. ((2001), Nature 409: 363-366).

Mechanism of RNAi

The only RNA molecules normally found in the cytoplasm of a cell are molecules of single-stranded mRNA. If the cell finds molecules of double-stranded RNA (dsRNA), it uses a ribonuclease III enzyme, dicer, for processing of long dsRNA into siRNA duplexes (Bernstein, E. et al. ((2001), Nature 409: 363-366) containing ~22 base pairs (~2 turns of a double helix). Dicer is a bidentate RNase III, which also contains an ATP-dependent RNA helicase domain and a PAZ domain, presumably important for dsRNA unwinding and mediation of protein-protein interactions, respectively ((Bernstein, E. et al. ((2001), Nature 409: 363-366). Dicer is evolutionarily conserved in worms, flies, plants, fungi and mammals, and has a second cellular function important for the development of these organisms (Grishok, A. (2001), Cell 106:23-34; Knight, S. W. et al. (2001), Science 293:2269-2271; Hutvagner, G. et al., (2001), Science 293:834-838). At present, it is uncertain whether dicer activity in species other than *D.melanogaster* produces siRNAs of predominantly 21 nt in length. The estimates of siRNA size vary in the literature between 21 and 25 nt (Hamilton, A. J. et al. (1999), Science 286: 950-952; Zamore, P. D. et al. (2000), Cell 101: 25-33; Elbashir, S. M. et al., (2001), Genes Dev. 15, 188-200; Elbashir, S. M. et al. (2001), Nature 411: 494-498; Hammond, S. M. et al. (2000), Nature 404: 293-296; Hutvagner, G. et al., (2001), Science 293:834-838).

The two strands of each fragment then separate enough to expose the antisense strand so that it can bind to the complementary sense sequence on a molecule of mRNA. In RNAi, a siRNA-containing endonuclease complex cleaves a single-stranded target RNA in the middle of the region complementary to the 21 nt guide siRNA of the siRNA duplex (Elbashir, S. M. et al., (2001), Genes Dev. 15, 188-200; Elbashir, S. M. et al. (2001), Nature 411: 494-498). This cleavage site is one helical turn displaced from the cleavage site that produced the siRNA from long dsRNA, suggesting dramatic conformational and/or compositional changes after processing of long dsRNA to 21 nt siRNA duplexes. The target RNA cleavage products are rapidly degraded because they either lack the stabilizing cap or poly(A) tail. A protein component of the ~500 kDa endonuclease or RNA-induced silencing complex (RISC) was recently identified and is a member of the argonaute family of proteins (Hammond, S. M. et al. (2001) Science 293: 1146-1150), however, it is currently unclear whether dicer is required for RISC activity. Thus, the cleavage of the mRNA destroys its ability to be translated into a polypeptide. Because of their action, these fragments of RNA have been named "short (or small) interfering RNA" (siRNA).

Introducing dsRNA corresponding to a particular gene will knock out the cell's own expression of that gene. This can be done in particular tissues at a chosen time. This often provides an advantage over conventional gene "knockouts" where the missing gene is carried in the germline and thus whose absence may kill the embryo before it can be studied.

Although it has been suggested that the one disadvantage of simply introducing dsRNA fragments into a cell is that gene expression is only temporarily reduced, it has recently been shown that the system can be manipulated using a DNA vector such that the siRNA molecule can be continuously synthesized for prolonged periods of time in order to continue in suppression of the desired gene (Brummelkamp et. al. 19 Apr. 2002, Science). After two months, the cells still failed to manufacture the protein whose gene had been turned off by RNAi. Effective siRNA molecules may be designed using the following guidelines:

In general, siRNA oligonucleotides should be about 21 nucleotides in length with 2 nucleotide overhangs, usually 3' TT.

Sequences located in the 5' or 3' UTR of the mRNA target and nearby the start codon should be avoided, as they may be richer in regulatory protein binding sites.

Search for a sequence AA(N19)TT or AA(N21) with approximately 50% G/C content.

Compare the selected siRNA nucleotide sequence against databases to ensure that only one gene will be targeted.

Target recognition is a highly sequence specific process, mediated by the siRNA complementary to the target. One or two base pair mismatches between the siRNA and the target gene will greatly reduce the silencing effect. It might be necessary to test several sequences since positional effects of siRNAs have been reported.

The 3'-most nucleotide of the guide siRNA does not contribute to the specificity of target recognition, while the penultimate nucleotide of the 3' overhang affects target RNA cleavage and a mismatch reduces RNAi 2- to 4-fold. The 5' end of the guide siRNA also appears more permissive for mismatched target RNA recognition when compared with the 3' end. Nucleotides in the center of the siRNA, located opposite to the target RNA cleavage site, are important specificity determinants and even single nucleotide changes reduce RNAi to undetectable levels. This suggests that siRNA duplexes may be able to discriminate mutant or polymorphic alleles in gene targeting experiments, which may become an important feature for future therapeutic developments.

Double-stranded RNA has been shown to attenuate specific gene expression in *C. elegans, Drosophila* and *Trypanosoma* brucei (M. Montgomery, et al., Proc. Natl. Acad. Sci. U.S.A. 95, 15502-15507 (1998); J. Kennerdell et al., Cell 95, 1017-1026 (1998); H. Ngo et al., Proc. Natl. Acad. Sci. U.S.A. 95, 14687-14692 (1998)). The types of genes attenuated in these invertebrates include some encoding transcription factors and others that encode growth factor receptors. There is also evidence that double-stranded RNA may effectively silence gene expression in plants (M. Wassenegger et al., Plant. Mol. Biol. 37, 349-362 (1998); P. Watergiyse et al., Proc. Natl. Acad. Sci. U.S.A. 95, 13959-13964 (1998)).

A definitive mechanism through which double-stranded RNA effects gene silencing remains has not been identified (M. Montgomery et al., Trends Genet. 14, 255-258 (1998)). Recently, Montgomery et al. reported that double-stranded RNA induces specific RNA degradation in nematodes (Proc. Natl. Acad. Sci. U.S.A. 95, 15502-15507 (1998)). This conclusion was based upon the fact that DNA sequences in the targeted regions of the gene were not altered and that 100% of the F2 generation reverted to the wild type phenotype. In addition, *C. elegans* has a unique genetic organization. Genes in this animal are organized in operons in which a single promoter controls expression of a number of genes. They showed that the double-stranded RNA affects only expression of the targeted gene. In contrast, however, others have observed heritable effects of double-stranded RNA on the expression of a number of genes in *C. elegans*, suggesting that more than one mechanism may be involved in double-stranded RNA-mediated inhibition of gene activity (H. Tahara, Science 28, 431-432 (1998)).

The present invention provides a method for attenuating gene expression in a cell using gene-targeted double-stranded RNA (dsRNA). The dsRNA contains a nucleotide sequence that is essentially identical to the nucleotide sequence of at least a portion of the target gene, in the matter of the present invention, the genes encoding CXCL12 or CXCR4. The cell into which the dsRNA is introduced is preferably a cell containing at least one CXCL12 or CXCR4 gene to which the dsRNA is targeted. Gene expression can be attenuated in a whole organism, an organ or tissue of an organism, including a tissue explant, or in cell culture. Preferably, the cell is a mammalian cell, and preferably the mammal is a human, although other non-human mammals are contemplated. Double-stranded RNA is introduced directly into the cell or, alternatively, into the extracellular environment from which it is taken up by the cell. Inhibition is specific for the targeted gene. Depending on the particular target gene and the dose of dsRNA delivered, the method may partially or completely inhibit expression of the gene in the cell. The expression of two or more genes can be attenuated concurrently by introducing two or more double stranded RNAs into the cell in amounts sufficient to attenuate expression of their respective target genes. Double stranded RNAs that are administered "concurrently" are administered, together or separately, so as to be effective at generally the same time.

In yet another aspect, the invention provides a method for attenuating the expression of a CXCL12 or CXCR4 gene in a cell that includes annealing two complementary single stranded RNAs in the presence of potassium chloride to yield double stranded RNA; contacting the double stranded RNA with RNAse to purify the double stranded RNA by removing single stranded RNA; and introducing the purified double stranded RNA into the cell in an amount sufficient to attenuate expression of the target gene.

The invention further provides a method for mobilizing hematopoietic stem cells from the bone marrow or for treating or preventing a hyperproliferative condition or a cancerous condition in a mammal by increasing the mobilization or egress of a cancer stem cell from its niche in the microenvironment or from a tumor mass, thereby bringing the cancer stem cell from a quiescent state to a proliferating state and thus more sensitive to treatment with cytoreductive therapies. Double stranded RNA is administered to the mammal in an amount sufficient to attenuate expression of the CXCL12 or CXCR4 gene, the expression of which is associated with the cancerous condition. Concurrent inhibition of multiple genes is advantageous to treat diseases associated with multiple genes, or to treat two or more diseases or infections concurrently.

The present invention provides a method for gene silencing in organisms and cells, especially mammals, using gene-specific double-stranded RNA. The ability to use double-stranded RNA to specifically block expression of particular genes in a multicellular setting both in vivo and in vitro has broad implications for the study of numerous diseases, in the matter of the present invention, cancerous consitions.

The method of the present invention allows for attenuation of gene expression in a cell. "Attenuation of gene expression" can take the form of partial or complete inhibition of gene function Mechanistically, gene function can be partially or completely inhibited by blocking transcription from the gene to mRNA, or by blocking translation of the mRNA to yield the protein encoded by the gene, although it should be understood that the invention is not limited to any particular mechanism of attenuation of gene expression. Inhibition of gene function is evidenced by a reduction or elimination, in the cell, of the activity associated with the protein encoded by the gene. Whether and to what extent gene function is inhibited can be determined using methods known in the art. For example, in many cases inhibition of gene function leads to a change in phenotype which is revealed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Attenuation of gene expression can be quantified, and the amount of attenuation of gene expression in a treated cell compared to a cell not treated according to the present invention can be determined. Lower doses dsRNA may result in inhibition in a smaller fraction of cells, or in partial inhibition in cells. In addition, attenuation of gene expression can be time-dependent; the longer the period of time since the administration of the dsRNA, the less gene expression may be attenuated. Attenuation of gene expression can occur at the level of transcription (i.e., accumulation of mRNA of the targeted gene), or translation (i.e., production of the protein encoded by the targeted gene). For example, mRNA from the targeted gene can be detected using a hybridization probe having a nucleotide sequence outside the region selected for the inhibitory double-stranded RNA, and translated polypeptide encoded by the target gene can be detected via Western blotting using an antibody raised against the polypeptide. It should be noted that the method of the invention is not limited to any particular mechanism for reducing or eliminating cellular protein activity; indeed, as noted above, it is not yet fully understood how the introduction of dsRNA into a cell causes attenuation of expression of the targeted gene, nor is it known whether single or multiple mechanisms are at work.

The attenuation of gene expression achieved by the method of the invention is specific for CXCL12 or CXCR4. In other words, the dsRNA inhibits at least one of the target genes without manifesting effects on other genes of the cell.

Double-Stranded RNA

The dsRNA is formed from one or more strands of polymerized ribonucleotide. When formed from only one strand, it takes the form of a self-complementary hairpin-type molecule that doubles back on itself to form a duplex. When formed from two strands, the two strands are complementary RNA strands. The dsRNA can include modifications to either the phosphate-sugar backbone or the nucleoside. For example, the phosphodiester linkages of natural RNA may be modified to include at least one of a nitrogen or sulfur heteroatom. Likewise, bases may be modified to block the activity of adenosine deaminase.

The nucleotide sequence of the dsRNA is defined by the nucleotide sequence of its targeted gene, CXCL12 (SEQ ID NO: 23) or CXCR4 (SEQ ID NO: 24). The dsRNA contains a nucleotide sequence that is essentially identical to at least a portion of the target gene; preferably the dsRNA contains a nucleotide sequence that is completely identical to at least a portion of the target gene. It should be understood that in comparing an RNA sequence to a DNA sequence, an "identical" RNA sequence will contain ribonucleotides where the DNA sequence contains deoxyribonucleotides, and further that the RNA sequence will contain a uracil at positions where the DNA sequence contains thymidine. More preferably, the dsRNA that is completely identical to at least a portion of the target gene does not contain any additional nucleotides.

A dsRNA that is "essentially identical" to a least a portion of the target gene is a dsRNA wherein one of the two complementary stands (or, in the case of a self-complementary RNA, one of the two self-complementary portions) is either identical to the sequence of that portion of the target gene or contains one or more insertions, deletions or single point mutations relative to the nucleotide sequence of that portion of the target gene. The invention thus has the advantage of being able to tolerate sequence variations that might be expected due to genetic mutation, strain polymorphism, or evolutionary divergence. Alternatively, a dsRNA that is "essentially identical" to at least a portion of the target gene can be functionally as a dsRNA wherein one of the two complementary strands (or, in the case of a self-complementary RNA, one of the two self-complementary portions) is capable of hybridizing with a portion of the target gene transcript (e.g., under conditions including 400 mM NaCl, 40 mM PIPES pH 6.4, 1 mM EDTA, 50° C. or 70° C. hybridization for 12-16 hours; followed by washing).

The dsRNA nucleotide sequence that is essentially or completely identical to at least a portion of the target gene has a length of preferably at least about 5-10 bases, more preferably 10-bases, more preferably at least about 50 bases, and most preferably at least about 100 bases. The dsRNA nucleotide sequence has a length of preferably less than about 400 bases, more preferably less than about 300 base, more preferably less than about 200 bases and most preferably less than about 100 bases. It will be understood that the length of the dsRNA, the degree of homology necessary to affect gene expression, and the most effective dosages can be optimized for each particular application using routine methods.

Synthesis of dsRNA

Single strands of RNA are synthesized in vitro. Preferably, single stranded RNA is enzymatically synthesized from the PCR products of a DNA template, preferably a cloned a cDNA template. Provided the sequence of the target gene is known, e.g. CXCL12 or CXCR4, a cloned cDNA template can be readily made from target cell RNA using reverse-transcriptase polymerase chain reaction (RT-PCR) to generate a cDNA fragment, following by cloning the cDNA fragment into a suitable vector. Preferably, the vector is designed to allow the generation of complementary forward and reverse PCR products. The vector pGEM-T (Promega, Madison Wis.) is well-suited for use in the method because it contains a cloning site positioned between oppositely oriented promoters (i.e., T7 and SP6 promoters; T3 promoter could also be used). After purification of the PCR products, complementary single stranded RNAs are synthesized, in separate reactions, from the DNA templates via RT-PCR using two different RNA polymerases (e.g., in the case of pGEM-T, T7 polymerase and SP6 polymerase). RNAse-free DNAse is added to remove the DNA template, then the single-stranded RNA is purified. Single strands of RNA can also be produced enzymatically or by partial/total organic synthesis. The use of in vitro enzymatic or organic synthesis allows the introduction of any desired modified ribonucleotide. The RNA strands may or may not be polyadenylated; and the RNA strands may or may not be capable of being translated into a polypeptide by a cell's translational apparatus. Preferably, purification of RNA is performed without the use of phenol or chloroform.

Double stranded RNA is formed in vitro by mixing complementary single stranded RNAs, preferably in a molar ratio of at least about 3:7, more preferably in a molar ratio of about 4:6, and most preferably in essentially equal molar amounts (i.e., a molar ratio of about 5:5). Preferably, the single stranded RNAs are denatured prior to annealing, and the buffer in which the annealing reaction takes place contains a salt, preferably potassium chloride. Prior to administration, the mixture containing the annealed (i.e., double stranded) RNA is preferably treated with an enzyme that is specific for single stranded RNA (for example, RNAse A or RNAse T) to confirm annealing and to degrade any remaining single stranded RNAs. Addition of the RNAse also serves to excise any overhanging ends on the dsRNA duplexes.

Delivery of dsRNA to a Cell

Double stranded RNA can be introduced into the cell in a number of different ways. For example, the dsRNA is conveniently administered by microinjection; other methods of introducing nucleic acids into a cell include bombardment by particles covered by the dsRNA, soaking the cell or organism in a solution of the dsRNA, electroporation of cell membranes in the presence of the dsRNA, liposome-mediated delivery of dsRNA and transfection mediated by chemicals such as calcium phosphate, viral infection, transformation, and the like. The dsRNA may be introduced along with components that enhance RNA uptake by the cell, stabilize the annealed strands, or otherwise increase inhibition of the target gene. In the case of a cell culture or tissue explant, the cells are conveniently incubated in a solution containing the dsRNA or lipid-mediated transfection; in the case of a whole animal or plant, the dsRNA is conveniently introduced by injection or perfusion into a cavity or interstitial space of an organism, or systemically via oral, topical, parenteral (including subcutaneous, intramuscular and intravenous administration), vaginal, rectal, intranasal, ophthalmic, or intraperitoneal administration. In addition, the dsRNA can be administered via and implantable extended release device. Methods for oral introduction include direct mixing of RNA with food of the organism, as well as engineered approaches in which a species that is used as food is engineered to express an RNA, then fed to the organism to be affected. The dsRNA may be sprayed onto a plant or a plant may be genetically engineered to express the RNA in an amount sufficient to kill some or all of a pathogen known to infect the plant.

Alternatively, dsRNA can be supplied to a cell indirectly by introducing one or more vectors that encode both single strands of a dsRNA (or, in the case of a self-complementary RNA, the single self-complementary strand) into the cell. Preferably, the vector contains 5' and 3' regulatory elements that facilitate transcription of the coding sequence. Single stranded RNA is transcribed inside the cell, and, presumably, double stranded RNA forms and attenuates expression of the target gene. Methods for supplying a cell with dsRNA by introducing a vector from which it can be transcribed are set forth in WO 99/32619 (Fire et al., published 1 Jul. 1999). A transgenic animal that expresses RNA from such a recombinant construct may be produced by introducing the construct into a zygote, an embryonic stem cell, or another multipotent cell derived from the appropriate organism. A viral construct packaged into a viral particle would accomplish both efficient introduction of an expression construct into the cell and transcription of RNA encoded by the expression construct.

The dsRNA is typically administered in an amount that allows delivery of at least one copy per cell. The amount of dsRNA administered to a cell, tissue, or organism depends on the nature of the cell, tissue, or organism, the nature of the target gene, and the nature of the dsRNA, and can readily be optimized to obtain the desired level of gene inhibition. To attenuate gene expression in a single cell embryo, for example, at least about $0.8 \times 10^6$ molecules of dsRNA are injected; more preferably, at least about $20 \times 10^6$ molecules of dsRNA are injected; most preferably, at least about $50 \times 10^6$ molecules of dsRNA are injected. The amount of dsRNA injected into a single cell embryo is, however, preferably at most about $1000 \times 10^6$ molecules; more preferably, it is at most about $500 \times 10^6$ molecules, most preferably, at most about $100 \times 10^6$ molecules. In the case of administration of dsRNA to a cell culture or to cells in tissue, by methods other than injection, for example by soaking, electroporation, or lipid-mediated transfection, the cells are preferably exposed to similar levels of dsRNA in the medium. For example, 8-10 µL of cell culture or tissue can be contacted with about $20 \times 10^6$ to about $2000 \times 10^6$ molecules of dsRNA, more preferably about $100 \times 10^6$ to about $500 \times 10^6$ molecules of dsRNA, for effective attenuation of gene expression.

Once the minimum effective length of the dsRNA has been determined, it is routine to determine the effects of dsRNA agents that are produced using synthesized oligoribonucleotides. The administration of the dsRNA can be by microinjection or by other means used to deliver nucleic acids to cells and tissues, including culturing the tissue in medium containing the dsRNA.

The siRNA molecules of the present invention may be used to introduce dsRNA into a cell for the treatment or prevention of disease. To treat or prevent a disease or other pathology, a target gene is selected which is required for initiation or maintenance of the disease/pathology. The dsRNA can be introduced into the organism using in vitro, ex vivo or by in vivo methods. In an in vitro method, the dsRNA is introduced into a cell, which may or may not be a cell of the organism, and the dsRNA-containing cell is then introduced into the organism. In an ex vivo method, cells of the organism are explanted, the dsRNA is introduced into the explanted cells, and the dsRNA-containing cells are implanted back into the host. In an in vivo method, dsRNA is administered directly to the organism. As noted above, the dsRNA can also be delivered to a cell using one or more vectors that encode the complementary RNAs (or self-complementary RNA), which are then transcribed inside the cell and annealed to yield the desired dsRNA.

In medical applications, the dsRNA may be introduced into a cancerous cell or tumor, and thereby inhibit expression of a gene required for maintenance of the carcinogenic/tumorigenic phenotype.

Pharmaceutical Compositions

In some embodiments, the invention provides pharmaceutical compositions containing one or more adrenergic receptor agonists in combination with one or more agents that decrease the expression of CXCL12 or with one or more CXCR4 antagonists. In one embodiment, such compositions include one or more adrenergic receptor agonists and one or more agents that decrease the expression of CXCL12 or that block or antagonize CXCR4 in a therapeutically or prophylactically effective amount sufficient to alter bone marrow progenitor or stem cell growth, and a pharmaceutically acceptable carrier. In another embodiment, the composition includes one or more adrenergic receptor agonists and one or more agents that decrease the expression of CXCL12 or that block or antagonize CXCR4 in a therapeutically or prophylactically effective amount sufficient to inhibit a cytotoxic effect of a cytotoxic agent, such as cytotoxic agents used in chemotherapy or radiation treatment of cancer, and a pharmaceutically acceptable carrier. In a particular embodiment, the agents and pharmaceutical compositions are formulated for pharmaceutical or veterinary use. In one embodiment, the subject to be treated is a human or a non-human mammal. In a preferred embodiment, the subject to be treated is a human.

A "therapeutically effective amount" refers to an amount effective, at dosages and for periods of time necessary, to achieve the desired therapeutic result, in the manner of the present invention, such as enhanced mobilization of hematopoietic stem cells or progenitor cells from the bone marrow to the peripheral circulation, or alternatively, to enhance mobilization of cancer stem cells from their niche so as to promote their proliferation, thus making them more susceptible to killing by cytoreductive therapy. A therapeutically effective amount of an adrenergic receptor agonist, antagonist, or stem cell mobilizer, or chemotherapeutic therapy or modality may vary according to factors such as the disease state, age, sex, and weight of the individual, and the ability of the agent to elicit a desired response in the individual. Dosage regimens may be adjusted to provide the optimum therapeutic response. A therapeutically effective amount is also one in which any toxic or detrimental effects of the agent are outweighed by the therapeutically beneficial effects.

A "prophylactically effective amount" refers to an amount effective, at dosages and for periods of time necessary, to achieve the desired prophylactic result. Typically, a prophylactic dose is used in subjects prior to or at an earlier stage of disease, so that a prophylactically effective amount may be less than a therapeutically effective amount.

In particular embodiments, a preferred range for therapeutically or prophylactically effective amounts of either the agent that decreases the expression of CXCL12 or that blocks or antagonizes CXCR4 or the agent that acts as an adrenergic receptor agonist or antagonist may be determined by those skilled in the art using standard procedures, for example, in animal testing prior to proceeding into humans. It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners.

The amount of active compounds in the composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In some embodiments, one or more adrenergic receptor agonists may be formulated in pharmaceutical compositions with additional active ingredients, or administered in methods of treatment in conjunction with treatment with one or more additional medications, such as an agent as described herein that increases mobilization of stem cells, for example, an agent that decreases expression or function of CXCL12, or a CXCR4 antagonist, or one or more agents selected from the group consisting of: recombinant-methionyl human. G-CSF (Neupogen®, Filgastim; Amgen), GM-CSF (Leukine®., Sargramostim; Immunex), erythropoietin (rhEPO, Epogen®; Amgen), thrombopoietin (rhTPO; Genentech), interleukin-11 (rhIL-11, Neumega®; American Home Products), Flt3 ligand (Mobista; Immunex), multilineage hematopoietic factor (MARstem™; Maret Pharm.), myelopoietin (Leridistem; Searle), IL-3, myeloid progenitor inhibitory factor-1 (Mirostipen; Human Genome Sciences), and stem cell factor (rhSCF, Stemgen®; Amgen).

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the CXCR4 antagonists may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, an agent of the invention as described above may be formulated with one or more additional compounds that enhance the solubility of these agents. The invention also extends to such derivatives of such agents of the invention.

Derivatives of the agents such as those that decrease expression of CXCL12 or those that block or antagonize CXCR4 may include derivatives such as C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine residue is replaced with a phenethylamide analogue (e.g., Ser-Ile-phenethylamide as an analogue of the tripeptide Ser-Ile-Phe). The invention also extends to such derivatives of the novel antagonists of the invention.

Alternatively, a peptidic structure (such as an CXCL12 derived peptide) may be coupled directly or indirectly to at least one modifying group. Such modified peptides are also within the scope of the invention. The term "modifying group" is intended to include structures that are directly attached to the peptidic structure (e.g., by covalent coupling), as well as those that are indirectly attached to the peptidic structure (e.g., by a stable non-covalent association or by covalent coupling to additional amino acid residues, or mimics/mimetics, analogues or derivatives thereof, which may flank the CXCL12 core peptidic structure). For example, the modifying group can be coupled to the amino-terminus or carboxyterminus of a CXCL12 peptidic structure, or to a peptidic or peptidomimetic region flanking the core domain. Alternatively, the modifying group can be coupled to a side chain of at least one amino acid residue of a CXCL12 peptidic structure, or to a peptidic or peptido-mimetic region flanking the core domain (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, carbamate or urea bonds.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Materials and Methods

While the material and methods provided below have been employed for obtaining the results shown in Examples 1-13, it is to be understood that the same methods may be used to carry out the studies proposed in the remaining examples.

Animals $Cgt^{+/+}$, $^{+/-}$ and $^{-/-}$ littermate mice, backcrossed 7 generations into the C57BL/6 background, were used for experiments performed between 3 to 4 weeks of age. Genotype was determined at weaning by PCR as described (Coetzee, T., Fujita, N., Dupree, J., Shi, R., Blight, A., Suzuki, K., and Popko, B. (1996). Myelination in the absence of galactocerebroside and sulfatide: normal structure with abnormal function and regional instability. Cell 86, 209-219). C57BL/6-CD45.1 congenic mice were purchased from Charles River Laboratories (Frederick Cancer Research Center, Frederick, Md.). Dbh littermate mice were bred and rescued with L-threo-3,4-dihydroxyphenylserine (L-DOPS, Sumitomo Pharmaceuticals, Osaka, Japan) as described in supplemental Experimental Procedures. Mice were housed at Mount Sinai School of Medicine where experimental procedures were approved by the IACUC.

Mobilization of Hematopoietic Progenitors

To induce HSPC mobilization, mice were injected with recombinant human G-CSF (Filgrastim, Amgen, Thousand Oaks, Calif., 250 µg/kg/day, every 12 hours, 8 divided doses, s.c.) in PBS supplemented with 0.1% endotoxin free bovine serum albumin (BSA) or fucoidan (Sigma; 2 doses of 100 mg/kg with 2 h interval, i.p.) in PBS. Blood was harvested 3 h (G-CSF) or 1 h (fucoidan). CFU-C assays were carried out as previously described (Katayama, Y., and Frenette, P. S. (2003). Galactocerebrosides are required postnatally for stromal-dependent bone marrow lymphopoiesis. Immunity 18, 789-800).

Intracerebroventricular G-CSF Infusion:

A chronic guide cannula (1.0 mm) was implanted stereotaxically into the lateral ventricle (coordinates AP, −0.7 mm; DV, −2.4 mm; ML, 1.5 mm, from bregma). One week after implantation, mice received a reduced dose of G-CSF (25 µg/kg daily for 4 doses) either by ICV infusion (rate: 0.4 µL/min) or by s.c. injection.

Pharmacological Disruption or Induction of SNS-signals:

Newborn C57BL/6 mice were injected s.c. with 6OHDA (100 mg/kg, Sigma) or vehicle (saline) on postnatal days 2, 4, 6, 8 and 9. HSPC mobilization was induced at 3 weeks of age. For SNS disruption in adult C57BL6 mice, 4 week-old animals were injected i.p. with 2 doses of 6OHDA or vehicle, 100 mg/kg on day 0, 250 mg/kg on day 2, and G-CSF treatment was begun on day 5. For β-adrenergic receptor blockade, 4 week-old C57BL/6 mice were treated with propranolol (0.5 g/L in drinking water, Sigma) or control pure water for 3 weeks prior to mobilization. For rescue experiments, clenbuterol (2 mg/kg/day, i.p.) was injected starting day −2 prior to and continued during G-CSF treatment.

Generation of Chimeric Mice

Chimeric mice were generated by injection of $1 \times 10^6$ $Cgt^{+/+}$ or $^{-/-}$ mice (CD45.2) BMNCs into lethally irradiated (12 Gy, split dose) C57BL/6-CD45.1 congenic mice (Frenette and Weiss, 2000).

Migration Assay and Enzymatic Release

Transwell migration and elastase release assays were performed as described (Hidalgo, A., Peired, A. J., Weiss, L. A., Katayama, Y., and Frenette, P. S. (2004). The integrin alpha-Mbeta2 anchors hematopoietic progenitors in the bone marrow during enforced mobilization. Blood 104, 993-1001).

ELISA

CXCL12 ELISA was done exactly as described (Petit, I., Szyper-Kravitz, M., Nagler, A., Lahav, M., Peled, A., Habler, L., Ponomaryov, T., Taichman, R. S., Arenzana-Seisdedos, F., Fujii, N., et al. (2002). G-CSF induces stem cell mobilization by decreasing bone marrow SDF-1 and up-regulating CXCR4. Nat Immunol 3, 687-694). Mouse plasma osteocalcin was measured using ELISA kit (Biomedical Technologies Inc., Stoughton, Mass.) according to manufacturer's recommendation.

Flow Cytometry and Immunofluorescence Microscopy

Rat anti-mouse CD16/CD32 (clone 2.4G2), Ter119, Gr-1 (clone RB6-6-8C5), CD11b (clone M1/70), B220 (clone RA3-6B2), PE-c-kit (clone 2B8) and FITC-Sca-1 (clone E13-161.7) were from BD Pharmingen (San Diego, Calif.). Rat anti-CD3ε (clone C363.29B) was from SouthernBiotech (Birmingham, Ala.). Cy5-goat anti-rat IgG was purchased from Jackson Immunoresearch (West Grove, Pa.). Biotin-anti-IL-7R and PE-Cy5-streptavidin were from eBioscience (San Diego, Calif.).

For LSK ($lin^{neg}IL-7R^{neg}Sca-1^{pos}c-kit^{pos}$) and CLP ($lin^{neg}IL-7R^{pos}Sca-1^{low}c-kit^{low}$) analyses, BM cells from 3-week-old $Cgt^{+/+}$ or $^{-/-}$ mice were incubated in PBS containing 0.5% BSA and 2 mM EDTA (PEB) with mAb against CD16/CD32 and lineage antigens (Ter119, CD3ε, CD11b, B220 and Gr-1) followed by Cy5-anti-rat IgG. Potential non-specific binding to Cy5-anti-rat IgG secondary antibody was blocked by rat IgG (Sigma), and cells were further stained for FITC-Sca-1, PE-c-kit, and biotin-IL-7R followed by PE-Cy5-streptavidin. RBCs were lysed in 0.8% $NH_4Cl$ lysis buffer and the remaining BMNCs were washed twice in PEB. Analysis was performed on FACSCalibur with CellQuest software (Becton Dickinson, Mountain View, Calif.).

Bone Protein Extraction, Catecholamine Measurements, and Western Blot Analyses

Protein extraction from bone, biogenic amine determination, and BM, and CXCL12 immunoblotting were carried out as detailed in supplemental Experimental Procedures.

RNA Extraction and Q-PCR

Methods, primers and PCR conditions are available in Table S3. Briefly, total RNA was extracted from BMNC using TRIzol solution (Invitrogen, Carlsbad, Calif.). The bone carcass was then immersed in liquid nitrogen, and pulverized into powder followed by RNA extraction with TRIzol. Total RNA (1 µg) was treated with DNaseI (Invitrogen, Carlsbad, Calif.), and reverse transcribed using first strand cDNA synthesis with random primers (Promega, Madison, Wis.). Q-PCR was performed using SYBR Green (Molecular Probes) on an ABI PRISM 7900HT Sequence Detection System (Applied Biosystems, Foster city, CA). Primers and PCR conditions are shown in Table S3. All experiments were done in triplicate and normalized to GAPDH.

Generation of $Dbh^{-/-}$ Animals:

Dbh mice were hybrids of C57BL6 and 129/SvCPJ. $Dbh^{+/-}$ females were mated with $Dbh^{-/-}$ males and treated with 100 µg/ml each of phenylephrine and isoproterenol (Sigma, St. Louis, Mo.) from embryonic day (E)9.5 to E16.5, and 2 mg/ml of L-threo-3,4-dihydroxyphenylserine (L-DOPS, Sumitomo Pharmaceuticals, Osaka, Japan) from E16.5 to birth in the maternal drinking water to enhance fetal survival of the $Dbh^{-/-}$ mice (Thomas, S. A., Matsumoto, A. M., and Palmiter, R. D. (1995). Noradrenaline is essential for mouse fetal development. Nature 374, 643-646). Sex-matched littermate $Dbh^{+/-}$ mice were used as controls because they have normal tissue levels of norepinephrine/epinephrine and are phenotypically indistinguishable from $Dbh^{+/+}$ mice (Thomas, S. A., Marck, B. T., Palmiter, R. D., and Matsumoto, A. M. (1998). Restoration of norepinephrine and reversal of phenotypes in mice lacking dopamine beta-hydroxylase. J Neurochem 70, 2468-2476).

Western Blot Analyses

PBS or BMEF (35 µl) from G-CSF-treated and control mice was incubated with 50 ng of rhCXCL12α (R&D Systems) for 24 h at 37° C. The reactions were stopped by the addition of sample buffer containing protease inhibitor cocktail (Sigma) and DTT (final concentration 10 mM) followed by boiling for 5 min at 95° C. Samples were separated by electrophoresis on 16% polyacrylamide Tris-tricine gel and transferred onto PVDF membrane (0.2 µm pore size, Millipore, Bedford, Mass.). Membranes were blocked in TBS with 0.05% Tween 20 and 4% milk, incubated with 0.5 µg/ml of mouse monoclonal anti-CXCL12 antibody (clone 79018.111, R&D Systems) then with 1/20,000 dilution of horseradish peroxidase-anti-mouse IgG (Jackson Immunoresearch, West Grove, Pa.). Signal was detected with the enhanced chemiluminescence method (West Dura Extended Duration Substrate, Pierce, Rockford, Ill.).

Protein Extraction from Bone and Bone Marrow

BMEF was obtained by flushing two femurs with one ml of ice-cold PBS, and the supernatant was harvested after 25 strokes of gentle pipetting followed by centrifugation at 400 g for 5 min. Bone protein extraction was performed as described (Pfeilschifter, J., Laukhuf, F., Muller-Beckmann, B., Blum, W. F., Pfister, T., and Ziegler, R. (1995). Parathyroid hormone increases the concentration of insulin-like growth factor-I and transforming growth factor beta I in rat bone. J Clin Invest 96, 767-774). After extraction, the samples were dialyzed extensively against cold PBS (pH 7.4) for 72 h with a dialysis cassette of 3500 MWCO (Pierce). Volume of dialyzed extracts was measured, centrifuged at 16,000 g for 15 min at 4° C., and the supernatants stored at −80° C. CXCL12 levels in BMEF and bone extracts were determined by ELISA.

Catecholamine Measurements

Mice were sacrificed and hearts were rapidly removed, weighed, frozen in liquid nitrogen. Tissues were homogenized in HPLC solvent (0.1M TCA, which contains $10^{-2}$ M sodium acetate, $10^{-4}$ M EDTA and 10.5% methanol, pH 3.8). Hindlimb long bones were harvested, weighted, frozen in liquid nitrogen. Pooled bones were crushed using a bessman tissue pulverizer (Spectrum Laboratories) pre-chilled in a liquid nitrogen bath. Pulverized tissues were homogenized (620 mg/ml) in 0.4N $HClO_4$ containing 0.84 mg/mL EDTA and 12.5 µL of 4% sodium pyrosulfite solution. Bone catecholamines were extracted using solid $Al_2O_3$ and then desorbed from the $Al_2O_3$ using 0.1 N acetic acid. NE levels were determined by HPLC at the Neurochemistry Core Lab, Vanderbilt University's Center for Molecular Neuroscience Research (Nashville, Tenn.).

Immunofluorescence Microscopy

For CXCL12 staining, femoral bones were directly frozen in OCT compound (Sakura Finetechnical, Tokyo, Japan), and sectioned at 8 µm thickness. Sections were fixed in ice-cold 5% acetic acid in ethanol for 15 min, incubated in 3% $H_2O_2$ in PBS to quench the endogenous peroxidase for 1 h, and blocked with 5% horse serum in PBS and Avidin/Biotin Blocking Kit (Vector Laboratories, Burlingame, Calif.) followed by the blocking with TNB blocking buffer (PerkinElmer, Boston, Mass.). Sections were incubated with goat anti-CXCL12 polyclonal antibody (Santa Cruz Biotechnology, Santa Cruz, Calif.) followed by biotinylated horse anti-goat IgG (Vector Laboratories). Signal was amplified by Vectastain Elite ABC Kit (Vector Laboratories) and visualized by Tyramide Signal Amplification kit for FITC (PerkinElmer). For dual color staining of osteocytes and CXCL12 in bone, samples were stained with rat anti-mouse CD44 (KM201, from ATCC) together with goat anti-CXCL12 polyclonal antibody (Santa Cruz). After the incubation with biotinylated horse anti-goat IgG (Vector Laboratories), goat IgG (Sigma) was used to block residual binding sites of this secondary antibody. CD44 and CXCL12 were visualized with FITC conjugated goat anti-rat IgG (Pierce) and Vectastain Elite ABC Kit (Vector Laboratories) followed by Tyramide Signal Amplification kit for Cy3 (PerkinElmer), respectively.

For the morphology of bone lining osteoblasts, femoral bones were fixed overnight in formalin, decalcified in 10% EDTA (pH 7.4) for 48 h, snap-frozen in isopentane chilled in liquid nitrogen, and sectioned at 10 µm thickness. Sections were fixed with 4% parafolmaldehyde for 20 min, stained with anti-CD44 (KM201) followed by donkey Alexa-488-anti-rat IgG (Molecular Probes, Eugene, Oreg.), and mounted in Vectashield Mounting Medium with DAPI (Vector Laboratories). TUNEL assay was done using an In Situ Cell Death Detection Kit (Roche Applied Science, Penzberg, Germany) according to manufacturer's recommendation. Images were captured and analyzed with Olympus BX61WI (Hauppauge, N.Y.) with 60× objective mounted on a motorized X, Y stage and a Z focusing drive (Applied Scientific Instrumentation, Eugene, Oreg.). Images are collected with Coolsnap HQ digital camera (Ropert Scientific, Munich, Germany). A Dell workstation with SlideBook software (Intelligent Imaging Innovations, Denver, Colo.) provided for synchronization of components, data acquisition and image deconvolution.

Cell Isolation and CFU Assays

Bone marrow cells are harvested by flushing femors aseptically in RPMI using a 21 gauge needle. A single-cell suspension is obtained by gently aspirating several times using the same needle and syringe. Splenocytes are extracted by homogenizing the spleen using 16, 18 and 21 gauge needles sequentially. The suspension volume is measured with a graduated pipette. CFU-GM are assayed as described (Frenette, P. S., and Weiss, L. (2000). Sulfated glycans induce rapid hematopoietic progenitor cell mobilization: evidence for selectin-dependent and independent mechanisms. Blood 96, 2460-2468). IL-7-dependent CFU-pre-B assays are done using Methocult M3630, and CFU-F are assayed in Mesen-Cult Basal Medium supplemented with Mesenchymal Stem Cell Stimulatory Supplement (StemCell Technologies, Vancouver, Canada).

Long-Term Bone Marrow Cultures

B-LTBMC are established as described (Whitlock and Witte, (1982), Long-term culture of B lymphocytes and their precursors from murine bone marrow, Proc Natl Acad Sci USA., June; 79(11):3608-12). In brief, $7 \times 10^6$ BM nucleated cells from 3-week-old littermates are harvested and inoculated into 6-well tissue culture plates (Corning, N.Y.) in RPMI supplemented with 5% fetal bovine serum (FBS) (StemCell Technologies), $5 \times 10^{-5}$ M2-mercaptoethanol, 100 U/ml penicillin, 100 ug/ml streptomycin, and 0-0.25 µg/ml amphotericin B. Cultures are incubated at 37° C. with 5% $CO_2$ and constant humidity, and are fed semiweekly from 1 week after the initiation by half medium change. M-LTBMC are established as described (Dexter, et al., (1977), Regulation of haemopoietic stem cell proliferation in long term bone marrow cultures, Biomedicine. December; 27(9-10):344-9) with minor modifications. In brief, $7 \times 10^6$ BM nucleated cells are inoculated into 6-well tissue culture plate in MyeloCult M5300 (StemCell Technologies), which contains 12.5% horse serum and 12.5% FBS, with $10^{-6}$ M hydrocortisone sodium succinate (Pharmacia & Upjohn, Kalamazoo, Mich.) and the above antibiotics. Cultures are incubated at 33° C. with 5% $CO_2$ and constant humidity. Cultures are fed at weekly intervals by half medium change.

Statistical Analysis

All values are reported as mean±SEM. Statistical significance for two unpaired groups was assessed by the Student's t test or Mann-Whitney U test. Significance was set at $p<0.05$.

Example 1

Mobilization is Severely Impaired in $Cgt^{-/-}$ Mice

Figure 1:
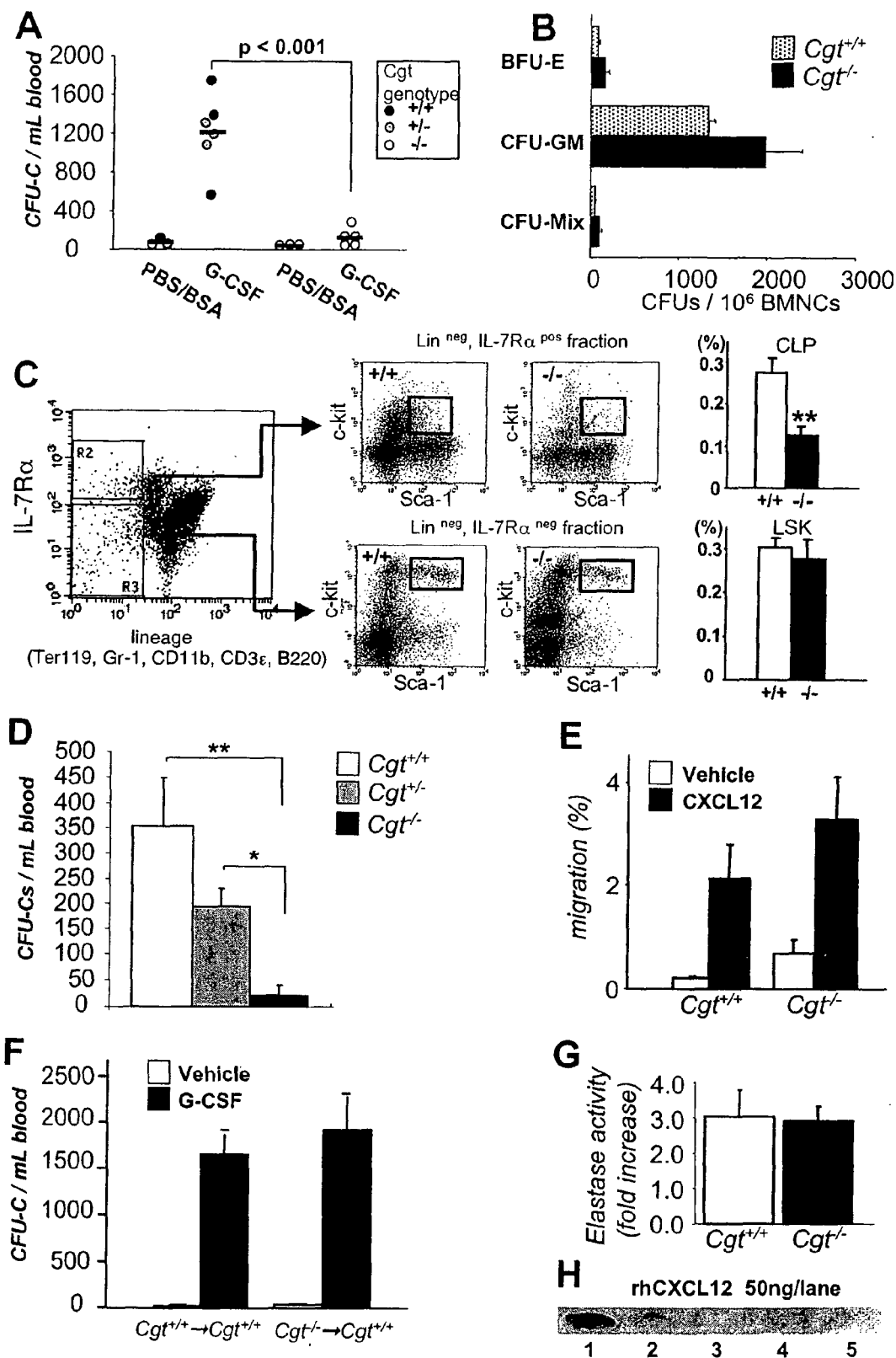
FIG. 1. Compromised mobilization in $Cgt^{-/-}$ mice despite normal BM proteolytic activity.
(A) G-CSF-induced mobilization in Cgt littermates. Each circle represents data from an individual mouse, and each bar is the mean.
(B) Frequency of CFU-Cs in steady-state BM from $Cgt^{+/+}$ and $^{-/-}$ mice. BFU-E, burst-forming units-erythroid. n=5.
(C) Numbers of CLPs ($Lin^{neg}$ $IL-7R^{pos}$ $Sca-1^{lo}$, $c-kit^{lo}$) and LSK cells ($Lin^{neg}$ $IL-7R^{neg}$ $Sca-1^{pos}$ $c-kit^{pos}$) in steady-state BM.
(D) Fucoidan-induced mobilization in Cgt littermates. n=5-19 mice.
(E) CXCL12-mediated migration. BMNCs from $Cgt^{+/+}$ or $^{-/-}$ mice were allowed to migrate for 4 h toward lower chamber containing 100 ng/ml CXCL12α; n=6 experiments.
(F) Mobilization phenotype does not result from $Cgt^{-/-}$ hematopoietic cells. CD45.1-congenic wild-type mice reconstituted with $Cgt^{+/+}$ or $^{-/-}$ BM were treated with control PBS/BSA or G-CSF, and the number of circulating CFU-Cs was assessed; n=34 mice.
(G) Release of elastase activity from BMNCs treated with vehicle or PMA (16 nM). Shown are mean±SEM fold increase in the PMA-treated group compared to the vehicle-treated group; n=3-5 mice.
(H) Degradation of rhCXCL12α by BMEF proteases. CXCL12α (50 ng) was incubated with control PBS (lane 1) or BMEF from PBS/BSA-treated $Cgt^{+/+}$ (lane 2), G-CSF-treated $Cgt^{+/+}$ (lane 3), PBS/BSA-treated $Cgt^{-/-}$ (lane 4), and G-CSF-treated $Cgt^{-/-}$ mice (lane 5). CXCL12α protein content was assessed by Western blotting. A representative of 2 experiments is shown. * p<0.05; ** p<0.01.

Cgt littermates were treated with G-CSF to elicit HSPCs from the BM. Strikingly, there was little mobilization in $Cgt^{-/-}$ mice compared to $Cgt^{+/-}$ or $^{+/+}$ littermates (FIG. 1A). The reduction of circulating HSPCs in $Cgt^{-/-}$ mice was not due to lower numbers of progenitors (FIG. 1B) or stem cells [FIG. 1C and [see (Katayama, Y., and Frenette, P. S. (2003). Galactocerebrosides are required postnatally for stromal-dependent bone marrow lymphopoiesis. Immunity 18, 789-800) for competitive reconstitution] in the BM. However, the number of common lymphoid progenitor (CLP) cells (Kondo, M., Weissman, I. L., and Akashi, K. (1997). Identification of clonogenic common lymphoid progenitors in mouse bone marrow. Cell 91, 661-672) was significantly reduced in $Cgt^{-/-}$ mice compared to $Cgt^{+/+}$ littermates (FIG. 1C), indicating that the previously reported block in lymphoid differentiation (Katayama, Y., and Frenette, P. S. (2003). Galactocerebrosides are required postnatally for stromal-dependent bone marrow lymphopoiesis. Immunity 18, 789-800), occurs before the CLP stage. To exclude the possibility that the lymphopenic state contributed to the impaired mobilization in $Cgt^{-/-}$ mice, we injected G-CSF in Rag $1^{-/-}$ and $IL7R\alpha^{-/-}$ mice, which have broad deficits in B and T cells. Circulating CFU-Cs were elicited at levels similar to those of wild-type mice (data not shown), indicating that the mobilization defect in $Cgt^{-/-}$ mice is unrelated to lymphopenia.

If fucoidan promoted HSPC mobilization by mimicking the function of endogenous sulfatide, we would expect that its administration in $Cgt^{-/-}$ mice might rescue the mobilization defect. To test this possibility, we treated Cgt littermates with fucoidan and assayed for circulating HSPCs. We found that CFU-Cs were not mobilized by fucoidan in $Cgt^{-/-}$ mice (FIG. 1D), suggesting that Cgt expression is necessary for mobilization triggered by either fucoidan or G-CSF.

Example 2

The Mobilization Defect Originates from the Stromal Compartment

It has been reported that HIV-1 entry into human intestinal epithelial cell lines can be blocked by either anti-GalCer or anti-CXCR4 mAbs, suggesting that CXCR4 can cooperate with GalCer during the fusion process (Delezay, O., Koch, N., Yahi, N., Hammache, D., Tourres, C., Tamalet, C., and Fantini, J. (1997). Co-expression of CXCR4/fusin and galactosylceramide in the human intestinal epithelial cell line HT-29. Aids 11, 1311-1318). We assessed the migration of $Cgt^{-/-}$ BM mononuclear cells toward CXCL12 to investigate whether the mobilization defect arose from CXCR4 dysfunction on $Cgt^{-/-}$ hematopoietic cells. However, $Cgt^{-/-}$ and $^{+/+}$ cells did not differ in CXCL12-mediated migration (FIG. 1E).

To evaluate further whether the defect in HSPC mobilization observed in $Cgt^{-/-}$ mice could originate from hematopoietic cells, $Cgt^{+/+}$ or $^{-/-}$ BM nucleated cells (BMNCs; CD45.2+) were transplanted into lethally irradiated wild-type CD45.1 congenic mice. G-CSF-induced mobilization was similar for highly chimeric (>95% of donor type) $Cgt^{+/+}$ and $^{-/-}$ mice (FIG. 1F). Thus, these results indicate that the mobilization defect cannot be transferred through the transplantation of BM-derived hematopoietic cells.

Example 3

G-CSF-induced Bone Marrow Proteolytic Activity is Preserved in $Cgt^{-/-}$ Mice

Previous studies have revealed that G-CSF induces proteolytic activity in the extracellular BM microenvironment, and that the released proteases, most notably neutrophil elastase, may play an important role in mobilization (Petit, I., Szyper-Kravitz, M., Nagler, A., Lahav, M., Peled, A., Habler, L., Ponomaryov, T., Taichman, R. S., Arenzana-Seisdedos, F., Fujii, N., et al. (2002). G-CSF induces stem cell mobilization by decreasing bone marrow SDF-1 and up-regulating CXCR4. Nat Immunol 3, 687-694; Levesque, J. P., Hendy, J., Takamatsu, Y., Simmons, P. J., and Bendall, L. J. (2003). Disruption of the CXCR4/CXCL12 chemotactic interaction during hematopoietic stem cell mobilization induced by GCSF or cyclophosphamide. J Clin Invest 111, 187-196). We found that neutrophil elastase activity in supernatants from phorbol-myristate acetate (PMA)-activated BMNCs was similar for $Cgt^{+/+}$ and $^{-/-}$ littermates (FIG. 1G), suggesting that $Cgt^{-/-}$ BMNCs have a normal capacity to produce and release this serine protease. To evaluate more globally the proteolytic environment in $Cgt^{-/-}$ mice, recombinant CXCL12 was incubated with BM extracellular fluid (BMEF) derived from PBS/BSA or G-CSF-treated mice, and the degradation of recombinant CXCL12 was assessed by immunoblotting. A slight degradation of CXCL12 by BMEF was observed in PBS/BSA-treated mice, but no change was observed for $Cgt^{+/+}$ and $^{-/-}$ mice (FIG. 1H, lanes 2 and 4), suggesting a normal production of proteolytic enzymes in the $Cgt^{-/-}$ BM microenvironment under basal conditions. Consistent with previous reports (Petit, I., Szyper-Kravitz, M., Nagler, A., Lahav, M., Peled, A., Habler, L., Ponomaryov, T., Taichman, R. S., Arenzana-Seisdedos, F., Fujii, N., et al. (2002). G-CSF induces stem cell mobilization by decreasing bone marrow SDF-1 and up-regulating CXCR4. Nat Immunol 3, 687-694; Levesque, J. P., Hendy, J., Takamatsu, Y., Simmons, P. J., and Bendall, L. J. (2003). Disruption of the CXCR4/CXCL12 chemotactic interaction during hematopoietic stem cell mobilization induced by GCSF or cyclophosphamide. J Clin Invest 111, 187-196), CXCL12 protein was completely degraded after incubation with BMEF from G-CSF-treated $Cgt^{+/+}$ mice (FIG. 1H, lane 3), and complete degradation also occurred with BMEF from G-CSF-treated $Cgt^{-/-}$ mice (FIG. 1H, lane 5). Thus, mobilization is impaired in $Cgt^{-/-}$ mice despite normal proteolysis in the BM.

Example 4

CXCL12 is Expressed in Bone

Figure 2:
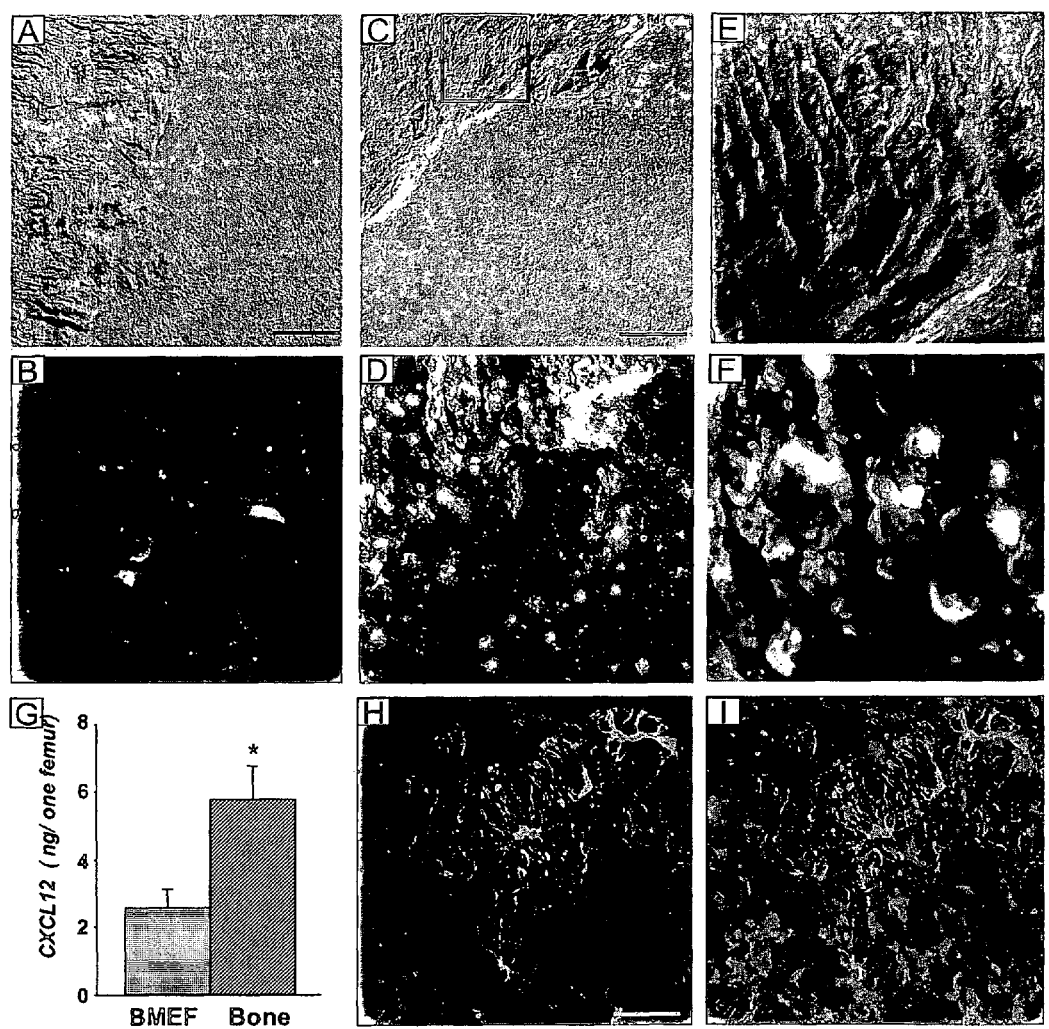
FIG. 2. Immunofluorescence staining of CXCL12 in BM and bone.
Wild-type fresh-frozen femoral bone transverse sections were stained with control goat IgG. (A-B) or anti-CXCL12 antibody (C-D), followed by sequential amplification steps. A and C are differential interference contrast (DIC) images of B and D shown to delineate bone and BM tissues. An area of bone (square) is highlighted in E (DIC) and F (CXCL12).
(G) CXCL12 protein levels determined by ELISA of BMEF and bone extracts from steady-state wild-type mice; n=8 mice per group, * p<0.05.
(H-I) Bone section stained for CD44 (green) to visualize osteocytes and CXCL12 (red). The composite image (I) shows no apparent co-localization of staining. Black bar, 50 µm; white bar, 20 µm.

CXCL12 has been reported to be expressed by endothelial cells and osteoblasts using immunohistochemical staining of human BM samples, but the positively stained area was limited and sporadic (Ponomaryov, T., Peled, A., Petit, I., Taichman, R. S., Habler, L., Sandbank, J., Arenzana-Seisdedos, F., Magerus, A., Caruz, A., Fujii, N., et al. (2000). Induction of the chemokine stromal-derived factor-1 following DNA damage improves human stem cell function. J Clin Invest 106, 1331-1339; Petit, I., Szyper-Kravitz, M., Nagler, A., Lahav, M., Peled, A., Habler, L., Ponomaryov, T., Taichman, R. S., Arenzana-Seisdedos, F., Fujii, N., et al. (2002). G-CSF induces stem cell mobilization by decreasing bone marrow SDF-1 and up-regulating CXCR4. Nat Immunol 3, 687-694). Knockin mice expressing GFP driven within the cxcl12 locus exhibited a speckled distribution of fluorescent stromal cells in the BM (Tokoyoda, K., Egawa, T., Sugiyama, T., Choi, B. I., and Nagasawa, T. (2004). Cellular niches controlling B lymphocyte behavior within bone marrow during development. Immunity 20, 707-718). We first performed standard immunofluorescence staining of CXCL12 in frozen sections of wild-type mouse BM but found no specific staining, likely due to the very low levels of CXCL12 in the BM (ng range in an entire femur) (Petit, I., Szyper-Kravitz, M., Nagler, A., Lahav, M., Peled, A., Habler, L., Ponomaryov, T., Taichman, R. S., Arenzana-Seisdedos, F., Fujii, N., et al. (2002). G-CSF induces stem cell mobilization by decreasing bone marrow SDF-1 and up-regulating CXCR4. Nat Immunol 3, 687-694; Levesque, J. P., Hendy, J., Takamatsu, Y., Simmons, P. J., and Bendall, L. J. (2003). Disruption of the CXCR4/CXCL12 chemotactic interaction during hematopoietic stem cell mobilization induced by GCSF or cyclophosphamide. J Clin Invest 111, 187-196). However, staining using the tyramide amplification system revealed a specific speckled staining in the BM parenchyma and, unexpectedly, strong and consistent staining in bone (FIG. 2A-F). Bone CXCL12 was not restricted to the endosteal region, a putative location of the stem cell niche (Zhang, J., Niu, C., Ye, L., Huang, H., He, X., Tong, W. G., Ross, J., Haug, J., Johnson, T., Feng, J. Q., et al. (2003). Identification of the haematopoietic stem cell niche and control of the niche size. Nature 425, 836-841; Calvi, L. M., Adams, G. B., Weibrecht, K. W., Weber, J. M., Olson, D. P., Knight, M. C., Martin, R. P., Schipani, E., Divieti, P., Bringhurst, F. R., et al. (2003). Osteoblastic cells regulate the haematopoietic stem cell niche. Nature 425, 841-846), but was distributed throughout the entire thickness. To confirm further the staining specificity, we compared the expression of CXCL12 between BMEF and protein extracts from bone by ELISA. Total CXCL12 was in fact higher in bone extracts than in BMEF (FIG. 2G), indicating that bone tissues are a major reservoir of CXCL12. To assess whether CXCL12 in bone was cell- or matrix-associated, we stained for CXCL12 and CD44, an osteocyte marker, but found no evidence of co-localization of the CXCL12 signal with osteocytes (FIG. 2H-I). However, primary osteoblasts and the osteoblast precursor cell line ST2 express high levels of CXCL12 [(Ponomaryov, T., Peled, A., Petit, I., Taichman, R. S., Habler, L., Sandbank, J., Arenzana-Seisdedos, F., Magerus, A., Caruz, A., Fujii, N., et al. (2000). Induction of the chemokine stromal-derived factor-1 following DNA damage improves human stem cell function. J Clin Invest 106, 1331-1339) and data not shown], indicating that CXCL12 is likely deposited in the bone matrix by osteoblasts but not osteocytes.

Example 5

Decreased CXCL12 Expression in Bone Correlates with Mobilization

Figure 3:
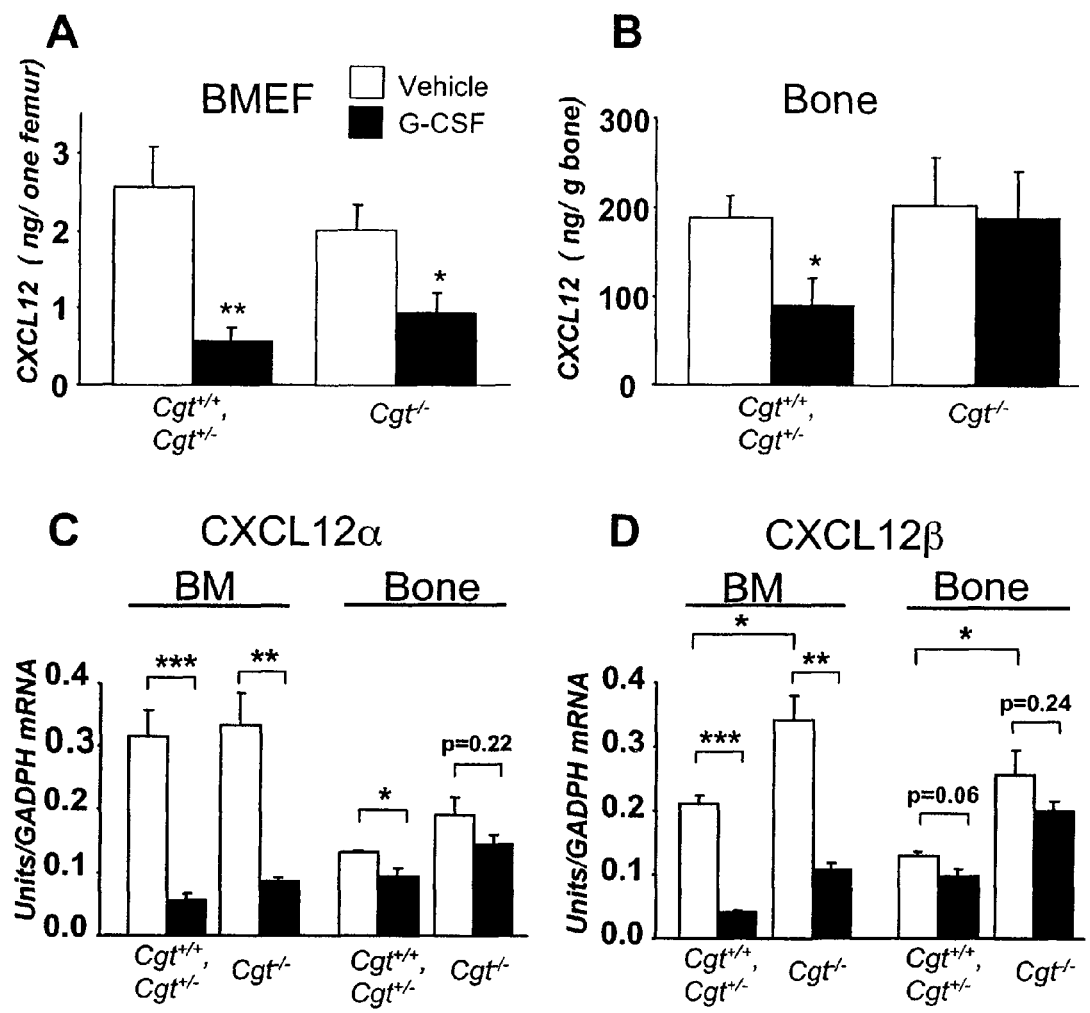
FIG. 3. CXCL12 in BM and bone during G-CSF-induced mobilization.
(A-B) CXCL12 protein levels in (A) BMEF and (B) bone were determined by ELISA. Cgt littermates were treated with either PBS/BSA or G-CSF; n=7-9 mice per group for BMEF and n=4-5 mice for bone groups.
(C, D) CXCL12 mRNA levels in BM and bone were determined by Q-PCR. Total RNA was extracted from BM and bone of control PBS/BSA- and G-CSF-treated mice. mRNA levels for (C) CXCL12α and (D) CXCL12β were quantified as described in Experimental Procedures. Data are normalized to GAPDH; n=4-5 mice per group. * p<0.05,  p<0.01, * p<0.001.

CXCL12 levels decrease in BMEF during mobilization and this effect has been suggested to induce cell egress. Therefore, we have determined CXCL12 levels by ELISA in the compact bone as well as in the BMEF of Cgt littermate mice treated with either control PBS/BSA or G-CSF. We confirmed that CXCL12 was greatly reduced in $Cgt^{+/+}$ and $^{+/-}$ BMEF after G-CSF injection (FIG. 3A). Unexpectedly, the CXCL12 protein in $Cgt^{-/-}$ BMEF was also significantly reduced by G-CSF (FIG. 3A), despite the fact that these mice do not mobilize HSPCs. While CXCL12 also decreased in the bone of normal littermate mice following G-CSF administration (FIG. 3B), there was no reduction of CXCL12 protein levels in the bone of $Cgt^{-/-}$ mice. These results indicate that CXCL12 levels in bone may correlate better than that of BM with the release of HSPCs.

Example 6

G-CSF-induced Transcriptional Downregulation of CXCL12

While proteases can clearly degrade CXCL12 in vitro, the maintenance of bone CXCL12 levels in $Cgt^{-/-}$ mice despite a robust BM proteolytic activity suggests the contribution of other regulatory mechanisms. To assess whether CXCL12 is regulated at the transcriptional level, we evaluated the expression of the two major isoforms of CXCL12 ($\alpha$ and $\beta$) by quantitative real-time RT-PCR (Q-PCR) in bone and BM tissues of Cgt littermates. The mRNA expression of both CXCL12 isoforms were profoundly decreased in BM after G-CSF in both $Cgt^{-/-}$ and normal littermates (FIG. 3C-D). CXCL12 mRNA levels in bone were moderately decreased after G-CSF treatment ($p<0.05$ for CXCL12$\alpha$, $p=0.06$ for CXCL12$\beta$). Although there was a trend toward decreased CXCL12 transcripts in $Cgt^{-/-}$ bone after G-CSF, the difference was not significant and mRNA levels were still higher in G-CSF-treated $Cgt^{-/-}$ bone than those of steady-state normal littermates (FIG. 3C-D). Thus, CXCL12 is transcriptionally regulated in both BM and bone tissues. Blunted transcriptional downregulation in Cgt$^{-/-}$ mice may contribute to the sustained CXCL12 protein levels in Cgt$^{-/-}$ bone.

Example 7

Osteoblast Activity is Altered in Cgt$^{-/-}$ Mice

Figure 4:
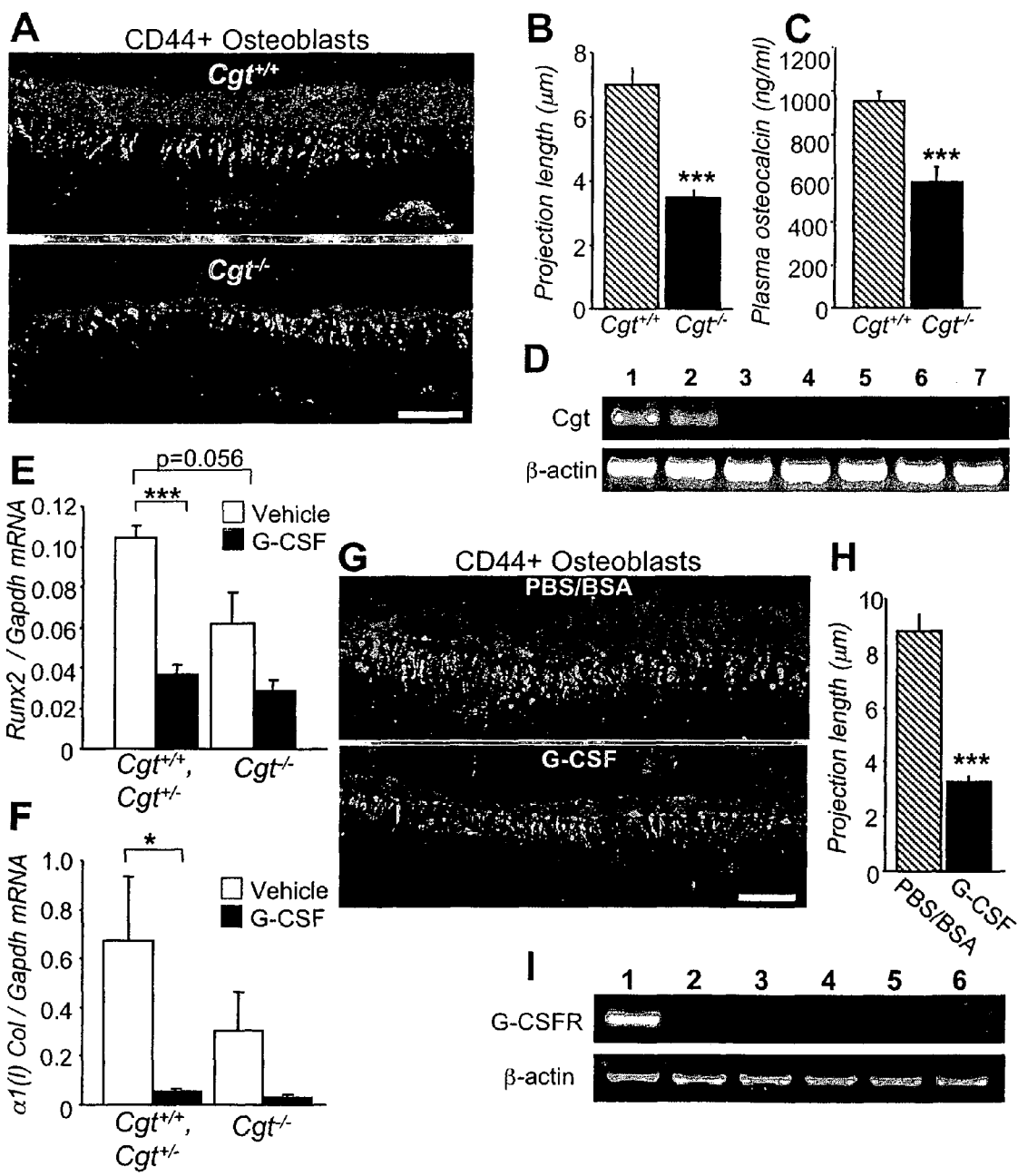
FIG. 4. Altered morphology and function of osteoblasts of $Cgt^{-/-}$ mice and G-CSF-stimulated wild-type mice.
(A) Projection images of bone lining osteoblasts of Cgt littermates. Green: CD44, blue: DAPI. bar: 10 µm.
(B) Average length of osteoblast projections into bone. The length of all projections in one area (30 µm width) were measured using Slidebook software. n=12 areas in 4 different sections from 3 different $Cgt^{+/+}$ and $^{-/-}$ littermate pairs are shown.
(C) Plasma osteocalcin levels in $Cgt^{+/+}$ and $^{-/-}$ littermates were determined by ELISA. n=6-9.
(D) Cgt mRNA expression assessed by RT-PCR. From lane 1 to 7: brain, bone, primary osteoblasts, UAMS-33, MC3T3-E1, ST2, MLO-Y4.
(E-F) Quantitative PCR of RNA extracts of BMNCs from control PBS/BSA-treated (open bars) and G-CSF-treated (closed bars) Cgt littermates. (E) Runx2 and (F) α1(I) collagen were quantified and data were normalized to GAPDH; n=4-5.
(G) Projection images of bone lining osteoblasts from young wild-type mice treated with vehicle PBS/BSA or G-CSF. Green: CD44, blue: DAPI. bar: 10 µm.
(H) Average length of osteoblast projections into bone.
(I) G-CSF receptor mRNA expression assessed by RT-PCR. From lane 1 to 6: BM, primary osteoblasts, UAMS-33, MC3T3-E1, ST2, MLO-Y4. * p<0.05, *** p<0.001.

We noted during the staining of osteocytes (FIG. 2H-I) that bone lining osteoblasts in Cgt$^{-/-}$ mice were generally flat with little cytoplasm and short projections into bone, while osteoblasts from littermate controls displayed a homogenous cobblestone-like appearance sending numerous and deep projections into the bone matrix (FIG. 4A-B). The osteoblast function was also altered in Cgt$^{-/-}$ mice since plasma osteocalcin levels were significantly reduced as compared with normal littermates (FIG. 4C; 39% reduction, n=6-9, p<0.001). However, the number of apoptotic osteoblasts in Cgt$^{-/-}$ mice, as determined by TUNEL assay, was not increased (data not shown). Further, the absence of Cgt expression was not directly responsible for the osteoblast dysfunction since Cgt mRNA was not detected in various osteoblast lineage cells (FIG. 4D). To confirm the absence of Cgt expression in osteoblastic cells, we cultured MC3T3-E1 and ST2 cell lines with ascorbic acid for 18 days to induce further maturation. Even under these differentiating conditions, no Cgt mRNA was detectable (FIG. 8A-B). These results thus suggest that osteoblast function is altered in Cgt$^{-/-}$ mice through an indirect mechanism.

Example 8

G-CSF Suppresses Osteoblast Activity

Considering the suppression of osteoblast activity in Cgt$^{-/-}$ mice and the fact that osteocalcin levels have been reported to be reduced after G-CSF administration (Takamatsu, Y., Simmons, P. J., Moore, R. J., Morris, H. A., To, L. B., and Levesque, J. P. (1998). Osteoclast-mediated bone resorption is stimulated during short-term administration of granulocyte colony-stimulating factor but is not responsible for hematopoietic progenitor cell mobilization. Blood 92, 3465-3473; Froberg, M. K., Garg, U. C., Stroncek, D. F., Geis, M., McCullough, J., and Brown, D. M. (1999). Changes in serum osteocalcin and bone-specific alkaline phosphatase are associated with bone pain in donors receiving granulocyte-colony-stimulating factor for peripheral blood stem and progenitor cell collection. Transfusion 39, 410-414), we reasoned that HSPC mobilization by G-CSF may be caused by a rapid downregulation in osteoblast activity. We evaluated the effect of G-CSF administration on the expression of Runx2, a transcription factor controlling osteoblast function and α1(I) collagen, a major osteoblast gene product and component of the bone matrix. The expression of both genes was dramatically downregulated by G-CSF administration in the bone marrow of Cgt$^{+/+}$ mice (FIG. 4E-F, levels of Runx2; 65% reduction, n=4, p<0.001, α1(I) collagen; 92% reduction, n=4, p<0.05). However, in Cgt$^{-/-}$ mice the steady-state levels of Runx2 and α1(I) collagen tended to be lower than control littermate mice and the downregulation following G-CSF administration was not as marked (FIG. 4E-F). Strikingly, bone-lining osteoblasts in G-CSF-treated age-matched wild-type C57BL/6 mice resembled those from steady-state Cgt$^{-/-}$ mice (FIG. 4G) and exhibited a flattened appearance with shorter projections into the bone matrix (FIG. 4H). Since osteoblasts do not express G-CSFR (FIG. 4I), these results indicate that G-CSF suppresses osteoblast activity through an indirect mechanism.

Example 9

Signals from the Sympathetic Nervous System Trigger G-CSF-induced Mobilization

Figure 5:
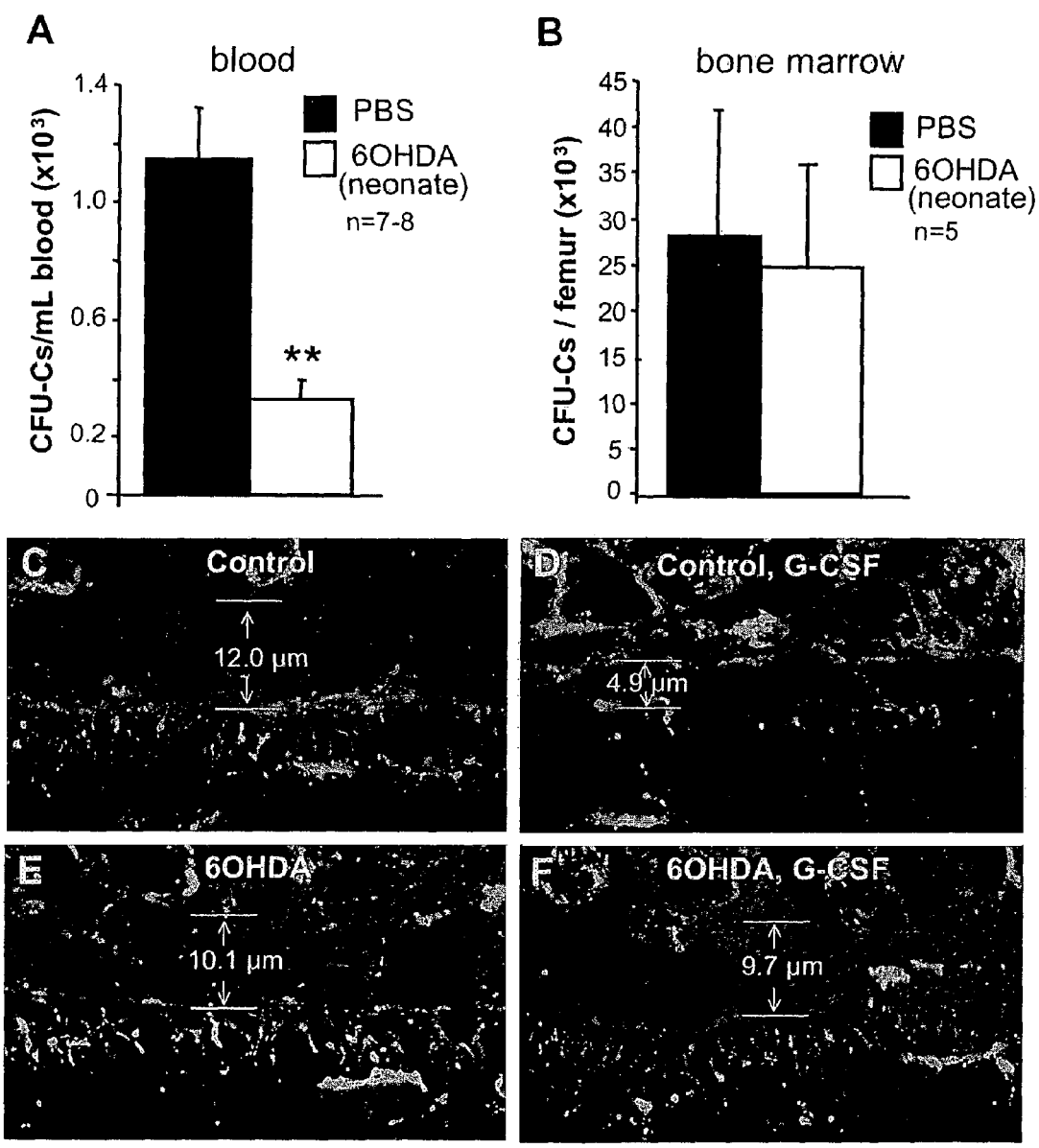
FIG. 5. 6OHDA treatment reveals a critical role for catecholaminergic neurons in G-CSF-mediated osteoblast suppression and HSPC mobilization.
(A) Catecholaminergic lesions were induced early postnatally with 6-hydroxydopamine (6OHDA) or vehicle s.c. injections and CFU-Cs were elicited by G-CSF after weaning.
(B) Numbers of CFU-Cs in steady-state BM from 6OHDA- and PBS-treated control mice at weaning age.
(C-F) Projection images from bone lining osteoblasts from steady-state or G-CSF-mobilized control vehicle or 6OHDA-treated mice.

Since Cgt$^{-/-}$ mice have severe neurological abnormalities (Coetzee, T., Fujita, N., Dupree, J., Shi, R., Blight, A., Suzuki, K., and Popko, B. (1996). Myelination in the absence of galactocerebroside and sulfatide: normal structure with abnormal function and regional instability. Cell 86, 209-219; Bosio, A., Binczek, E., and Stoffel, W. (1996). Functional breakdown of the lipid bilayer of the myelin membrane in central and peripheral nervous system by disrupted galactocerebroside synthesis. Proc Natl Acad Sci U S A 93, 13280-13285), we explored the possibility that signals emanating from the nervous system participate in HSPC mobilization. This possibility would be consistent with data showing that adrenergic stimulation reduces bone formation, indicating that bone formation and osteoblast function are regulated by the sympathetic nervous system (SNS)(Takeda, S., Elefteriou, F., Levasseur, R., Liu, X., Zhao, L., Parker, K. L., Armstrong, D., Ducy, P., and Karsenty, G. (2002). Leptin regulates bone formation via the sympathetic nervous system. Cell 111, 305-317). To test this hypothesis, we disrupted catecholaminergic neurons by serial perinatal injections of 6-hydroxydopamine (6OHDA)(Iversen, P. O., Benestad, H. B., and Nicolaysen, G. (1994). Haemorrhage-induced splenic vasodilation in the rat is mediated by sympathetic vasomotor nerves. Acta Physiol Scand 150, 373-379). 6OHDA treatment severely reduced the tissue content of catecholamines (Table S1). We found that the number of HSPCs mobilized by G-CSF was dramatically reduced in 6OHDA-lesioned mice compared to littermates injected with vehicle control (FIG. 5A), even though 6OHDA did not alter baseline CFU-C counts per bone (FIG. 5B). Strikingly, baseline bone lining osteoblast morphology was similar between control and 6OHDA-treated mice (FIGS. 5C and E). By contrast, G-CSF suppressed osteoblasts from control mice but not from 6OHDA-treated littermates (FIGS. 5D and F).

Figure 6:
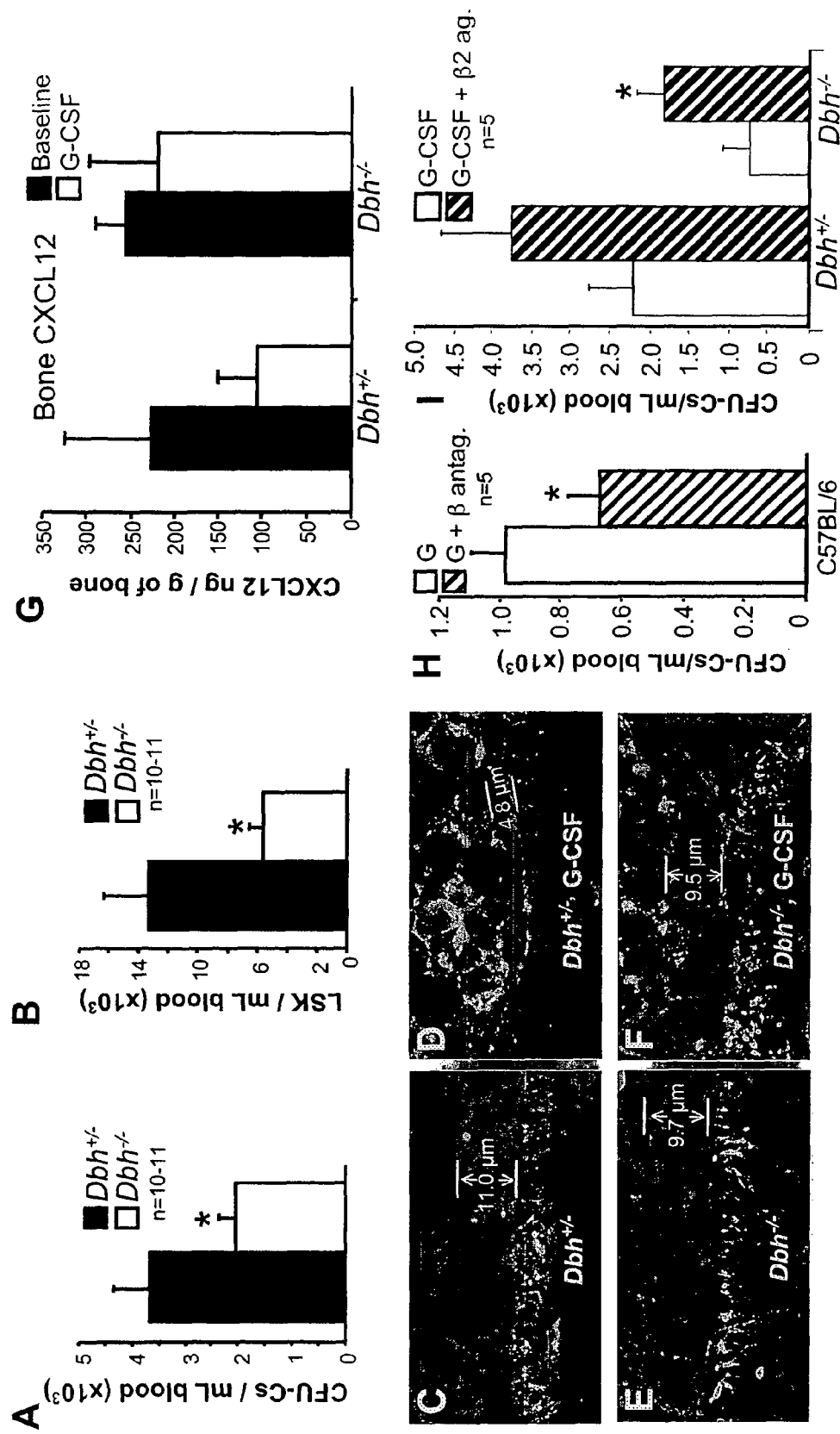
FIG. 6. G-CSF-induced mobilization requires adrenergic signals.
(A-B) $Dbh^{+/-}$ and $^{-/-}$ littermates were injected with G-CSF. Numbers of circulating (A) CFU-Cs and (B) HSC-enriched fraction (LSK cells, $Lin^{neg}$ $Sca-1^{pos}$ $c-kit^{pos}$) per ml of blood. (C-F) Projection images of bone-lining osteoblasts from $Dbh^{+/-}$ and $^{-/-}$ mice at (C-E) baseline and (D-F) after G-CSF.
(G) CXCL12 levels in protein extracts of bones from $Dbh^{+/-}$ and $^{-/-}$ littermates at baseline and after G-CSF.

Neonatal administration of 6OHDA damages both central and peripheral, dopaminergic and noradrenergic neurons, owing to the permeable blood-brain barrier of newborn mice. To distinguish between the two catecholaminergic pathways, we studied mice deficient in dopamine β-hydroxylase (Dbh$^{-/-}$), the enzyme necessary for the conversion of dopamine into norepinephrine (NE)(Thomas, S. A., Matsumoto, A. M., and Palmiter, R. D. (1995). Noradrenaline is essential for mouse fetal development. Nature 374, 643-646). G-CSF-triggered mobilization of CFU-Cs (FIG. 6A) and the stem cell-enriched fraction (Lin-Sca-1+c-kit+cells; FIG. 6B) was dramatically compromised in Dbh$^{-/-}$ compared to Dbh$^{+/-}$ littermates indicating that noradrenergic neurons were required for mobilization by G-CSF. Immunohistological analyses of osteoblasts also revealed that morphology correlated with the effectiveness of G-CSF to induce mobilization in that osteoblasts from G-CSF-treated Dbh$^{+/-}$ mice exhibited a flattened appearance and shorter projections whereas little change was observed in Dbh$^{+/-}$ mice (FIG. 6C-F). In addition, CXCL12 was reduced in bone protein extracts from Dbh$^{+/-}$ mice following G-CSF administration whereas CXCL12 levels were maintained in Dbh$^{-/-}$ animals (FIG. 6G). Additionally, treatment of C57BL6 mice for three weeks with a α-blocker (propranolol) significantly reduced (>20%) the number of HSPCs elicited by G-CSF (FIG. 6H). To evaluate whether the mobilization defect in Dbh$^{-/-}$ mice could be rescued by the administration of a β$_2$-adrenergic agonist, we treated a separate cohort of Dbh$^{+/-}$ and Dbh$^{-/-}$ animals with the clenbuterol two days before and during G-CSF administration. Clenbuterol rescued in part the mobilization defect in Dbh$^{-/-}$ mice and, interestingly, further enhanced mobilization in Dbh$^{+/-}$ controls (FIG. 61). By contrast, administration of clenbuterol, by itself, at the same dose schedule did not trigger mobilization (data not shown), suggesting that β$_2$-adrenergic signaling is not downstream of, but rather cooperates with other signals from the G-CSF receptor.

Example 10

G-CSF Acts Outside the Central Nervous System (CNS)

Recent studies have revealed that G-CSF can cross the blood brain barrier and that the G-CSFR is widely expressed by neurons in the CNS (Schneider, A., Kruger, C., Steigleder, T., Weber, D., Pitzer, C., Laage, R., Aronowski, J., Maurer, M. H., Gassler, N., Mier, W., et al. (2005). The hematopoietic factor G-CSF is a neuronal ligand that counteracts programmed cell death and drives neurogenesis. J Clin Invest 115, 2083-2098). That signals from the SNS originating from the hypothalamus can suppress bone formation also suggest the possibility of a G-CSF target in the CNS (Takeda, S., Elefteriou, F., Levasseur, R., Liu, X., Zhao, L., Parker, K. L., Armstrong, D., Ducy, P., and Karsenty, G. (2002). Leptin regulates bone formation via the sympathetic nervous system. Cell 111, 305-317). To address this issue, we implanted stereotaxically guide cannulae into lateral ventricules of C57BL/6 mice. One week after implantation, mice received G-CSF either directly in the CNS by intracerebroventricular (ICV) infusion or systemically by s.c. injection. As shown in FIG. 7A, robust HSPC mobilization occurred only when mice were treated systemically, indicating that the cellular target(s) of G-CSF lies in the periphery. Since 6OHDA does not penetrate the CNS of adult mice and causes transient damage of peripheral noradrenergic neurons (Livnat, S., Felten, S. Y., Carlson, S. L., Bellinger, D. L., and Felten, D. L. (1985). Involvement of peripheral and central catecholamine systems in neural-immune interactions. J Neuroimmunol 10, 5-30), we also evaluated whether G-CSF-elicited mobilization in adult 6OHDA-lesioned mice. We found that mobilization was significantly reduced in 6OHDA-treated adult mice (FIG. 7B), confirming that a disruption of noradrenergic neurons arising from peripheral sympathetic ganglia is sufficient to impair the egress of HSPC.

NE in peripheral tissues is synthesized and stored in sympathetic nerve endings. In response to sympathetic nerve impulses NE is released in the extracellular milieu to interact with its receptor target(s), and is then degraded or recycled. If G-CSF augmented NE release or disrupted its reuptake, we might expect a reduction in NE levels in tissues. To investigate this possibility, we measured NE by HPLC in hearts and bones of steady-state and G-CSF-treated C57BL/6 mice. While cardiac NE levels in mice that received a single dose of G-CSF were slightly reduced, we found a dramatic reduction in bone NE levels 3 h after G-CSF administration, suggesting that G-CSF may selectively stimulate the activity of the SNS in bone/BM tissues (FIG. 7C). Thus, taken together, these data suggest that G-CSF-induced adrenergic signals emerging from the peripheral nervous system regulate the egress of stem/progenitor cells from their bone marrow niche (FIG. 7D).

Example 11

Norepinephrine Decreases SDF-1 Secretion by a Stromal Cell Line

Studies were also done to determine the effect of norepinephrine or a beta receptor agonist on SDF-1 secretion by a stromal cell line and to determine if there is a correlation with stem cell egress. FIG. 13 shows that SDF-1 secretion, as measured by ELISA, decreased in a dose-dependent manner after 72 h exposure of the stromal cell line MS-5 to norepinephrine or to the beta-receptor agonist Isoproterenol. This corresponds with an increase in the stem cell egress.

Example 12

Stem Cell Egress is Decreased or Reduced in a Dose Dependent Manner Following Destruction of Dopaminergic and Noradrenergic Neurons Studies were done to determine the effect of destruction of dopaminergic and noradrenergic neurons on stem cell egress. In these studies, newborn C57BL/6 mice were injected subcutaneously with 6OHDA (100 mg/kg, Sigma) or vehicle (normal saline) on postnatal days 2, 4, 6, 8, and 9. Hematopoietic progenitor mobilization was induced at 34 weeks of age, by subcutaneous injection of AMD3100 (5 mg/kg) in normal saline. Peripheral blood was harvested retroorbitally one hour post injection. P-value was calculated using two-tailed Student's t-test assuming unequal variances. The results showed that stem cell egress was decreased in a dose dependent manner following destruction of dopaminergic and noradrenergic neurons (FIG. 14).

Example 13

Enhancement of Stem Cell Egress in the Presence of the Beta Agonist Clenbuterol

Studies were done to determine the effect of the beta agonist clenbuterol on stem cell egress. In this study, all drugs were dissolved in normal saline (0.9% w/v NaCl), with a delivery volume of 10 μL/g body mass. 10 μl/g saline i.p. or 2 mg/kg clenbuterol i.p. were given to adult (8-10 week old) C57BL6 mice 1 hour prior to hematopoietic progenitor mobilization induced by mg/kg AMD3100 s.c. Peripheral blood was harvested retroorbitally one hour post AMD3100 injection. P-value was calculated using two-tailed Student's t-test assuming unequal variances. The results demonstrated that by using the beta agonist clenbuterol, one can boost stem cell egress in a dose dependent manner (FIG. 15).

Example 14

Studies on Prostate Tumors to Determine the Presence or Expression of CXCL12 and Nerve Sprouting We have established orthotopic prostate tumors in immunodeficient NOD/SCID mice to assess whether a prostate tumor synthesizes CXCL12 and whether it contained nerve sprouting from sympathetic neurons. In these studies, the prostate gland was exposed surgically and injected with 10$^6$ PC3M cells that are stably transfected with the luciferase gene (PC3Mluc; gift from Dr. Jeronimo Blanco, CSIC, Barcelona, Spain). Tumor cells were monitored weekly by bioluminescence imaging. As shown in FIG. 16A, strong luminescence signal was recorded in the pelvis on day 20 after tumor cell injection. Upon shielding, luminescence was also detected in the right paw (FIG. 16B, arrow), suggesting the presence of bone metastasis. These data demonstrate the feasibility of tracking longitudinally the development of tumors in the same mouse. The mouse was sacrificed after these imaging studies, and the prostate tumor harvested for determination of CXCL12 content by ELISA and immunofluorescence staining of sympathetic fibers. A normal prostate from an age-matched NOD/SCID mouse was harvested for control CXCL12 content in healthy prostate. As shown in FIG. 17A, tumor tissues contained much greater levels of CXCL12 compared to healthy prostate tissues harvested from an age-matched healthy NOD/SCID mouse. To evaluate whether CXCL12 originated from the tumor cells or the stroma, we prepared lysates from cultured PC3M cells (devoid of stromal cells). We found that the chemokine was detectable neither in the cell lysate (FIG. 17A) nor in the supernatant (data not shown) of cultured PC3M cells, suggesting that CXCL12 indeed originates from the tumor microenvironment. Further, these data indicate that tumor cells can indeed change the function of prostate stromal cells, inducing their synthesis of CXCL12.

The prostate gland receives abundant innervation from both the sympathetic and parasympathetic divisions of the nervous system (McVary, K. T., McKenna, K. E., and Lee, C. (1998). Prostate innervation. Prostate Suppl 8, 2-13; Powell, M. S., Li, R., Dai, H., Sayeeduddin, M., Wheeler, T. M., and Ayala, G. E. (2005). Neuroanatomy of the normal prostate. Prostate 65, 52-57; Yonese, J., Kihara, K., Sato, K., Fukuda, H., Kamata, S., and Oshima, H. (2000). Sympathetic efferent pathways projecting to the prostate in the dog. Prostate 44, 225-232 Yonese, J., Kihara, K., Sato, K., Fukuda, H., Kamata, S., and Oshima, H. (2000). Sympathetic efferent pathways projecting to the prostate in the dog. Prostate 44, 225-232). Their roles in the secretory and contractile functions of the prostate are well recognized. In addition, there is evidence that autonomic innervation contributes to the growth and maintenance of the prostate gland. For example, selective surgical sympathectomy significantly reduced the weight of the denervated lobe while the weight of the intact side was unaffected (McVary, K. T., Razzaq, A., Lee, C., Venegas, M. F., Rademaker, A., and McKenna, K. E. (1994). Growth of the rat prostate gland is facilitated by the autonomic nervous system. Biol Reprod 51, 99-107). While the sprouting of neovessels in tumors has been extensively studied, much less is known about nerve sprouting in tumors. Perineural invasion has been reported in a large fraction of prostate adenocarcinomas (~85%) and is thought to represent the main mechanism by which prostate cancers penetrate the capsule and metastasize. Perineural invasion has been used as a prognostic marker that can predict progression, radiation therapy failure, and possibly biochemical recurrence (Anderson, P. R., Hanlon, A. L., Patchefsky, A., Al-Saleem, T., and Hanks, G. E. (1998). Perineural invasion and Gleason 7-10 tumors predict increased failure in prostate cancer patients with pretreatment PSA<10 ng/ml treated with conformal external beam radiation therapy. Int J Radiat Oncol Biol Phys 41, 1087-1092; Bastacky, S. I., Walsh, P. C., and Epstein, J. I. (1993). Relationship between perineural tumor invasion on needle biopsy and radical prostatectomy capsular penetration in clinical stage B adenocarcinoma of the prostate. Am J Surg Pathol 17, 336-341; Maru, N., Ohori, M., Kattan, M. W., Scardino, P. T., and Wheeler, T. M. (2001). Prognostic significance of the diameter of perineural invasion in radical prostatectomy specimens. Hum Pathol 32, 828-833; Villers, A., McNeal, J. E., Redwine, E. A., Freiha, F. S., and Stamey, T. A. (1989). The role of perineural space invasion in the local spread of prostatic adenocarcinoma. J Urol 142, 763-768). Although the mechanisms by which innervation influences progression and metastasis are not well understood, co-culture of mouse dorsal root ganglia with prostate cancer cells has been shown to enhance the growth of both the neural and tumor cells (Ayala, G. E., Wheeler, T. M., Shine, H. D., Schmelz, M., Frolov, A., Chakraborty, S., and Rowley, D. (2001). In vitro dorsal root ganglia and human prostate cell line interaction: redefining perineural invasion in prostate cancer. Prostate 49, 213-223).

We will test the possibility that signals from sympathetic innervation contribute to metastasis. To begin to investigate this possibility and provide proof-of-concept data, we have stained PC3Mluc tumor sections with an anti-tyrosine hydroxylase antibody (TH, specific to catecholaminergic neurons) to detect sprouting of noradrenergic fibers into the tumor tissue. As shown in FIG. 17B, specific TH staining was observed in the tumor tissue, indicating that sympathetic fiber sprouting has occurred in the tumor. Thus, these studies support the possibility that tumor stem cells may be retained in the primary tumor by the chemokine CXCL12 and that tumor stem cell retention may be regulated by sympathetic innervation. Since prostate cancer commonly metastasizes to the bone marrow/bone, it is also conceivable that sympathetic signals may retain these metastases in the bone and thus the inhibition of sympathetic signaling may affect the spread of initial bone metastases to other sites. It will thus be important to consider carefully both possibilities since sympathetic innervation of tumors may affect primary and secondary metastases.

To evaluate whether and if so how sympathetic signaling regulates the mobilization of prostate cancer cells in the blood circulation, we will need a cell line expressing a marker traceable in the bloodstream. To this end, we have transduced PC3luc and PC3Mluc cells with a lentiviral vector containing the GFP gene driven by the CMV promoter (FIG. 18A). Transduced GFP positive cells were sorted (FIG. 18B), expanded further in culture and frozen. An aliquot of these sorted cells was thawed, expanded again for few days in culture. As shown in FIG. 18C, all cells express high levels of GFP, suggesting that they have integrated and actively express the transgene. Thus, we now have PC3 and PC3M cells that express both the luciferase and the GFP genes. We will refer to these cells as PC3lucGFP and PC3MlucGFP. These results provide the proof-of-principle of using lentiviral transduction to downregulate genes in prostate cancer cells using short hairpin RNA interference (shRNA). We have successfully used this same vector, which contains the U6 promoter (FIG. 18A), to downregulate the expression of the Selel (ESL-1; ~90% reduction) or Fut7 (fucosyltransferase VII; ~85% reduction) genes in hematopoietic stem cells (unpublished data).

Example 15

Characterization of the Spatial Relationships of Sympathetic Innervation, CXCL12 Expression and Cancer Stem Cell Localization in Prostate Cancer Our preliminary results suggest that orthotopically grown human prostate tumors change the microenvironment in the prostate, leading to increased synthesis of CXCL12. To define better the spatial localization and interrelationships among sympathetic fibers, CXCL12 expression, and the cancer stem cell niche, we will carefully evaluate their spatial localization using immunofluorescence staining. We will establish prostate tumors in NOD/SCID mice as described in the preliminary data with the PC3 and PC3M cell lines expressing the luciferase gene. We will also prepare fresh frozen sections of normal murine prostate to characterize steady-state sympathetic innervation and CXCL12 expression in the prostate. Sections will be fixed with 4% paraformaldehyde in PBS containing 1 mM each $CaCl_2$ and $MgCl_2$ and permeabilized with 0.3% Triton X-100 in PBS. Staining for sympathetic fibers with anti-tyrosine hydroxylase and for the chemokine CXCL12 will be carried out essentially as in preliminary data (FIG. 17) and (Katayama, Y., Battista, M., Kao, W. M., Hidalgo, A., Peired, A. J., Thomas, S. A., and Frenette, P. S. (2006). Signals from the sympathetic nervous system regulate hematopoietic stem and progenitor cell egress from bone marrow. Cell 124, 407-421). Briefly, endogenous peroxidase will be quenched with 0.3% $H_2O_2$ in methanol, and then endogenous biotin inactivated using Vector Labs Avidin/Biotin Blocking Kit according to manufacturer's instructions. Tyrosine hydroxylase will be stained with rabbit anti-TH (Chemicon AB 152), and CXCL12 with goat anti-CXCL12 (Santa Cruz Biotechnology sc-6193), followed by biotinylated goat anti-rabbit IgG, Cy3-conjugated donkey anti-goat IgG and FITC-tyramide. Slides will be mounted in antifade mounting medium containing DAPI. In some experiments, we will include antibodies to stain CD133 or $\alpha 2\beta 1$ integrin (directly conjugated mouse monoclonal antibodies in the Cy5 channel) to assess whether a subset of PC3 or PC3M cells expresses putative prostate stem cell markers in vivo. These experiments will allow us to gain important insight about the extent and distribution of sympathetic innervation and chemokine production in the normal and cancerous prostate.

To correlate our findings with the model with a clinically relevant context, we will then carry out similar immunofluorescence stainings of sections obtained from human prostate cancer samples. Prostate cancer tissues will be obtained from the Urology Department at Mount Sinai Hospital. Tissues will be snap-frozen in OCT immediately after surgical removal to preserve the integrity of neural proteins. Tissue sections will be stained for TH, CXCL12 and CD133 to evaluate the spatial interrelationships between sympathetic nerves, chemokine expression and candidate prostate cancer stem cells. Both antibodies against TH and CXCL12 also react with the human antigen. We will use the mouse anti-CD133 (clone 293C3, Miltenyi) that has proved useful in immunoflurescence staining of prostate tissues (Richardson, G. D., Robson, C. N., Lang, S. H., Neal, D. E., Maitland, N. J., and Collins, A. T. (2004). CD133, a novel marker for human prostatic epithelial stem cells. J Cell Sci 117, 3539-3545).

Example 16

Studies to Determine Whether Reduced CXCR4-CXCL12 Function in Prostate Tumors Mobilizes Cancer Cells in the Circulation CXCL12 is a critical chemokine that retains HSC in the BM microenvironment. Our overall hypothesis posits that CXCL12 contributes to the retention of PTICs in the primary tumor and that reduction of CXCL12 is a critical factor leading to the spreading of cancer cells outside the prostate gland. Consistent with this possibility, we have found in our preliminary studies a high expression of CXCL12 in prostate glands harboring cancer cells. Thus these results suggest that the tumor cell can dramatically alter the function of stromal cells. This concept is consistent with recent studies evaluating the influence of breast cancer cells on tumor fibroblasts (Orimo, A., Gupta, P. B., Sgroi, D. C., Arenzana-Seisdedos, F., Delaunay, T., Naeem, R., Carey, V. J., Richardson, A. L., and Weinberg, R. A. (2005). Stromal fibroblasts present in invasive human breast carcinomas promote tumor growth and angiogenesis through elevated SDF-1/CXCL12 secretion. Cell 121, 335-348). It has been previously shown that most carcinomas express CXCR4 and that the CXCR4-CXCL12 axis plays a critical role in metastasis in models in which tumors cells were injected in the vasculature. In particular, PC3 cells express CXCR4, migrate toward CXCL12 and preferentially metastasize to the BM and bone when implanted orthotopically (Sun, Y. X., Schneider, A., Jung, Y., Wang, J., Dai, J., Cook, K., Osman, N. I., Koh-Paige, A. J., Shim, H., Pienta, K. J., et al. (2005). Skeletal localization and neutralization of the SDF-1(CXCL12)/CXCR4 axis blocks prostate cancer metastasis and growth in osseous sites in vivo. J Bone Miner Res 20, 318-329; Yang, M., Jiang, P., Sun, F. X., Hasegawa, S., Baranov, E., Chishima, T., Shimada, H., Moossa, A. R., and Hoffman, R. M. (1999). A fluorescent orthotopic bone metastasis model of human prostate cancer. Cancer Res 59, 781-786). However, emerging data strongly suggest that reduction of CXCL12 in the bone/bone marrow compartment plays a key role in the egress of HSCs from their niche (Katayama, Y., Battista, M., Kao, W. M., Hidalgo, A., Peired, A. J., Thomas, S. A., and Frenette, P. S. (2006). Signals from the sympathetic nervous system regulate hematopoietic stem and progenitor cell egress from bone marrow. Cell 124, 407-421; Petit, I., Szyper-Kravitz, M., Nagler, A., Lahav, M., Peled, A., Habler, L., Ponomaryov, T., Taichman, R. S., Arenzana-Seisdedos, F., Fujii, N., et al. (2002). G-CSF induces stem cell mobilization by decreasing bone marrow SDF-1 and up-regulating CXCR4. Nat Immunol 3, 687-694; Semerad, C. L., Christopher, M. J., Liu, F., Short, B., Simmons, P. J., Winkler, I., Levesque, J. P., Chappel, J., Ross, F. P., and Link, D. C. (2005). G-CSF potently inhibits osteoblast activity and CXCL12 mRNA expression in the bone marrow. Blood In press., (available online as first Edition)). We propose to assess the possibility that reductions in the CXCL12 chemokine in the tumor microenvironment increases the release of cancers cells in the bloodstream, leading to increased metastasis.

We have transduced PC3 and PC3M cells that stably express the luciferase gene with a lentiviral construct containing the GFP gene under the CMV promoter. Luciferase expression will allow us to monitor distant metastases whereas GFP expression will permit to quantify the number of circulating tumor cells under baseline conditions and following treatment with stem cell "mobilizers". Firstly, we will evaluate the effect of CXCR4 inhibition, using the specific antagonist AMD3100 on circulating tumor cells. Blood from NOD/SCID mice bearing tumors (day 35 for PC3lucGFP, day 15 for PC3MlucGFP) will be harvested at baseline to evaluate steady-state levels of circulating tumor cells. Mice will then be injected with AMD3100 at a dose of 5 mg/Kg and blood will be harvested 1 h later to evaluate the number of circulating tumor cells. This dose has been shown to be optimal for the mobilization of HSCs in the circulation (Broxmeyer, H. E., Orschell, C. M., Clapp, D. W., Hangoc, G., Cooper, S., Plett, P. A., Liles, W. C., Li, X., Graham-Evans, B., Campbell, T. B., et al. (2005). Rapid mobilization of murine and human hematopoietic stem and progenitor cells with AMD3100, a CXCR4 antagonist. J Exp Med 201, 1307-1318). To quantify the absolute counts of tumor cells, we will determine the number of circulating nucleated cells using an automatic cell counter (available in the PI's laboratory), and the proportion of GFP+ cells will be evaluated by flow cytometry in which a large sampling (>500,000 events) will be acquired owing to the rarity of circulating tumor cells. We expect that the administration of AMD3100 will increase the number of circulating tumor cells.

To evaluate the effect of CXCR4 inhibition on prostate cancer metastasis, we will establish PC3lucGFP (or PC3MlucGFP) tumors orthotopically in NOD/SCID mice. Prior to the development of spontaneous metastasis (to be determined experimentally ~day 20 for PC3lucGFP and ~day 10 for PC3MlucGFP), mice will be divided in two groups: one group will be treated with AMD3100 5 mg/Kg daily for three consecutive days and the other group will be injected with vehicle. Mice will then be monitored weekly with bioluminescence imaging to evaluate the occurrence of distant metastasis. The precise location and burden of tumor cells will be determined by dissection of affected tissues and quantitation of the luciferase or GFP signal.

As an alternative to the systemic administration of a CXCR4 antagonist, we will inhibit RNA transcription using lentiviral-delivered short hairpin RNA (shRNA). We have successfully used a lentiviral vector to knockdown the expression of selectin ligands on circulating neutrophils by transduction of hematopoietic stem cells. This vector is the same as that used in our preliminary results to generate PC3luc and PC3Mluc cells expressing GFP (FIG. 18). We will select four different hairpin oligonucleotides specific to human CXCR4 which will be ligated into the HpaI and XhoI sites downstream to the U6 promoter of the lentiviral vector. We will also include a CXCR4 oligonucleotide in which 2-3 nucleotides are mutated (scrambled) to serve as control. The correct in-frame insertion will be confirmed by sequencing. In our previous experience with knockdown of the Selel and Fut7 in HSCs, about half of shRNA constructs profoundly (~85-90%) inhibit the expression of the target gene. We will thus transduce PC3luc and PC3Mluc cells with vectors containing shRNA sequences targeting CXCR4 and evaluate the level of inhibition using FACS analysis and real-time quantitative PCR. We have seen in the past a good correlation between mRNA levels determined by quantitative PCR and the surface protein levels (data not shown). We will then sort transduced cells (GFP+) from the vector found to exhibit the greatest inhibition. If the inhibition is less than 85%, we will select other oligonucleotides that will yield at least 85% downregulation. We will then establish orthotopic prostate tumors in NOD/SCID mice with the newly generated control and CXCR4-knockdown in PC3luc and PC3Mluc cells. We will monitor in occurrence of metastasis using in vivo imaging of the luciferase signal with the Xenogen IVIS system and the number of circulating tumor cells by FACS with the GFP signal. Since we postulate that CXCR4-CXCL12 retains tumor cells in the prostate, we expect that the number of circulating prostate cancer cells deficient in CXCR4 will be increased. Unlike the aforementioned experiments with a CXCR4 inhibitor in which the effect is transient, it is not clear whether the number of metastases will be affected with the knockdown approach since permanent reductions in CXCR4 expression will also affect the ability of circulating cancer cells to migrate to metastatic sites. We can distinguish between these possibilities by monitoring the effect of CXCR4 downregulation on the numbers of circulating tumor cells (GFP+) and metastatic sites (luciferase+).

Discussion

Regulated CXCL12 Expression in Bone

Several studies have suggested that a CXCL12 chemokine gradient between BM and blood, modifiable by secreted proteases, plays a key role in HSPC mobilization (Levesque, J. P., Hendy, J., Takamatsu, Y., Williams, B., Winkler, I. G., and Simmons, P. J. (2002). Mobilization by either cyclophosphamide or granulocyte colony-stimulating factor transforms the bone marrow into a highly proteolytic environment. Exp Hematol 30, 440-449; Petit, I., Szyper-Kravitz, M., Nagler, A., Lahav, M., Peled, A., Habler, L., Ponomaryov, T., Taichman, R. S., Arenzana-Seisdedos, F., Fujii, N., et al. (2002). G-CSF induces stem cell mobilization by decreasing bone marrow SDF-1 and up-regulating CXCR4. Nat Immunol 3, 687-694). That HSPC mobilization was virtually absent in $Cgt^{-/-}$ mice despite robust proteolytic activity in the BM led us to investigate alternative expression and regulation of CXCL12. Our studies suggest that CXCL12 is expressed at high levels in bone tissues and that bone CXCL12 is dysregulated in $Cgt^{-/-}$ mice following G-CSF administration. CXCL12 staining in bone matrix was specific, as shown by appropriate antibody controls, and by confirmation with a sandwich ELISA. The fact that fluorescence staining in bone was not reported in knockin mice expressing GFP under the CXCL12 locus is likely due to differential sorting mechanisms for GFP and CXCL12 (Tokoyoda, K., Egawa, T., Sugiyama, T., Choi, B. I., and Nagasawa, T. (2004). Cellular niches controlling B lymphocyte behavior within bone marrow during development. Immunity 20, 707-718). In addition, these results are consistent with a recent report documenting the presence of CXCL12 in bone (Sun, Y. X., Schneider, A., Jung, Y., Wang, J., Dai, J., Cook, K., Osman, N. I., Koh-Paige, A. J., Shim, H., Pienta, K. J., et al. (2005). Skeletal localization and neutralization of the SDF-1 (CXCL12)/CXCR4 axis blocks prostate cancer metastasis and growth in osseous sites in vivo. J Bone Miner Res 20, 318-329).

Although osteocytes represent the major cell type present in bone, they do not appear to synthesize CXCL12. Indeed, no co-localization between CXCL12 and osteocyte staining was observed in vivo (FIG. 2) and, in addition, an osteocyte-like cell line (MLO-Y4 cells) (Kato, Y., Windle, J. J., Koop, B. A., Mundy, G. R., and Bonewald, L. F. (1997). Establishment of an osteocyte-like cell line, MLO-Y4. J Bone Miner Res 12, 2014-2023) neither expresses CXCL12 mRNA nor secretes CXCL12 protein (Y. K. and P. S. F., unpublished data). BM CXCL12 has been reported to be expressed by endothelial cells, osteoblasts and other stromal elements (Ponomaryov, T., Peled, A., Petit, I., Taichman, R. S., Habler, L., Sandbank, J., Arenzana-Seisdedos, F., Magerus, A., Caruz, A., Fujii, N., et al. (2000). Induction of the chemokine stromal-derived factor-1 following DNA damage improves human stem cell function. J Clin Invest 106, 1331-1339; Tokoyoda, K., Egawa, T., Sugiyama, T., Choi, B. I., and Nagasawa, T. (2004). Cellular niches controlling B lymphocyte behavior within bone marrow during development. Immunity 20, 707-718). The presence of high concentrations of CXCL12 in bone and its striking downregulation with G-CSF-induced osteoblast suppression, strongly suggest that it is primarily deposited by osteoblasts, like many other growth factors that are enriched in bone matrix (Hauschka, P. V., Chen, T. L., and Mavrakos, A. E. (1988). Polypeptide growth factors in bone matrix. Ciba Found Symp 136, 207-225). Indeed, recent studies suggest that BM CXCL12 is largely produced by osteoblasts (Semerad, C. L., Christopher, M. J., Liu, F., Short, B., Simmons, P. J., Winkler, I., Levesque, J. P., Chappel, J., Ross, F. P., and Link, D. C. (2005). G-CSF potently inhibits osteoblast activity and CXCL12 mRNA expression in the bone marrow. Blood In press., (available online as first Edition)). Despite reduced osteoblastic activity, CXCL12 levels are preserved in bone tissues of $Cgt^{-/-}$ mice (FIG. 3), suggesting alternative or compensatory mechanisms by other stromal elements unconstrained by neural control.

Whereas CXCL12 is constitutively expressed in a variety of tissues and is necessary for vascular development, intriguing data have suggested that certain cytokines (e.g. TGF-β and TNF-α) can decrease CXCL12 transcript levels in stromal and fibroblastic cell lines via yet unidentified mechanisms (Wright, N., de Lera, T. L., Garcia-Moruja, C., Lillo, R., Garcia-Sanchez, F., Caruz, A., and Teixido, J. (2003). Transforming growth factor-beta1 down-regulates expression of chemokine stromal cell-derived factor-1: functional consequences in cell migration and adhesion. Blood 102, 1978-1984; Fedyk, E. R., Jones, D., Critchley, H. O., Phipps, R. P., Blieden, T. M., and Springer, T. A. (2001). Expression of stromal-derived factor-1 is decreased by IL-1 and TNF and in dermal wound healing. J Immunol 166, 5749-5754). TNF-α was a prime contender to mediate osteoblast suppression because it is reported to inhibit Runx2, α1(I) collagen, and osteocalcin (Nanes, M. S. (2003). Tumor necrosis factor-alpha: molecular and cellular mechanisms in skeletal pathology. Gene 321, 1-15), and to be essential for CXCL12 down-regulation in the BM during immunization (Ueda, Y., Yang, K., Foster, S. J., Kondo, M., and Kelsoe, G. (2004). Inflammation Controls B Lymphopoiesis by Regulating Chemokine CXCL12 Expression. J Exp Med 199, 47-58). However, it is unlikely that TNF-α contributes to HSPC mobilization since G-CSF administration does not alter TNF-α mRNA levels in the BM and, more importantly, TNF-α-deficient mice mobilize normal numbers of HSPCs (Y. K. and P. S. F., unpublished data). Whether Runx2, a key transcription factor that controls the expression of multiple osteoblast genes, influences the expression of CXCL12 is being tested in the laboratory.

We have found no evidence that soluble GCs are involved in the survival, growth or function of osteoblasts since i) neither osteoblasts (FIG. 4) nor hematopoietic cells (Katayama, Y., and Frenette, P. S. (2003). Galactocerebrosides are required postnatally for stromal-dependent bone marrow lymphopoiesis. Immunity 18, 789-800) express the Cgt gene; ii) neither the lymphopoietic nor the HSPC mobilization phenotype are transplantable (Katayama, Y., and Frenette, P. S. (2003). Galactocerebrosides are required postnatally for stromal-dependent bone marrow lymphopoiesis. Immunity 18, 789-800 and FIG. 1F); iii) GCs are not detectable in BMEF or mouse serum; iv) although Cgt mRNA can be detected by Q-PCR in BM and bone, GCs are not detectable by high performance thin layer chromatography, even when alkali-stable lipid extracts from>2 femurs are loaded (FIG. 9 A-C). Thus, we believe that the low expression level of Cgt in these organs originates from Schwann cells that support the transmission of neuronal signals.

Neuronal Regulation of the Stem Cell Niche

Neural control of bone metabolism, both trophic and atrophic, has been suggested by numerous experimental and clinical observations. A rich network of nerve fibers was described in bone and bone marrow tissues with a significant subset of fibers reaching stromal cells (Calvo, W. (1968). The innervation of the bone marrow in laboratory animals. Am J Anat 123, 315-328; Yamazaki, K., and Allen, T. D. (1990). Ultrastructural morphometric study of efferent nerve terminals on murine bone marrow stromal cells, and the recognition of a novel anatomical unit: the "neuro-reticular complex". Am J Anat 187, 261-276). Immunolabeling studies have revealed a close association between glutamate-, catecholamine- or peptide-containing nerve fibers and osteoblasts or osteoclasts in the endosteum (Hohmann, E. L., Elde, R. P., Rysavy, J. A., Einzig, S., and Gebhard, R. L. (1986). Innervation of periosteum and bone by sympathetic vasoactive intestinal peptide-containing nerve fibers. Science 232, 868-871; Serre, C. M., Farlay, D., Delmas, P. D., and Chenu, C. (1999). Evidence for a dense and intimate innervation of the bone tissue, including glutamate-containing fibers. Bone 25, 623-629; Takeda, S., Elefteriou, F., Levasseur, R., Liu, X., Zhao, L., Parker, K. L., Armstrong, D., Ducy, P., and Karsenty, G. (2002). Leptin regulates bone formation via the sympathetic nervous system. Cell 111, 305-317 Takeda, S., Elefteriou, F., Levasseur, R., Liu, X., Zhao, L., Parker, K. L., Armstrong, D., Ducy, P., and Karsenty, G. (2002). Leptin regulates bone formation via the sympathetic nervous system. Cell 111, 305-317). Blockade of glutamate receptors was reported to reduce the DNA binding activity and expression of Runx2 in cultured osteoblasts (Hinoi, E., Fujimori, S., and Yoneda, Y. (2003). Modulation of cellular differentiation by N-methyl-D-aspartate receptors in osteoblasts. Faseb J 17, 1532-1534). Clinically, peripheral neuropathy in diabetes is an independent risk factor for lower bone mineral density (Rix, M., Andreassen, H., and Eskildsen, P. (1999). Impact of peripheral neuropathy on bone density in patients with type 1 diabetes. Diabetes Care 22, 827-831). On the other hand, hyperadrenergic activity and osteopenia are characteristic signs of a human disease commonly referred to as reflex sympathetic dystrophy. Therapeutic sympathectomy was formerly used to decrease the discrepancies in limb length in children affected with poliomyelitis, underscoring the possibility of a dual effect of bone innervation on bone formation (Ring, P. A. (1961). The influence of the nervous system upon the growth of bones. J Bone Jt Surg 43B, 121-140). The effect of the sympathetic nervous system on bone formation has only recently been elucidated using genetic models (Chien, K. R., and Karsenty, G. (2005). Longevity and lineages: toward the integrative biology of degenerative diseases in heart, muscle, and bone. Cell 120, 533-544). These studies revealed that leptin induced bone loss through SNS-derived signals originating in the ventromedial hypothalamic nuclei (Takeda, S., Elefteriou, F., Levasseur, R., Liu, X., Zhao, L., Parker, K. L., Armstrong, D., Ducy, P., and Karsenty, G. (2002). Leptin regulates bone formation via the sympathetic nervous system. Cell 111, 305-317). The atrophic appearance of osteoblasts in both G-CSF-treated wild-type mice and steady-state Cgt$^{-/-}$ mice, and the fact that osteoblasts do not express G-CSFR or Cgt genes, strongly supported the possibility that the rapid G-CSF-mediated osteoblast suppression is controlled by the nervous system.

Several lines of evidence indeed indicate that sympathetic signals contribute to the dramatic reduction in osteoblast function that follows G-CSF administration. Firstly, the administration of 6OHDA in neonatal or adult mice inhibited mobilization without toxicity to the HSPC content in the BM. Secondly, G-CSF-induced HSPC mobilization was severely altered in NE-deficient mice. Thirdly, osteoblast function was suppressed by G-CSF in control mice but not in mice with impaired SNS activity. Fourthly, mobilization efficiency correlated with bone CXCL12 levels which were suppressed in Dbh$^{+/-}$ and preserved in Dbh$^{-/-}$ mice. Fifthly, the administration of a β$_2$-adrenergic agonist rescued the mobilization defect in Dbh$^{-/-}$ mice and enhanced mobilization in control mice. Finally, administration of a β-adrenergic antagonist significantly reduced mobilization. The lower inhibition observed with β-blockers compared with neonate 6OHDA-treated or Dbh$^{-/-}$ mice may result from incomplete inhibition of noradrenergic signaling. Consistent with this possibility, pharmacologic inhibition of β-adrenergic receptors did not affect bone resorption to the extent observed for genetic ablation of the β$_2$-adrenergic receptor (Elefteriou, F., Ahn, J. D., Takeda, S., Starbuck, M., Yang, X., Liu, X., Kondo, H., Richards, W. G., Bannon, T. W., Noda, M., et al. (2005). Leptin regulation of bone resorption by the sympathetic nervous system and CART. Nature 434, 514-520).

While we found a strong correlation between osteoblast suppression and HSPC mobilization, our studies do not prove a causal relationship. It is interesting that another stem cell niche was recently identified near endothelial cells (Kiel, M. J., Yilmaz, O. H., Iwashita, T., Terhorst, C., and Morrison, S. J. (2005). SLAM family receptors distinguish hematopoietic stem and progenitor cells and reveal endothelial niches for stem cells. Cell 121, 1109-1121). While it is temping to speculate that sympathetic innervation, which accompanies the BM vasculature, may regulate the endothelial stem cell niche, whether osteoblasts can influence the attraction of these stem cells in the BM is unknown.

The involvement of the SNS in HSPC mobilization suggested that the target of G-CSF may be extramedullary and may in fact be neuronal or glial. On the other hand, G-CSFR expression on a transplantable hematopoietic cell was shown to be required for G-CSF-induced mobilization (Liu, F., Poursine-Laurent, J., and Link, D. C. (2000). Expression of the G-CSF receptor on hematopoietic progenitor cells is not required for their mobilization by G-CSF. Blood 95, 3025-3031). Based on studies describing leptin-mediated neuronal control of osteoblast function (Takeda, S., Elefteriou, F., Levasseur, R., Liu, X., Zhao, L., Parker, K. L., Armstrong, D., Ducy, P., and Karsenty, G. (2002). Leptin regulates bone formation via the sympathetic nervous system. Cell 111, 305-317; Elefteriou, F., Ahn, J. D., Takeda, S., Starbuck, M., Yang, X., Liu, X., Kondo, H., Richards, W. G., Bannon, T. W., Noda, M., et al. (2005). Leptin regulation of bone resorption by the sympathetic nervous system and CART. Nature 434, 514-520) and the fact that leptin and G-CSF receptors display a high degree of homology (Tartaglia, L. A., Dembski, M., Weng, X., Deng, N., Culpepper, J., Devos, R., Richards, G. J., Campfield, L. A., Clark, F. T., Deeds, J., and et al. (1995). Identification and expression cloning of a leptin receptor, OB-R. Cell 83, 1263-1271), we have considered the possibility that G-CSF signals directly in the hypothalamus through the leptin receptor. However, expression of the leptin receptor does not appear to be required for HSPC mobilization since it proceeds normally in leptin receptor-deficient db/db mice (FIG. 10). In addition, the impaired mobilization after ICV infusion of G-CSF or in mice that have a peripheral SNS defect (6OHDA-lesioned adult mice), indicate that the cellular target for G-CSF is in the periphery.

Our results suggest that G-CSF may increase sympathetic tone in bone and that both G-CSF and adrenergic signaling cooperate to trigger HSPC egress (FIG. 7D). Supporting evidence for a cooperation between these signals comes from the fact that clenbuterol does not by itself induce mobilization but it can rescue at least in part the defect in Dbh$^{-/-}$ mice and can enhance the mobilizing effects of G-CSF in Dbh$^{+/-}$ mice. Whether G-CSF can modulate the release/reuptake of NE by acting directly on neurons of sympathetic ganglia or via neighboring glial cells, is currently unknown.

Trophic Neuronal Signals to Osteoblast

The constitutive suppression of osteoblast function in Cgt$^{-/-}$ mice might be due to increased sympathetic tone (Takeda, S., Elefteriou, F., Levasseur, R., Liu, X., Zhao, L., Parker, K. L., Armstrong, D., Ducy, P., and Karsenty, G. (2002). Leptin regulates bone formation via the sympathetic nervous system. Cell 111, 305-317) or alternatively, a reduction in putative neurally transmitted trophic signals. Osteoblasts have been reported to express receptors for several neuropeptides, suggesting that they could indeed integrate multiple neuronal signals (Togari, A. (2002). Adrenergic regulation of bone metabolism: possible involvement of sympathetic innervation of osteoblastic and osteoclastic cells. Microsc Res Tech 58, 77-84). We have measured NE turnover in cardiac tissues of Cgt littermates and found a longer half-life in Cgt$^{-/-}$ hearts, indicating reduced peripheral sympathetic activity in the null mice (FIG. 11). Although this finding would be consistent with their mobilization defect, $\beta_2$-adrenergic stimulation did not rescue the mobilization defect of Cgt$^{-/-}$ animals (data not shown). It is possible that the phenotype of Cgt$^{-/-}$ mice may result from their basal osteoblast suppression. The difference in osteoblast morphology at baseline between Cgt$^{-/-}$ mice and mice harboring compromised SNS signaling clearly suggests deficits in Cgt$^{-/-}$ mice that lie outside noradrenergic innervation (compare FIG. 4A with FIGS. 5E and 6E) and imply the presence of physiological neurally transmitted trophic signals to osteoblasts.

A Common Niche for Stem Cells and Common Lymphoid Progenitor Cells?

We have previously reported a lymphopoietic defect in Cgt$^{-/-}$ mice that was associated with a deficit in the stromal microenvironment supporting lymphoid commitment (Katayama, Y., and Frenette, P. S. (2003). Galactocerebrosides are required postnatally for stromal-dependent bone marrow lymphopoiesis. Immunity 18, 789-800). The steady-state reductions in CLP content in the BM of Cgt$^{-/-}$ mice and the reduced osteoblast activity reported herein suggest that osteoblasts may support the commitment of stem cells toward the lymphoid lineage. Consistent with this possibility, postnatal ablation of osteoblasts was recently shown to reduce bone marrow B cell content by ~97% while HSPC numbers were much less affected (Visnjic, D., Kalajzic, Z., Rowe, D. W., Katavic, V., Lorenzo, J., and Aguila, H. L. (2004). Hematopoiesis is severely altered in mice with an induced osteoblast deficiency. Blood 103, 3258-3264), indicating that the earliest committed lymphoid progenitor cell may require osteoblasts for survival, proliferation or differentiation. A close relationship between CLP and the stem cell niche is further suggested by the expression of the Notch-1 ligand, Jagged-1, in the osteoblastic niche and the fact that Notch-1 can promote both stem cell self-renewal and differentiation toward the lymphoid lineage (Radtke, F., Wilson, A., Stark, G., Bauer, M., van Meerwijk, J., MacDonald, H. R., and Aguet, M. (1999). Deficient T cell fate specification in mice with an induced inactivation of Notch1. Immunity 10, 547-558; Pui, J. C., Allman, D., Xu, L., DeRocco, S., Karnell, F. G., Bakkour, S., Lee, J. Y., Kadesch, T., Hardy, R. R., Aster, J. C., and Pear, W. S. (1999). Notch1 expression in early lymphopoiesis influences B versus T lineage determination. Immunity 11, 299-308; Calvi, L. M., Adams, G. B., Weibrecht, K. W., Weber, J. M., Olson, D. P., Knight, M. C., Martin, R. P., Schipani, E., Divieti, P., Bringhurst, F. R., et al. (2003). Osteoblastic cells regulate the haematopoietic stem cell niche. Nature 425, 841-846). More differentiated B cell precursors (B220+ flk2+), distant from the endosteum, are closely associated with CXCL12-expressing stromal cells, which do not express the Notch-1 ligands Jagged-1 or Delta-like-1 (Tokoyoda, K., Egawa, T., Sugiyama, T., Choi, B. I., and Nagasawa, T. (2004). Cellular niches controlling B lymphocyte behavior within bone marrow during development: Immunity 20, 707-718). Further studies are thus needed to determine whether the nervous system influences homeostatic migration of stem cells among cellular niches in the BM.

In summary, we show here that the sympathetic nervous system regulates the egress of stem and progenitor cells from their niche. These results raise the interesting possibility that alterations in the sympathetic tone may explain the conspicuous variability in mobilization efficiencies among normal donors (Korbling, M., Huh, Y. O., Durett, A., Mirza, N., Miller, P., Engel, H., Anderlini, P., van Besien, K., Andreeff, M., Przepiorka, D., and et al. (1995). Allogeneic blood stem cell transplantation: peripheralization and yield of donor-derived primitive hematopoietic progenitor cells (CD34+ Thy-1dim) and lymphoid subsets, and possible predictors of engraftment and graft-versus-host disease. Blood 86, 2842-2848). Modulation of the sympathetic outflow to the stem cell niche represents a novel strategy to increase the efficiency of HSPC harvests for stem cell-based therapeutics.

TABLE S1

Tissue catecholamines after 6-hydroxydopamine treatment

| Mouse strain | Treatment | Norepinephrine (pmol/mg tissue) | Epinephrine (pmol/mg tissue) | Dopamine (pmol/mg tissue) |
|---|---|---|---|---|
| C57BL/6 | PBS | 2507 ± 344 | 142 ± 13 | 98 ± 20 |
| C57BL/6 | 6OHDA | 49 ± 10* | 41 ± 20* | 10 ± 10* |

Hearts from 5 week-old C57BL6 mice treated perinatally with 6-hydroxydopamine (6OHDA) or PBS control were homogenized in 0.1 M trichloroacetic acid containing 10 mM sodium acetate, 0.1 mM EDTA, 1 μM isoproterenol (as internal standard), and 10.5% methanol (pH 3.8). Catecholamine levels were determined by HPLC at the Neurochemistry Core Lab, Vanderbilt University's Center for Molecular Neuroscience research (Nashville, Tenn.). * p<0.05 compared with PBS control. n=3 mice.

TABLE S2

Norepinephrine turnover in hearts of Cgt littermates

| CGT genotype | $k\ (h^{-1})$ | $T_{1/2}(h)$ | $T_t(h)$ | Steady-state level (pg/mg wet weight) | Level after AMPT inhibition, 4 h (pg/mg wet weight) | Steady-state synthesis rate (pg/mg/h) |
|---|---|---|---|---|---|---|
| Cgt+/+, Cgt+/− | 0.214 | 3.24 | 4.68 | 465 ± 59 | 198 ± 38 | 99.4 ± 12.7 |
| Cgt−/− | 0.102 | 6.82 | 9.84 | 503 ± 46 | 335 ± 32 | 51.1 ± 4.6 |

Values reported as mean±sem, n=4-5. $T_{1/2}$=half-life; $T_t$=turnover time; k=rate constant were calculated as described below; α-methyl-p-tyrosine, AMPT.

Decline in tissue levels of norepinephrine obeys first order kinetics (Brodie, B. B., Costa, E., Dlabac, A., Neff, N. H., and Smookler, H. H. (1966). Application of steady state kinetics to the estimation of synthesis rate and turnover time of tissue catecholamines. J Pharmacol Exp Ther 154, 493-498 Brodie, B. B., Costa, E., Dlabac, A., Neff, N. H., and Smookler, H. H. (1966). Application of steady state kinetics to the estimation of synthesis rate and turnover time of tissue catecholamines. J Pharmacol Exp Ther 154, 493-498):

$$\text{rate of decline} = \frac{-d[A]}{dt} = [A] \tag{I}$$

where k is the rate constant, [A] is the concentration of norepinephrine, and t is time.
Solving the first order equation (I):

$$[A]_t = [A]_0 e^{-kt} \tag{II}$$

where $[A]_t$ is concentration of norepinephrine at time t, and $[A]_0$ is the initial (steady state) concentration.
solving equation (II) for k:

$$k = \frac{\ln([A]_0/[A]_t)}{t} \tag{III}$$

At steady state, synthesis rate equals rate of decline. Substituting $[A]_0$ for [A] in equation (I) we obtain steady state synthesis rate:

$$\text{steady state synthesis rate} = \frac{-d[A]_0}{dt} = [A]_0 \tag{IV}$$

Half life is the time it takes for the concentration to reach half its original level, i.e. when $[A]_0/[A]_t=2$. Substituting the value and solving equation (III) for t:

$$T_{1/2} = \frac{\ln 2}{k} \tag{V}$$

where $T_{1/2}$ is half-life.
Turnover time is the time it takes for the steady state synthesis rate to produce the level of norepinephrine at steady state:

$$T_t = \frac{\text{steady state concentration}}{\text{steady state synthesis rate}} = \frac{[A]_0}{k[A]_0} = \frac{1}{k} \tag{VI}$$

TABLE S3

Primers used for PCR

| Gene | Primer sequence |
|---|---|
| CXCL12α forward* | 5'- CAA CAC TCC AAA CTG TGC CCT TCA -3' (SEQ ID NO: 3) |
| CXCL12α reverse* | 5'- TCC TTT GGG CTG TTG TGC TTA CT -3' (SEQ ID NO: 4) |
| CXCL12β forward* | 5'- GGC TGA AGA ACA ACA ACA GAC AAG -3' (SEQ ID NO: 5) |
| CXCL12β reverse* | 5'- GTT CCT CGG GCG TCT GAC TC -3' (SEQ ID NO: 6) |
| GAPDH forward* | 5'- TTG GCA TTG TGG AAG GGC TCA T -3' (SEQ ID NO: 7) |
| GAPDH reverse* | 5'- GAT GAC CTT GCC CAC AGC CTT -3' (SEQ ID NO: 8) |
| CGT forward* | 5'- TGG CTT TGT CCT GGT GTC TTT T -3' (SEQ ID NO: 9) |

TABLE S3-continued

Primers used for PCR

| Gene | Primer sequence |
|---|---|
| CGT reverse* | 5'- CTA GGT TCT TTG GTT TGG TTC C -3' (SEQ ID NO: 10) |
| Runx2 forward* | 5'- TCC GAA ATG CCT CCG CTG TTA T -3' (SEQ ID NO: 11) |
| Runx2 reverse* | 5'- GGA CCG TCC ACT GTC ACT TTA A -3' (SEQ ID NO: 12) |
| Col1a1 forward* | 5'- TCC CTG AAG TCA GCT GCA TA -3' (SEQ ID NO: 13) |
| Col1a1 reverse* | 5'- TGG GAC AGT CCA GTT CTT CAT -3' (SEQ ID NO: 14) |
| TNFα forward* | 5'- GCC ACC ACG CTC TTC TGT CTA C -3' (SEQ ID NO: 15) |
| TNFα reverse* | 5'- TGG GCT ACA GGC TTG TCA CTC G -3' (SEQ ID NO: 16) |
| CGT forward | 5'- CCA AGA CCA ACG CTG CCT AAT G -3' (SEQ ID NO: 17) |
| CGT reverse | 5'- TGA CAC CAG CTC CAA AAG ACA CC -3' (SEQ ID NO: 18) |
| G-CSFR foward | 5'- ACC CTG ACT GGA GTT ACC CTG AT -3' (SEQ ID NO: 19) |
| G-CSFR reverse | 5'- ATC TTT GCC TGT TGG TCC -3' (SEQ ID NO: 20) |
| β-actin foward | 5'- TGT GAT GGT GGG AAT GGG TCA G -3' (SEQ ID NO: 21) |
| β-actin reverse | 5'- TTT GAT GTC ACG CAC GAT TTC C -3' (SEQ ID NO: 22) |

PCR conditions were 95° C. for 2 min; 40 cycles of 95° C. for 15 s, 55° C. for 15 s, 72° C. for 30 s; 1 cycle of 95° C. for 15 s, 60° C. for 15 s, 95° C. for 15 s.

* primers for Q-PCR, no mark; primers for conventional RT-PCR.

ADDITIONAL REFERENCES

Bissell, M. J., and Labarge, M. A. (2005). Context, tissue plasticity, and cancer: are tumor stem cells also regulated by the microenvironment? Cancer Cell 7, 17-23.

Brugger, W., Bross, K. J., Glatt, M., Weber, F., Mertelsmann, R., and Kanz, L. (1994). Mobilization of tumor cells and hematopoietic progenitor cells into peripheral blood of patients with solid tumors. Blood 83, 636-640.

Craig, J. I., Langlands, K., Parker, A. C., and Anthony, R. S. (1994). Molecular detection of tumor contamination in peripheral blood stem cell harvests. Exp Hematol 22, 898-902.

Demirkazik, A., Kessinger, A., Armitage, J. O., Bierman, P. J., Lynch, J., Vose, J., Chan, W., and Sharp, J. G. (2001). Progenitor and lymphoma cells in blood stem cell harvests: impact on survival following transplantation. Bone Marrow Transplant 28, 207-212.

Hidalgo, A., and Frenette, P. S. (2005). Enforced fucosylation of neonatal CD34+ cells generates selectin ligands that enhance the initial interactions with microvessels but not homing to bone marrow. Blood 105, 567-575.

Hidalgo, A., Weiss, L. A., and Frenette, P. S. (2002). Functional selectin ligands mediating human CD34(+) cell interactions with bone marrow endothelium are enhanced postnatally. J Clin Invest 110, 559-569.

Kobayashi, T., Kihara, K., Hyochi, N., Masuda, H., and Sato, K. (2003). Spontaneous regeneration of the seriously injured sympathetic pathway projecting to the prostate over a long period in the dog. BJU Int 91, 868-872.

Mintz, B., and Illmensee, K. (1975). Normal genetically mosaic mice produced from malignant teratocarcinoma cells. Proc Natl Acad Sci USA 72, 3585-3589.

Moss, T. J., Sanders, D. G., Lasky, L. C., and Bostrom, B. (1990). Contamination of peripheral blood stem cell harvests by circulating neuroblastoma cells. Blood 76, 1879-1883.

Rennie, P. S., Bowden, J. F., Bruchovsky, N., Frenette, P. S., Foekens, J. A., and Cheng, H. (1987). DNA and protein components of nuclear acceptor sites for androgen receptors in the rat prostate. J Steroid Biochem 27, 513-520.

What is claimed is:

1. A method of increasing or promoting the mobilization of hematopoietic stem cells or progenitor cells from the bone marrow to the peripheral blood of a mammal, the method comprising administering to the mammal a therapeutically effective amount of a beta adrenergic receptor agonist and a mobilizer of hematopoietic stem cells or progenitor cells, wherein the beta adrenergic receptor agonist and the mobilizer are administered concurrently, wherein the mobilization of hematopoietic stem cells or progenitor cells from the bone marrow to the peripheral blood is thereby increased or promoted in said mammal.

2. The method of claim 1, wherein the mobilizer is characterized by its ability to decrease or block the expression, synthesis or function of stromal-derived factor-1 (CXCL12) or is characterized by its ability to block or antagonize CXC chemokine receptor 4 (CXCR4).

3. The method of claim 2, wherein the mobilizer is a nucleic acid which is a small interfering RNA (siRNA) molecule or an antisense molecule specific for CXCL12.

4. The method of claim 1, wherein the beta adrenergic agonist is a β2 adrenergic agonist.

5. The method of claim 1, wherein the beta adrenergic agonist is selected from the group consisting of isoproterenol, metaproterenol, albuterol, terbutaline, salmeterol, salbutamine, bitolterol, pirbuterol acetate, formoterol, epinephrine, and norepinephrine.

6. The method of claim 1, wherein the mobilizer of hematopoietic stem cells or progenitor cells is selected from the group consisting of a small organic molecule, a polypeptide, and a carbohydrate.

7. The method of claim 6, wherein the small organic molecule is AMD3100 or an analog, derivative or a combination thereof.

8. The method of claim 6, wherein the polypeptide is selected from the group consisting of a cytokine, a colony stimulating factor, a protease or a chemokine.

9. The method of claim 8, wherein the cytokine is selected from the group consisting of interleukin-1 (IL-1), interleukin-3 (IL-3), interleukin-6 (IL-6), interleukin-11 (IL-11), interleukin-7 (IL-7), and interleukin-12 (IL-12).

10. The method of claim 8, wherein the colony stimulating factor is selected from the group consisting of granulocyte colony stimulating factor (G-CSF), granulocyte-macrophage colony stimulating factor (GM-CSF), macrophage colony stimulating factor (M-CSF), stem cell factor, FLT-3 ligand or a combination thereof.

11. The method of claim 8, wherein the protease is selected from the group consisting of a metalloproteinase, a serine protease, a cysteine protease and a dipeptidyl peptidase-1.

12. The method of claim 11 wherein the metalloproteinase is MMP2 or MMP9, the serine protease is cathepsin G or elastase, the cysteine protease is cathepsin K or the dipeptidyl peptidase-1 is DDP-1 or CD26.

13. The method of claim 8, wherein the chemokine is CXCL12, or a chemokine other than CXCL12 selected from the group consisting of interleukin-8 (IL-8), Mip-1α, and Groβ.

14. The method of claim 6, wherein the carbohydrate is a sulfated carbohydrate selected from the group consisting of Fucoidan and sulfated dextran.

15. A method for obtaining a population of hematopoietic stem cells or progenitor cells from a subject, the method comprising the steps of:
   a. administering a beta adrenergic receptor agonist and a mobilizer of hematopoietic stem cells or progenitor cells to the subject in an amount sufficient to mobilize the hematopoietic stem cells or progenitor cells from the bone marrow to the peripheral blood of the subject, wherein the beta adrenergic receptor agonist and the mobilizer are administered concurrently; and
   b. collecting/harvesting the mobilized cells from the peripheral blood by apheresis.

16. The method of claim 15, wherein the mobilizer is characterized by its ability to decrease the expression, synthesis, or function of the chemokine, stromal-derived factor-1 (CXCL12), or wherein the mobilizer is characterized by its ability to block or antagonize CXC chemokine receptor 4 (CXCR4).

17. The method of claim 16, wherein the mobilizer that blocks or antagonizes CXCR4 is AMD3100 or an analog, derivative or combination thereof.

18. The method of claim 16, wherein the mobilizer is a nucleic acid which is a small interfering RNA (siRNA) molecule or an antisense molecule specific for CXCL12.

19. The method of claim 15, wherein the beta adrenergic agonist is a β2 adrenergic agonist.

20. The method of claim 15, wherein the beta adrenergic agonist is selected from the group consisting of isoproterenol, metaproterenol, albuterol, terbutaline, salmeterol, salbutamine, bitolterol, pirbuterol acetate, formoterol, epinephrine, and norepinephrine.

21. The method of claim 15, wherein the mobilizer of hematopoietic stem cells or progenitor cells is selected from the group consisting of a small organic molecule, a polypeptide, and a carbohydrate.

22. The method of claim 21, wherein the polypeptide is selected from the group consisting of a cytokine, a colony stimulating factor, a protease or a chemokine.

23. The method of claim 22, wherein the cytokine is selected from the group consisting of interleukin-1 (IL-1), interleukin-3 (IL-3), interleukin-6 (IL-6), interleukin-11 (IL-11), interleukin-7 (IL-7), and interleukin-12 (IL-12).

24. The method of claim 22, wherein the colony stimulating factor is selected from the group consisting of granulocyte colony stimulating factor (G-CSF), granulocyte-macrophage colony stimulating factor (GM-CSF), macrophage colony stimulating factor (M-CSF), stem cell factor, FLT-3 ligand or a combination thereof.

25. The method of claim 22, wherein the protease is selected from the group consisting of a metalloproteinase, a serine protease, a cysteine protease and a dipeptidyl peptidase-1.

26. The method of claim 22, wherein the chemokine is CXCL12, or a chemokine other than CXCL12 selected from the group consisting of interleukin-8(IL-8), Mip-1α, and Groβ.

27. The method of claim 21, wherein the carbohydrate is a sulfated carbohydrate selected from the group consisting of Fucoidan and sulfated dextran.

28. A method of treating a subject in need of therapy with an agent that stimulates mobilization of bone marrow cells from the bone marrow to the peripheral blood, comprising administering to a subject a therapeutically effective amount of a beta adrenergic receptor agonist and a mobilizer of hematopoietic stem cells or progenitor cells in a pharmaceutically acceptable carrier, wherein the beta adrenergic receptor agonist and the mobilizer are administered concurrently, and wherein the mobilization of bone marrow cells from the bone marrow to the peripheral blood is thereby stimulated in said subject and said subject is provided said needed therapy.

29. The method of claim 25 wherein the metalloproteinase is MMP2 or MMP9, the serine protease is cathepsin G or elastase, the cysteine protease is cathepsin K or the dipeptidyl peptidase-1 is DDP-1 or CD26.

\* \* \* \* \*

SEQUENCE LISTING

<160> NUMBER OF SEQ ID NOS: 24

<210> SEQ ID NO 1
<211> LENGTH: 67
<212> TYPE: PRT
<213> ORGANISM: Homo sapiens

<400> SEQUENCE: 1

Lys Pro Val Ser Leu Ser Tyr Arg Cys Pro Cys Arg Phe Phe Glu Ser
 1               5                  10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

```
Val Cys Ile Asp Pro Lys Leu Lys Trp Ile Gln Glu Tyr Leu Glu Lys
 50                  55                  60

Ala Leu Asn
 65
```

<210> SEQ ID NO 2
<211> LENGTH: 360
<212> TYPE: PRT
<213> ORGANISM: Homo sapiens

<400> SEQUENCE: 2

```
Met Glu Gly Ile Ser Ser Ile Pro Leu Pro Leu Gln Ile Tyr Thr
  1               5                  10                  15

Ser Asp Asn Tyr Thr Glu Glu Met Gly Ser Gly Asp Tyr Asp Ser Met
                 20                  25                  30

Lys Glu Pro Cys Phe Arg Glu Glu Asn Ala Asn Phe Asn Lys Ile Phe
                 35                  40                  45

Leu Pro Thr Ile Tyr Ser Ile Ile Phe Leu Thr Gly Ile Val Gly Asn
 50                  55                  60

Gly Leu Val Ile Leu Val Met Gly Tyr Gln Lys Lys Leu Arg Ser Met
 65                  70                  75                  80

Thr Asp Lys Tyr Arg Leu His Leu Ser Val Ala Asp Leu Leu Phe Val
                 85                  90                  95

Ile Thr Leu Pro Phe Trp Ala Val Asp Ala Val Ala Asn Trp Tyr Phe
                100                 105                 110

Gly Asn Phe Leu Cys Lys Ala Val His Val Ile Tyr Thr Val Asn Leu
                115                 120                 125

Tyr Ser Ser Val Leu Ile Leu Ala Phe Ile Ser Leu Asp Arg Tyr Leu
130                 135                 140

Ala Ile Val His Ala Thr Asn Ser Gln Arg Pro Arg Lys Leu Leu Ala
145                 150                 155                 160

Glu Lys Val Val Tyr Val Gly Val Trp Ile Pro Ala Leu Leu Leu Thr
                165                 170                 175

Ile Pro Asp Phe Ile Phe Ala Asn Val Ser Glu Ala Asp Asp Arg Tyr
                180                 185                 190

Ile Cys Asp Arg Phe Tyr Pro Asn Asp Leu Trp Val Val Val Phe Gln
                195                 200                 205

Phe Gln His Ile Met Val Gly Leu Ile Leu Pro Gly Ile Val Ile Leu
                210                 215                 220

Ser Cys Tyr Cys Ile Ile Ile Ser Lys Leu Ser His Ser Lys Gly His
225                 230                 235                 240

Gln Lys Arg Lys Ala Leu Lys Thr Thr Val Ile Leu Ile Leu Ala Phe
                245                 250                 255

Phe Ala Cys Trp Leu Pro Tyr Tyr Ile Gly Ile Ser Ile Asp Ser Phe
                260                 265                 270

Ile Leu Leu Glu Ile Ile Lys Gln Gly Cys Glu Phe Glu Asn Thr Val
                275                 280                 285

His Lys Trp Ile Ser Ile Thr Glu Ala Leu Ala Phe Phe His Cys Cys
                290                 295                 300

Leu Asn Pro Ile Leu Tyr Ala Phe Leu Gly Ala Lys Phe Lys Thr Ser
305                 310                 315                 320

Ala Gln His Ala Leu Thr Ser Val Ser Arg Gly Ser Ser Leu Lys Ile
                325                 330                 335

Leu Ser Lys Gly Lys Arg Gly Gly His Ser Ser Val Ser Thr Glu Ser
                340                 345                 350
```

```
Glu Ser Ser Ser Phe His Ser Ser
        355             360
```

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
caacactcca aactgtgccc ttca                                    24

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
tcctttgggc tgttgtgctt act                                     23

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
ggctgaagaa caacaacaga caag                                    24

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gttcctcggg cgtctgactc                                         20

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ttggcattgt ggaagggctc at                                      22

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
gatgaccttg cccacagcct t                                       21

<210> SEQ ID NO 9
<211> LENGTH: 22
<212> TYPE: DNA
<213> ORGANISM: Artificial Sequence

```
<220> FEATURE:
<223> OTHER INFORMATION: primer

<400> SEQUENCE: 9
tggctttgtc ctggtgtctt tt                                              22

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
ctaggttctt tggtttggtt cc                                              22

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
tccgaaatgc ctccgctgtt at                                              22

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
ggaccgtcca ctgtcacttt aa                                              22

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tccctgaagt cagctgcata                                                 20

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
tgggacagtc cagttcttca t                                               21

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
gccaccacgc tcttctgtct ac                                              22
```

```
<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
tgggctacag gcttgtcact cg                                              22

<210> SEQ ID NO 17
<211> LENGTH: 22
<212> TYPE: DNA
<213> ORGANISM: Artificial Sequence
<220> FEATURE:
<223> OTHER INFORMATION: primer

<400> SEQUENCE: 17
ccaagaccaa cgctgcctaa tg                                              22

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
tgacaccagc tccaaaagac acc                                             23

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
accctgactg gagttaccct gat                                             23

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
atctttgcct gttggtcc                                                   18

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
tgtgatggtg ggaatgggtc ag                                              22

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
```
tttgatgtca cgcacgattt cc                                              22

<210> SEQ ID NO 23
<211> LENGTH: 3542
<212> TYPE: DNA
<213> ORGANISM: Homo sapiens

<400> SEQUENCE: 23

```
gcactttcac tctccgtcag ccgcattgcc cgctcggcgt ccggcccccg acccgcgctc    60
gtccgcccgc ccgcccgccc gcccgcgcca tgaacgccaa ggtcgtggtc gtgctggtcc   120
tcgtgctgac cgcgctctgc ctcagcgacg ggaagcccgt cagcctgagc tacagatgcc   180
catgccgatt cttcgaaagc catgttgcca gagccaacgt caagcatctc aaaattctca   240
acactccaaa ctgtgccctt cagattgtag cccggctgaa gaacaacaac agacaagtgt   300
gcattgaccc gaagctaaag tggattcagg agtacctgga gaaagcttta aacaagaggt   360
tcaagatgtg agagggtcag acgcctgagg aacccttaca gtaggagccc agctctgaaa   420
ccagtgttag ggaagggcct gccacagcct cccctgccag ggcagggccc caggcattgc   480
caagggcttt gttttgcaca ctttgccata ttttcaccat ttgattatgt agcaaaatac   540
atgacattta tttttcattt agtttgatta ttcagtgtca ctggcgacac gtagcagctt   600
agactaaggc cattattgta cttgccttat tagagtgtct ttccacggag ccactcctct   660
gactcagggc tcctgggttt tgtattctct gagctgtgca ggtggggaga ctgggctgag   720
ggagcctggc cccatggtca gccctagggt ggagagccac caagagggac gcctgggggt   780
gccaggacca gtcaacctgg gcaaagccta gtgaaggctt ctctctgtgg gatgggatgg   840
tggagggcca catgggaggc tcacccccctt ctccatccac atgggagccg ggtctgcctc   900
ttctgggagg gcagcagggc taccctgagc tgaggcagca gtgtgaggcc agggcagagt   960
gagacccagc cctcatcccg agcacctcca catcctccac gttctgctca tcattctctg  1020
tctcatccat catcatgtgt gtccacgact gtctccatgg ccccgcaaaa ggactctcag  1080
gaccaaagct ttcatgtaaa ctgtgcacca agcaggaaat gaaaatgtct tgtgttacct  1140
gaaaacactg tgcacatctg tgtcttgttt ggaatattgt ccattgtcca atcctatgtt  1200
tttgttcaaa gccagcgtcc tcctctgtga ccaatgtctt gatgcatgca ctgttccccc  1260
tgtgcagccg ctgagcgagg agatgctcct tgggcccttt gagtgcagtc ctgatcagag  1320
ccgtggtcct ttggggtgaa ctaccttggt tcccccactg atcacaaaaa catggtgggt  1380
ccatgggcag agcccaaggg aattcggtgt gcaccagggt tgacccagca ggattgctgc  1440
cccatcagtg ctccctcaca tgtcagtacc ttcaaactag gccaagccc  agcactgctt  1500
gaggaaaaca agcattcaca acttgttttt ggtttttaaa acccagtcca caaataacc   1560
aatcctggac atgaagattc tttcccaatt cacatctaac ctcatcttct tcaccatttg  1620
gcaatgccat catctcctgc cttcctcctg ggccctctct gctctgcgtg tcacctgtgc  1680
ttcgggccct tcccacagga catttctcta agagaacaat gtgctatgtg aagagtaagt  1740
caacctgcct gacatttgga gtgttcccct tccactgagg gcagtcgata gagctgtatt  1800
aagccactta aaatgttcac ttttgacaaa ggcaagcact tgtgggtttt tgttttgttt  1860
ttcattcagt cttacgaata cttttgccct ttgattaaag actccagtta aaaaaaattt  1920
taatgaagaa agtggaaaac aaggaagtca aagcaaggaa actatgtaac atgtaggaag  1980
taggaagtaa attatagtga tgtaatcttg aattgtaact gttcttgaat ttaataatct  2040
gtagggtaat tagtaacatg tgttaagtat tttcataagt atttcaaatt ggagcttcat  2100
```

```
ggcagaaggc aaacccatca acaaaaattg tcccttaaac aaaaattaaa atcctcaatc      2160
cagctatgtt atattgaaaa aatagagcct gagggatctt tactagttat aaagatacag      2220
aactctttca aaaccttttg aaattaacct ctcactatac cagtataatt gagttttcag      2280
tggggcagtc attatccagg taatccaaga tattttaaaa tctgtcacgt agaacttgga      2340
tgtacctgcc cccaatccat gaaccaagac cattgaattc ttggttgagg aaacaaacat      2400
gaccctaaat cttgactaca gtcaggaaag gaatcatttc tatttctcct ccatgggaga      2460
aaatagataa gagtagaaac tgcagggaaa attatttgca taacaattcc tctactaaca      2520
atcagctcct tcctggagac tgcccagcta aagcaatatg catttaaata cagtcttcca      2580
tttgcaaggg aaaagtctct tgtaatccga atctcttttt gctttcgaac tgctagtcaa      2640
gtgcgtccac gagctgttta ctagggatcc ctcatctgtc cctccgggac ctggtgctgc      2700
ctctacctga cactcccttg ggctccctgt aacctcttca gaggccctcg ctgccagctc      2760
tgtatcagga cccagaggaa ggggccagag gctcgttgac tggctgtgtg ttgggattga      2820
gtctgtgcca cgtgtttgtg ctgtggtgtg tcccctctg tccaggcact gagataccag      2880
cgaggaggct ccagagggca ctctgcttgt tattagagat tacctcctga gaaaaaaggt      2940
tccgcttgga gcagaggggc tgaatagcag aaggttgcac ctcccccaac cttagatgtt      3000
ctaagtcttt ccattggatc tcattggacc cttccatggt gtgatcgtct gactggtgtt      3060
atcaccgtgg gctccctgac tgggagttga tcgccttttcc caggtgctac accctttttcc     3120 agctggatga gaatttgagt gctctgatcc ctctacagag cttccctgac tcattctgaa      3180
ggagccccat tcctgggaaa tattccctag aaacttccaa atcccctaag cagaccactg      3240
ataaaaccat gtagaaaatt tgttattttg caacctcgct ggactctcag tctctgagca      3300
gtgaatgatt cagtgttaaa tgtgatgaat actgtatttt gtattgtttc aattgcatct      3360
cccagataat gtgaaaatgg tccaggagaa ggccaattcc tatacgcagc gtgctttaaa      3420
aaataaataa gaaacaactc tttgagaaac aacaatttct actttgaagt cataccaatg      3480
aaaaaatgta tatgcactta taattttcct aataaagttc tgtactcaaa tgtagccacc      3540
aa                                                                     3542

<210> SEQ ID NO 24
<211> LENGTH: 1912
<212> TYPE: DNA
<213> ORGANISM: Homo sapiens

<400> SEQUENCE: 24
ttttttttct tccctctagt gggcggggca gaggagttag ccaagatgtg actttgaaac        60
cctcagcgtc tcagtgccct tttgttctaa acaaagaatt ttgtaattgg ttctaccaaa       120
gaaggatata atgaagtcac tatgggaaaa gatgggagg agagttgtag gattctacat       180
taattctctt gtgcccttag cccactactt cagaatttcc tgaagaaagc aagcctgaat       240
tggtttttta aattgcttta aaaatttttt ttaactgggt taatgcttgc tgaattggaa       300
gtgaatgtcc attcctttgc ctcttttgca gatatacact tcagataact acaccgagga      360
aatgggctca ggggactatg actccatgaa ggaaccctgt ttccgtgaag aaaatgctaa       420
tttcaataaa atcttcctgc ccaccatcta ctccatcatc ttcttaactg gcattgtggg       480
caatggattg tcatcctgg tcatgggtta ccagaagaaa ctgagaagca tgacggacaa       540
gtacaggctg cacctgtcag tggccgacct cctctttgtc atcacgcttc ccttctgggc       600
agttgatgcc gtggcaaaact ggtactttgg gaacttccta tgcaaggcag tccatgtcat       660
```

-continued

```
ctacacagtc aacctctaca gcagtgtcct catcctggcc ttcatcagtc tggaccgcta    720
cctggccatc gtccacgcca ccaacagtca gaggccaagg aagctgttgg ctgaaaaggt    780
ggtctatgtt ggcgtctgga tccctgccct cctgctgact attcccgact tcatctttgc    840
caacgtcagt gaggcagatg acagatatat ctgtgaccgc ttctacccca atgacttgtg    900
ggtggttgtg ttccagtttc agcacatcat ggttggcctt atcctgcctg gtattgtcat    960
cctgtcctgc tattgcatta tcatctccaa gctgtcacac tccaagggcc accagaagcg   1020
caaggccctc aagaccacag tcatcctcat cctggctttc ttcgcctgtt ggctgcctta   1080
ctacattggg atcagcatcg actccttcat cctcctggaa atcatcaagc aagggtgtga   1140
gtttgagaac actgtgcaca agtggatttc catcaccgag gccctagctt tcttccactg   1200
ttgtctgaac cccatcctct atgctttcct tggagccaaa tttaaaacct ctgcccagca   1260
cgcactcacc tctgtgagca gagggtccag cctcaagatc ctctccaaag gaaagcgagg   1320
tggacattca tctgtttcca ctgagtctga gtcttcaagt tttcactcca gctaacacag   1380
atgtaaaaga cttttttta tacgataaat aactttttt taagttacac atttttcaga    1440
tataaaagac tgaccaatat tgtacagttt ttattgcttg ttggatttt gtcttgtgtt    1500 tctttagttt ttgtgaagtt taattgactt atttatataa attttttttg tttcatattg   1560
atgtgtgtct aggcaggacc tgtggccaag ttcttagttg ctgtatgtct cgtggtagga   1620
ctgtagaaaa gggaactgaa cattccagag cgtgtagtga atcacgtaaa gctagaaatg   1680
atccccagct gtttatgcat agataatctc tccattcccg tggaacgttt ttcctgttct   1740
taagacgtga ttttgctgta gaagatggca cttataacca aagcccaaag tggtatagaa   1800
atgctggttt ttcagttttc aggagtgggt tgatttcagc acctacagtg tacagtcttg   1860
tattaagttg ttaataaaag tacatgttaa acttaaaaaa aaaaaaaaaa aa           1912
```